US009487562B2

(12) United States Patent
Moellering et al.

(10) Patent No.: US 9,487,562 B2
(45) Date of Patent: Nov. 8, 2016

(54) STABILIZED POLYPEPTIDES AS REGULATORS OF RAB GTPASE FUNCTION

(75) Inventors: Raymond E. Moellering, La Jolla, CA (US); Gregory L. Verdine, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/126,642

(22) PCT Filed: Jun. 15, 2012

(86) PCT No.: PCT/US2012/042738
§ 371 (c)(1),
(2), (4) Date: Apr. 3, 2014

(87) PCT Pub. No.: WO2012/174423
PCT Pub. Date: Dec. 20, 2012

(65) Prior Publication Data
US 2014/0235549 A1    Aug. 21, 2014

Related U.S. Application Data

(60) Provisional application No. 61/498,382, filed on Jun. 17, 2011.

(51) Int. Cl.
| A61K 38/00 | (2006.01) |
| C07K 14/00 | (2006.01) |
| C07K 14/47 | (2006.01) |

(52) U.S. Cl.
CPC ......... *C07K 14/001* (2013.01); *C07K 14/4702* (2013.01); *A61K 38/00* (2013.01)

(58) Field of Classification Search
None
See application file for complete search history.

(56) References Cited

U.S. PATENT DOCUMENTS

| 4,730,006 | A | 3/1988 | Bohme et al. |
| 5,120,859 | A | 6/1992 | Webb |
| 5,364,851 | A | 11/1994 | Joran |
| 5,446,128 | A | 8/1995 | Kahn |
| 5,622,852 | A | 4/1997 | Korsmeyer |
| 5,663,316 | A | 9/1997 | Xudong |
| 5,708,136 | A | 1/1998 | Burrell et al. |
| 5,750,767 | A | 5/1998 | Carpino et al. |
| 5,811,515 | A | 9/1998 | Grubbs et al. |
| 5,824,483 | A | 10/1998 | Houston, Jr. et al. |
| 5,834,209 | A | 11/1998 | Korsmeyer |
| 5,856,445 | A | 1/1999 | Korsmeyer |
| 5,874,529 | A | 2/1999 | Gilon et al. |
| 5,922,863 | A | 7/1999 | Grubbs et al. |
| 5,955,593 | A | 9/1999 | Korsmeyer |
| 5,965,703 | A | 10/1999 | Horne et al. |
| 5,998,583 | A | 12/1999 | Korsmeyer |
| 6,051,554 | A | 4/2000 | Hornik et al. |
| 6,153,391 | A | 11/2000 | Picksley et al. |
| 6,184,344 | B1 | 2/2001 | Kent et al. |
| 6,271,198 | B1 | 8/2001 | Braisted et al. |
| 6,326,354 | B1 | 12/2001 | Gross et al. |
| 6,348,558 | B1 | 2/2002 | Harris et al. |
| 6,444,425 | B1 * | 9/2002 | Reed ............. C07K 14/47 435/6.16 |
| 6,610,657 | B1 | 8/2003 | Goueli |
| 6,613,874 | B1 | 9/2003 | Mazur et al. |
| 6,703,382 | B2 | 3/2004 | Wang et al. |
| 6,713,280 | B1 | 3/2004 | Huang et al. |
| 6,849,428 | B1 | 2/2005 | Evans et al. |
| 6,875,594 | B2 | 4/2005 | Muir et al. |
| 7,064,193 | B1 | 6/2006 | Cory et al. |
| 7,083,983 | B2 | 8/2006 | Lane et al. |
| 7,084,244 | B2 | 8/2006 | Gilon et al. |
| 7,183,059 | B2 | 2/2007 | Verdine et al. |
| 7,192,713 | B1 | 3/2007 | Verdine et al. |
| 7,202,332 | B2 | 4/2007 | Arora et al. |
| 7,247,700 | B2 | 7/2007 | Korsmeyer et al. |
| 7,538,190 | B2 | 5/2009 | Robinson et al. |
| 7,705,118 | B2 | 4/2010 | Arora et al. |
| 7,723,469 | B2 | 5/2010 | Walensky et al. |
| 7,745,573 | B2 | 6/2010 | Robinson et al. |
| 7,786,072 | B2 | 8/2010 | Verdine et al. |
| 8,324,428 | B2 | 12/2012 | Verdine et al. |
| 8,592,377 | B2 | 11/2013 | Verdine et al. |
| 8,895,699 | B2 | 11/2014 | Verdine et al. |

(Continued)

FOREIGN PATENT DOCUMENTS

| EP | 12159110 | 7/2012 |
| EP | 12159110 | 9/2012 |

(Continued)

OTHER PUBLICATIONS

Lindsay et al. The Journal of Biological Chemistry vol. 277, No. 14, Issue of Apr. 5, pp. 12190-12199, 2002.*
Merck Manuals Brain Tumors accessed Aug. 21, 2014 at URL merckmanuals.com/home/brain_spinal_cord_and_nerve_disorders/tumors_of_the_nervous_system/braintumors.html.*
Overview of Leukemia at URL merckmanuals.com/home/blood_disorders/leukemias/overview_of_leukemia.html?qt=Leukemia&alt=sh accessed Aug. 20, 2014.*
Merck Manual Colorectal Cancer accessed Aug. 21, 2014 at URL merckmanuals.com/home/digestive_disorders/tumors_of_the_digestive_system/colorectal_cancer.html.*
Merck Manual Prostate Cancer accessed Aug. 21, 2014 at URL: merckmanuals.com/home/kidney_and_urinary_tract_disorders/cancers_of_the_kidney_and genitourinary_tract/prostate_cancer.html?qt=prostate cancer&alt=sh.*

(Continued)

*Primary Examiner* — Jeanette Lieb
(74) *Attorney, Agent, or Firm* — Wolf, Greenfield & Sacks, P.C.

(57) ABSTRACT

The present invention provides inventive polypeptides comprising a C terminal RAB binding domain (RabBD) of RAB family interacting proteins (FIPs) stabilized by peptide stapling, and pharmaceutical compositions thereof. Also provided are methods for modulating RAB function comprising contacting an inventive stapled polypeptide with a RAB protein, and methods of treatment associated with modulation of RAB activity. The present invention also provides methods of making the inventive stapled polypeptides by ring closing metathesis of unstapled polypeptide precursors.

34 Claims, 25 Drawing Sheets

(56) References Cited

U.S. PATENT DOCUMENTS

| | | | |
|---|---|---|---|
| 8,957,026 | B2 | 2/2015 | Verdine et al. |
| 9,163,330 | B2 | 10/2015 | Verdine et al. |
| 2004/0038901 | A1 | 2/2004 | Basler et al. |
| 2004/0067503 | A1 | 4/2004 | Tan et al. |
| 2004/0171809 | A1 | 9/2004 | Korsmeyer et al. |
| 2005/0250680 | A1 | 11/2005 | Walensky et al. |
| 2006/0008848 | A1 | 1/2006 | Verdine et al. |
| 2006/0014675 | A1 | 1/2006 | Arora et al. |
| 2006/0148715 | A1 | 7/2006 | Tweardy |
| 2008/0262200 | A1 | 10/2008 | Nash |
| 2009/0047711 | A1 | 2/2009 | Nash |
| 2009/0088553 | A1 | 4/2009 | Nash |
| 2009/0149630 | A1 | 6/2009 | Walensky et al. |
| 2009/0176964 | A1 | 7/2009 | Walensky et al. |
| 2009/0326192 | A1 | 12/2009 | Nash et al. |
| 2010/0081611 | A1 | 4/2010 | Bradner et al. |
| 2010/0168388 | A1 | 7/2010 | Bernal et al. |
| 2010/0184628 | A1 | 7/2010 | Nash |
| 2010/0184645 | A1 | 7/2010 | Verdine et al. |
| 2010/0216688 | A1 | 8/2010 | Nash et al. |
| 2010/0234563 | A1 | 9/2010 | Arora et al. |
| 2010/0298201 | A1 | 11/2010 | Nash et al. |
| 2011/0028753 | A1 | 2/2011 | Verdine et al. |
| 2011/0144303 | A1 | 6/2011 | Nash et al. |
| 2011/0144306 | A1 | 6/2011 | Verdine et al. |
| 2011/0223149 | A1 | 9/2011 | Nash et al. |
| 2011/0263815 | A1 | 10/2011 | Nash |
| 2012/0082636 | A1 | 4/2012 | Walensky et al. |
| 2012/0172311 | A1 | 7/2012 | Nash et al. |
| 2012/0190818 | A1 | 7/2012 | Nash |
| 2012/0270800 | A1 | 10/2012 | Verdine et al. |
| 2013/0005943 | A1 | 1/2013 | Arora et al. |
| 2013/0023646 | A1 | 1/2013 | Nash et al. |
| 2013/0177979 | A1 | 7/2013 | Turkson |
| 2013/0211046 | A1 | 8/2013 | Verdine et al. |
| 2014/0005118 | A1 | 1/2014 | Verdine et al. |
| 2014/0011979 | A1 | 1/2014 | Verdine et al. |
| 2014/0162339 | A1 | 6/2014 | Verdine et al. |
| 2014/0256912 | A1 | 9/2014 | Moellering et al. |
| 2014/0323701 | A1 | 10/2014 | Nash et al. |
| 2015/0225471 | A1 | 8/2015 | Liang |
| 2015/0239937 | A1 | 8/2015 | Verdine et al. |
| 2015/0284437 | A1 | 10/2015 | Verdine et al. |
| 2015/0376227 | A1 | 12/2015 | Verdine et al. |
| 2016/0024153 | A1 | 1/2016 | Verdine et al. |

FOREIGN PATENT DOCUMENTS

| | | |
|---|---|---|
| EP | 09800675 | 12/2012 |
| EP | 10800148.8 | 10/2013 |
| WO | WO 96/02642 A1 | 2/1996 |
| WO | WO 96/20951 A1 | 7/1996 |
| WO | WO 96/34878 A1 | 11/1996 |
| WO | WO 00/06187 A2 | 2/2000 |
| WO | WO 02/064790 A2 | 8/2002 |
| WO | WO 03/106491 A2 | 12/2003 |
| WO | WO 2004/041275 A1 | 5/2004 |
| WO | WO 2004/058804 A1 | 7/2004 |
| WO | WO 2005/040202 A2 | 5/2005 |
| WO | WO 2005/040202 A3 | 5/2005 |
| WO | WO 2005/044839 A2 | 5/2005 |
| WO | WO 2005/044839 A3 | 5/2005 |
| WO | WO 2005/085457 A2 | 9/2005 |
| WO | WO 2005/090388 A1 | 9/2005 |
| WO | WO 2005/118620 A2 | 12/2005 |
| WO | WO 2005/118620 A3 | 12/2005 |
| WO | WO 2005/118634 A2 | 12/2005 |
| WO | WO 2005/118634 A3 | 12/2005 |
| WO | WO 2006/103666 A2 | 10/2006 |
| WO | WO 2007/141533 A2 | 12/2007 |
| WO | 2008/052580 | 5/2008 |
| WO | WO 2008/061192 A2 | 5/2008 |
| WO | WO 2008/095063 A1 | 8/2008 |
| WO | WO 2008/121767 A2 | 10/2008 |
| WO | 2008/058575 | 11/2008 |
| WO | WO 2009/042237 A2 | 4/2009 |
| WO | 2008/058575 | 10/2009 |
| WO | WO 2009/126292 A2 | 10/2009 |
| WO | WO 2010/011313 A2 | 1/2010 |
| WO | 2009/004260 | 3/2010 |
| WO | WO 2010/034029 A1 | 3/2010 |
| WO | WO 2010/068684 A2 | 6/2010 |
| WO | 2009/004260 | 10/2010 |
| WO | 2010/001952 | 10/2010 |
| WO | WO 2011/008260 A2 | 1/2011 |
| WO | 2009/004260 | 2/2011 |
| WO | 2010/001952 | 2/2011 |
| WO | 2010/001952 | 1/2012 |
| WO | 2011/052755 | 2/2012 |
| WO | WO 2012/040459 A2 | 3/2012 |
| WO | 2011/052755 | 4/2012 |
| WO | 2012/042738 | 10/2012 |
| WO | 2012/042719 | 11/2012 |
| WO | WO 2012/174423 A1 | 12/2012 |
| WO | 2011/052755 | 4/2013 |
| WO | 2012/042719 | 1/2014 |
| WO | 2012/042738 | 1/2014 |
| WO | 2013/062004 | 1/2014 |
| WO | 2013/062929 | 1/2014 |
| WO | 2013/062004 | 4/2014 |
| WO | WO 2014/052647 A2 | 4/2014 |
| WO | WO 2014/055564 A1 | 4/2014 |

OTHER PUBLICATIONS

Merck Manual Breast Cancer accessed Aug. 21, 2014 at URL: merckmanuals.com/home/womens_health_issues/breast_disorders/breast_cancer.html.*

Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html.*

International Preliminary Report on Patentability for PCT/US2013/062004, mailed Apr. 9, 2015.

International Preliminary Report on Patentability for PCT/US2013/062929, mailed Apr. 16, 2015.

International Search Report and Written Opinion for PCT/US2014/025544, mailed Sep. 10, 2014.

Invitation to Pay Additional Fees for PCT/US2014/025544, mailed Jul. 22, 2014.

International Search Report and Written Opinion for PCT/US2014/058680, mailed Apr. 23, 2015.

Extended European Search Report for EP 12800679.8, mailed Oct. 2, 2014.

Cox et al., Insulin receptor expression by human prostate cancers. Prostate. Jan. 1, 2009;69(1):33-40. Doi: 10.1002/pros.20852.

Duronio, Insulin receptor is phosphorylated in response to treatment of HepG2 cells with insulin-like growth factor I. Biochem J. Aug. 15, 1990;270(1):27-32.

Fustero et al., Asymmetric synthesis of new beta,beta-difluorinated cyclic quaternary alpha-amino acid derivatives. Org Lett. Aug. 31, 2006;8(18):4129-32.

Gupta et al., Long-term effects of tumor necrosis factor-alpha treatment on insulin signaling pathway in HepG2 cells and HepG2 cells overexpressing constitutively active Akt/PKB. J Cell Biochem. Feb. 15, 2007;100(3):593-607.

Moellering et al., Computational modeling and molecular optimization of stabilized alpha-helical peptides targeting NOTCH-CSL transcriptional complexes. European Journal of Cancer Supplements Nov. 2010; 8(7):30. DOI: 10.1016/S1359-6349(10)71774-2. Abstract 69.

Scott et al., Evidence of insulin-stimulated phosphorylation and activation of the mammalian target of rapamycin mediated by a protein kinase B signaling pathway. Proc Natl Acad Sci U S A. Jun. 23, 1998;95(13):7772-7.

Tsuruzoe et al., Insulin receptor substrate 3 (IRS-3) and IRS-4 impair IRS-1- and IRS-2-mediated signaling. Mol Cell Biol. Jan. 2001;21(1):26-38.

Ueki et al., Increased insulin sensitivity in mice lacking p85beta subunit of phosphoinositide 3-kinase. Proc Natl Acad Sci U S A. Jan. 8, 2002;99(1):419-24. Epub Dec. 18, 2001.

(56) References Cited

OTHER PUBLICATIONS

Ueki et al., Positive and negative regulation of phosphoinositide 3-kinase-dependent signaling pathways by three different gene products of the p85alpha regulatory subunit. Mol Cell Biol. Nov. 2000;20(21):8035-46.
Extended European Search Report for EP 10800148.8, mailed Oct. 16, 2013.
Invitation to Pay Additional Fees for PCT/US2010/001952, mailed Oct. 29, 2010.
International Search Report and Written Opinion for PCT/US2010/001952, mailed Feb. 2, 2011.
International Preliminary Report on Patentability for PCT/US2010/001952, mailed Jan. 26, 2012.
Extended European Search Report for EP 09800675.2, mailed Dec. 6, 2012.
Invitation to Pay Additional Fees for PCT/US2009/004260, mailed Mar. 19, 2010.
International Search Report and Written Opinion for PCT/US2009/004260, mailed Oct. 15, 2010.
International Preliminary Report on Patentability for PCT/US2009/004260, mailed Feb. 3, 2011.
Extended European Search Report for EP 12159110.1, mailed Jul. 20, 2012.
Extended European Search Report (Replacement Copy) for EP 12159110.1 mailed, Sep. 27, 2012.
International Search Report and Written Opinion for PCT/US2008/058575 mailed, Nov. 17, 2008.
International Preliminary Report on Patentability for PCT/US2008/058575 mailed, Oct. 8, 2009.
Invitation to Pay Additional Fees for PCT/US2011/052755, mailed Feb. 16, 2012.
International Search Report and Written Opinion for PCT/US2011/052755, mailed Apr. 25, 2012.
International Preliminary Report on Patentability for PCT/US2011/052755, mailed Apr. 4, 2013.
International Search Report and Written Opinion for PCT/US2012/042738, mailed Oct. 18, 2012.
International Preliminary Report on Patentability for PCT/US2012/042738, mailed Jan. 3, 2014.
Invitation to Pay Additional Fees for PCT/US2013/062004, mailed Jan. 2, 2014.
International Search Report and Written Opinion for PCT/US2013/062004, mailed Apr. 23, 2014.
International Search Report and Written Opinion for PCT/US2013/062929, mailed Jan. 30, 2014.
International Search Report and Written Opinion for PCT/US2012/042719, mailed Nov. 1, 2012.
International Preliminary Report on Patentability for PCT/US2012/042719, mailed Jan. 3, 2014.
International Search Report and Written Opinion for PCT/US2008/052580, mailed May 16, 2008.
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011; 80(4):305-318.
Andrews et al., Forming Stable Helical Peptides Using Natural and Artificial Amino Acids. Tetrahedron. 1999;55:11711-43.
Babine et al., Molecular Recognition of Proteinminus signLigand Complexes: Applications to Drug Design. Chem Rev. Aug. 5, 1997;97(5):1359-1472.
Biagini et al., Cross-metathesis of Unsaturated α-amino Acid Derivatives. J Chem Soc Perkin Trans. 1998;1:2485-99.
Bierzynski et al., A salt bridge stabilizes the helix formed by isolated C-peptide of Rnase A. Proc Natl Acad Sci U S A. Apr. 1982;79(8):2470-4.
Blackwell et al., Highly Efficient Synthesis of Covalently Cross-Linked Peptide Helices by Ring-Closing Metathesis. Angew Chem Int Ed. 1998;37(23):3281-84.
Blackwell et al., Ring-closing metathesis of olefinic peptides: design, synthesis, and structural characterization of macrocyclic helical peptides. J Org Chem. Aug. 10, 2001;66(16):5291-302.
Bode et al., Chemoselective amide ligations by decarboxylative condensations of Nalkylhydroxylamines and alpha-ketoacids. Angew Chem Int Ed Engl. Feb. 13, 2006;45(8):1248-52.
Bracken et al., Synthesis and Nuclear Magnetic Resonance Structure Determination of an α-Helical, Bicyclic, Lactam-Bridged Hexapeptide. J Am Chem Soc. 1994;116:6431-32.
Carlson et al., Specificity landscapes of DNA binding molecules elucidate biological function. Proc Natl Acad Sci U S A. Mar. 9, 2010;107(10):4544-9. doi: 10.1073/pnas.0914023107. Epub Feb. 22, 2010.
Chen et al., Determination of the helix and beta form of proteins in aqueous solution by circular dichroism. Biochemistry. Jul. 30, 1974;13(16):3350-9.
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Chia et al., Emerging roles for RAB family GTPases in human cancer. Biochim Biophys Acta. Apr. 2009;1795(2):110-6.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
David et al., Expressed protein ligation. Method and applications. Eur J Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Evans et al., The Rise of Azide-Alkyne 1,3-Dipolar 'Click' Cycloaddition and its Application to Polymer Science and Surface Modification. Australian Journal of Chemistry. 2007;60:384-95.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Fromme et al., Structural basis for removal of adenine mispaired with 8-oxoguanine by MutY adenine DNA glycosylase. Nature. Feb. 12, 2004;427(6975):652-6.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner et al., Mo[N(t-Bu)(Ar)]3 Complexes as Catalyst Precursors: in Situ Activation and Application to Metathesis Reactions of Alkynes and Diynes. J Am Chem Soc. 1999;121:9453-54.
Gallivan et al., A neutral, water-soluble olefin metathesis catalyst based on an N-heterocyclic carbene ligand. Tetrahedron Letters. 2005;46:2577-80.
Greenlee et al., A General Synthesis of α-vinyl-α-amino acids. Tetrahedron Letters 1978;42:3999-40002.
Grubbs et al., Ring-Closing Metathesis and Related Processes in Organic Synthesis. Acc Chem Res. 1995;28:446-52.
Guinn et al., Synthesis and characterization of polyamides containing unnatural amino acids. Biopolymers. May 1995;35(5):503-12.
Henchey et al., Contemporary strategies for the stabilization of peptides in the α-helical conformation. Curr Opin Chem Biol. 2008;12:692-97.
Holford et al., Adding 'splice' to protein engineering. Structure. Aug. 15, 1998;6(8):951-6.
Jackson et al., General Approach to the Synthesis of Short α-Helical Peptides. J Am Chem Soc. 1991;113:9391-92.
Junutula et al., Molecular characterization of Rab1 1 interactions with members of the family of Rab1 1-interacting proteins. J Biol Chem. Aug. 6, 2004;279(32):33430-7. Epub Jun. 1, 2004.

(56) References Cited

OTHER PUBLICATIONS

Karle et al., Structural characteristics of alpha-helical peptide molecules containing Aib residues. Biochemistry. Jul. 24, 1990;29(29):6747-56.

Karwoski et al., Lysinonorleucine cross-link formation in alpha amino heptenoic acid-substituted peptide derivatives. Biopolymers. 1978;17(5):1119-27.

Kaul et al., Stereochemical control of peptide folding. Bioorg Med Chem. Jan. 1999;7(1):105-17.

Kazmaier, Sythesis of Quaternary Amino Acids Containing β, γ- as well as γ,δ-Unsaturated Side Chains via Chelate-Enolate Claisen Rearrangement. Tetrahedron Letters. 1996;37(30):5351-4.

Khalil et al., An efficient and high yield method for the N-tert-butoxycarbonyl protection of sterically hindered amino acids. Tetrahedron Lett. 1996;37(20):3441-44.

Kim et al., Introduction of all-hydrocarbon i,i+3 staples into alpha-helices via ring-closing olefin metathesis. Org Lett. Jul. 2, 2010;12(13):3046-9. doi: 10.1021/ol1010449.

Kim et al., Stereochemical effects of all-hydrocarbon tethers in i,i∝stapled peptides. Bioorg Med Chem Lett. May 1, 2009;19(9):2533-6. Epub Mar. 13, 2009.

Kim et al., Synthesis of all-hydrocarbon stapled α-helical peptides by ring-closing olefin metathesis. Nat Protoc. Jun. 2011;6(6):761-71. doi: 10.1038/nprot.2011.324. Epub May 12, 2011.

Kimmerlin et al., '100 years of peptide synthesis': ligation methods for peptide and protein synthesis with applications to beta-peptide assemblies. J Pept Res. Feb. 2005;65(2):229-60.

Kohler et al., DNA specificity enhanced by sequential binding of protein monomers. Proc Natl Acad Sci U S A. Oct. 12, 1999;96(21):11735-9.

Kolb et al., Click Chemistry: Diverse Chemical Function from a Few Good Reactions. Angew Chem Int Ed Engl. Jun. 1, 2001;40(11):2004-2021.

Kotha et al., Modification of constrained peptides by ring-closing metathesis reaction. Bioorg Med Chem Lett. Jun. 4, 2001;11(11):1421-3.

Kutchukian et al., All-atom model for stabilization of alpha-helical structure in peptides by hydrocarbon staples. J Am Chem Soc. Apr. 8, 2009;131(13):4622-7.

Liskamp, Conformationally restricted amino acids and dipeptides, (non)peptidomimetics and secondary structure mimetics. Red Travl Chim Pays-Bas. 1994;113:1-19.

MacMillan, Evolving strategies for protein synthesis converge on native chemical ligation Angew Chem Int Ed Engl. Nov. 27, 2006;45(46):7668-72.

McNamara et al., Peptides constrained by an aliphatic linkage between two C(alpha) sites: design, synthesis, and unexpected conformational properties of an i,(i + 4)-linked peptide. J Org Chem. Jun. 29, 2001;66(13):4585-94.

Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.

Miller et al., Application of Ring-Closing Metathesis to the Synthesis of Rigidified Amino Acids and Peptides. J Am Chem Soc. 1996;118(40):9606-9614.

Miller et al., Synthesis of Conformationally Restricted Amino Acids and Peptides Employing Olefin Metathesis. J Am Chem Soc. 1995;117(21):5855-5856.

Moellering et al., Direct inhibition of the NOTCH transcription factor complex. Nature. Nov. 12, 2009;462(7270):182-8.

Muir et al., Expressed protein ligation: a general method for protein engineering. Proc Natl Acad Sci U S A. Jun. 9, 1998;95(12):6705-10.

Muir, Semisynthesis of proteins by expressed protein ligation. Annu Rev Biochem. 2003;72:249-89. Epub Feb. 27, 2003.

Pellois et al., Semisynthetic proteins in mechanistic studies: using chemistry to go where nature can't. Curr Opin Chem Biol. Oct. 2006;10(5):487-91. Epub Aug. 28, 2006.

Phelan et al., A General Method for Constraining Short Peptides to an α-Helical Conformation. J Am Chem Soc. 1997;119(3):455-60.

Robert, A hierarchical "nesting" approach to describe the stability of alpha helices with side-chain interactions. Biopolymers. 1990;30(3-4):335-47.

Roos et al., Synthesis of α-Substituted α-Amino Acids via Cationic Intermediates, J Org Chem. 1993;58:3259-68.

Sali et al., Stabilization of protein structure by interaction of alpha-helix dipole with a charged side chain. Nature. Oct. 20, 1988;335(6192):740-3.

Schafmiester et al., An All-Hydrocarbon Cross-Linking System for Enhancing the Helicity and Metabolic Stability of Peptides. J Am Chem Soc. 2000;122:5891-92.

Scheffzek et al., The Ras-RasGAP complex: structural basis for GTPase activation and its loss in oncogenic Ras mutants. Science. Jul. 18, 1997;277(5324):333-8.

Schmiedeberg et al., Reversible backbone protection enables combinatorial solid-phase ring-closing metathesis reaction (RCM) in peptides. Org Lett Jan. 10, 2002;4(1):59-62.

Scholtz et al., The mechanismof alha-helix formation by peptides. Annu Rev Biomol Struct. 1992;21:95-118.

Schwarzer et al., Protein semisynthesis and expresses protein ligation: chasing a protein's tail. Curr Opin Chem Biol. Dec. 2005;9(6):561-9. Epub Oct. 13, 2005.

Seabra et al., Rab GTPases, intracellular traffic and disease. Trends Mol Med. Jan. 2002;8(1):23-30.

Shiba et al., Structural basis for Rab 11-dependent membrane recruitment of a family of Rab11-interacting protein 3 (FIP3)/Arfophilin-1. Proc Natl Acad Sci U S A. Oct. 17, 2006;103(42):15416-21. Epub Oct. 9, 2006.

Stein et al., Rab proteins and endocytic trafficking: potential targets for therapeutic intervention. Adv Drug Deliv Rev. Nov. 14, 2003;55(11):1421-37.

Stenmark et al., The Rab GTPase family. Genome Biol. 2001;2(5):3007.1-3007.7.

Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.

Tanaka, Design and synthesis of non-proteingenic amino acids and secondary structures of their peptides. Yakugaku Zasshi. Oct. 2006;126(10):931-44. Japanese.

Toniolo, Conformationally restricted peptides through short-range cyclizations. Int J Pept Protein Res. Apr. 1990;35(4):287-300.

Tornøe et al., Peptidotriazoles on solid phase: [1,2,3]-triazoles by regiospecific copper(i)-catalyzed 1,3-dipolar cycloadditions of terminal alkynes to azides. J org Chem. May 3, 2002;67(9):3057-64.

Verdine at al., Stapled peptides for intracelluar drug targets. Methods Enzymol. 2012;503:3-33. doi: 10.1016/B978-0-12-396962-0.00001-X.

Verdine et al., The challenge of drugging undruggable targets in cancer: lessons learned from targeting BCL-2 family members. Clin Cancer Res. Dec. 15, 2007;13(24):7264-70.

Wei et al., Disorder and structure in the Rab11 binding domain of Rab11 family interacting protein 2. Biochemistry. Jan. 27, 2009;48(3):549-57. doi: 10.1021/bi8020197.

Williams et al., Asymmetric Synthesis of Monosubstituted and α,α-Disubstituted α-Amino Acids via Diastereoselective Glycine Enolate Alkylations. J Am Chem Soc. 1991;113:9276-86.

Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.

Zimm et al., Theory of the Phase Transition between Helix and Random Coil in Polypeptide Chains. J Chem Phys. 1959;31:526-35.

Zor et al., Solution structure of the KIX domain of CBP bound to the transactivation domain of c-Myb. J Mol Biol. Mar. 26, 2004;337(3):521-34.

U.S. Appl. No. 14/880,080, filed Oct. 9, 2015, Verdine et al.
U.S. Appl. No. 14/748,287, filed Jun. 24, 2015, Verdine et al.
U.S. Appl. No. 14/775,315, filed Sep. 11, 2015, Verdine et al.
U.S. Appl. No. 14/898,222, filed Dec. 14, 2015, Verdine et al.
U.S. Appl. No. 14/896,132, filed Dec. 4, 2015, Palchaudhuri et al.

(56) References Cited

OTHER PUBLICATIONS

PCT/US2014/025544, Sep. 24, 2015, International Preliminary Report on Patentability.
PCT/US2014/042329, Nov. 24, 2014, International Search Report and Written Opinion.
PCT/US2014/042329, Dec. 23, 2015, International Preliminary Report on Patentability.
PCT/US2014/041338, Nov. 10, 2014, International Preliminary Report on Patentability.
PCT/US2014/041338, Dec. 17, 2015, International Preliminary Report on Patentability.
International Preliminary Report on Patentability for PCT/US2014/025544, mailed Sep. 24, 2015.
International Search Report and Written Opinion for PCT/US2014/042329, mailed Nov. 24, 2014.
International Preliminary Report on Patentability for PCT/US2014/042329, mailed Dec. 23, 2015.
International Search Report and Written Opinion for PCT/US2014/041338, mailed Nov. 10, 2014.
International Preliminary Report on Patentability for PCT/US2014/041338, mailed Dec. 17, 2015.
[No Author Listed] Brain Tumors. Merck Manuals. Aug. 21, 2014. merckmanuals.com/home/brain_spinal_cord_and_nerve_disorders/tumors_of_the_nervous_system/brain_tumors.html. 9 pages.
[No Author Listed] Overview of Leukemia. Merck Manuals. Aug. 20, 2014. merckmanuals.com/home/blood_disorders/leukemias/overview_of_leukemia.html?qt=Leukemia&alt=sh. 2 pages.
[No Author Listed] Colorectal Cancer. Merck Manuals. Aug. 21, 2014. merckmanuals.com/home/digestive_disorders/tumors_of_the_digestive_system/colorectal_cancer. html. 5 pages.
[No Author Listed] Prostate Cancer. Merck Manuals. Aug. 21, 2014. merckmanuals.com/home/kidney_and_urinary_tract_disorders/cancers_of_the_kidney_and_genitourinary_tract/prostate_cancer.html?qt=prostatecancer&alt=sh. 8 pages.
[No Author Listed] Breast Cancer. Merck Manuals. Aug. 21, 2014. merckmanuals.com/home/womens_health_issues/breast_disorders/breast_cancer.html. 20 pages.
[No Author Listed] Bladder Cancer. Merck Manuals. Aug. 21, 2014. merckmanuals.com/home/kidney_and_urinary_tract_disorders/cancers_of_the_kidney_and_genitourinary_tract/bladder_cancer.html. 2 pages.
Friedman-Einat et al., Target gene identification: target specific transcriptional activation by three murine homeodomain/VP16 hybrid proteins in *Saccharomyces cerevisiae*. J Exp Zool. Feb. 15, 1996;274(3):145-56.
Lindsay et al., Rab coupling protein (RCP), a novel Rab4 and Rab11 effector protein. J Biol Chem. Apr. 5, 2002;277(14):12190-9. Epub Jan. 10, 2002.
Lomar et al., Synthese symmetrischerf ketone unter verwendung von 2-Phenyl-2-oxazolin-5-on. Chemische Berichte. 1980;113(12):3706-15.
Lu et al., Both Pbxl and E2A-Pbx1 bind the DNA motif ATCAATCAA cooperatively with the products of multiple murine Hox genes, some of which are themselves oncogenes. Mol Cell Biol. Jul. 1995;15(7):3786-95.
Lu et al., Structural determinants within Pbxl that mediate cooperative DNA binding with pentapeptide-containing Hox proteins: proposal for a model of a Pbxl-Hox-DNA complex. Mol Cell Biol. Apr. 1996;16(4):1632-40.
Palchaudhuri et al., Differentiation induction in acute myeloid leukemia using site-specific DNA-targeting. 55th ASH Annual Meeting and Exposition. Dec. 9, 2013. Accessed at https://ash.confex.com/ash/2013/webprogram/Paper60843.html.
U.S. Appl. No. 13/383,881, filed Jan. 13, 2012, Verdine et al.
U.S. Appl. No. 13/055,279, filed Jan. 21, 2011, Verdine et al.
U.S. Appl. No. 12/593,384, filed Mar. 5, 2010, Verdine et al.
U.S. Appl. No. 14/027,064, filed Sep. 13, 2013, Verdine et al.
U.S. Appl. No. 13/825,709, filed Mar. 22, 2013, Verdine et al.
U.S. Appl. No. 14/127,039, filed Dec. 17, 2013, Moellering et al.
U.S. Appl. No. 09/574,086, filed May 18, 2000, Verdine et al.
U.S. Appl. No. 11/148,976, filed Jun. 9, 2005, Verdine et al.
U.S. Appl. No. 12/796,212, filed Jun. 8, 2010, Verdine et al.
U.S. Appl. No. 13/680,905, filed Nov. 19, 2012, Verdine et al.
U.S. Appl. No. 14/068,844, filed Oct. 31, 2013, Verdine et al.
U.S. Appl. No. 12/420,816, filed Apr. 8, 2009, Nash et al.
U.S. Appl. No. 13/570,146, filed Aug. 8, 2012, Nash et al.
U.S. Appl. No. 14/156,350, filed Jan. 15, 2014, Nash et al.

* cited by examiner

Figure 1
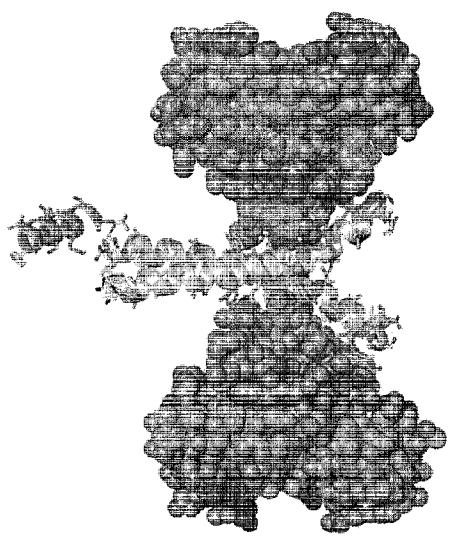
Shiba T et al., PNAS, 2006
PDB: 1OIV, 1OIW
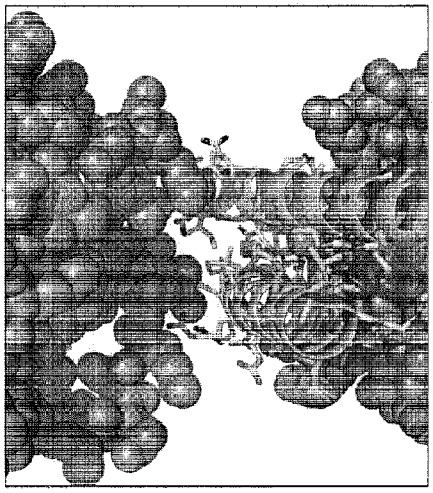
FIP'-FIP/RAB'-FIP contacts
RAB-FIP contacts

A $S_5$-staple positions

| Residues | | | | | | | | | | | | | | | | | | | | | | | | | | | | | | | | CHARGE |
|---|---|---|---|---|---|---|---|---|---|---|---|---|---|---|---|---|---|---|---|---|---|---|---|---|---|---|---|---|---|---|---|---|
| | WT | | | # | # | # | # | # | * | * | | | | | | | * | * | * | | | | ^ ^ | | | ^ ^ | ^ ^ | ~ ~ | * | | | |
| 1243-1274 | Fip1 | K | K | E | F | Q | V | R | E | L | E | D | Y | I | D | N | L | V | R | V | M | E | E | T | P | N | I | L | R | I | P A | -1 |
| 469-500 | Fip2 | E | R | D | T | H | I | R | E | L | E | D | Y | I | D | N | L | V | R | V | M | E | E | T | P | S | I | L | R | V | P Y | -1 |
| 726-756 | Fip3 | K | Q | E | E | I | N | F | R | L | Q | D | Y | I | D | R | I | V | A | I | M | E | T | N | P | S | I | L | E | V | K | 0 |
| 606-637 | Fip4 | E | Q | E | E | I | N | F | R | L | R | Q | Y | M | D | K | I | L | A | I | L | D | H | N | P | S | I | L | E | I | K H | 1 |
| | | 1 | | | | 5 | | | | | 10 | | | | | 15 | | | | | 20 | | | | | 25 | | | | | 30 | | |

^ Packing/folding
\* critical Rab binding
~ Rab binding
\# Fip dimer or Rab' binding

B

"IIV"    "IME"    "IDR"    "YID"

Figure 4

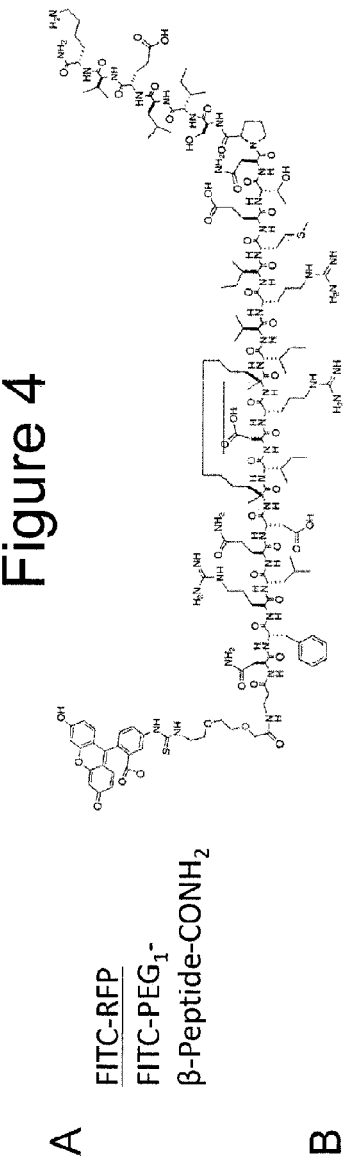

| | | | | | | | | | | | | | | | | | Rab11 $K_D$ (uM) | Rab25 $K_D$ (uM) |
|---|---|---|---|---|---|---|---|---|---|---|---|---|---|---|---|---|---|---|
| Fip1 | | | | | | | | | | | | | | | | | | |
| RFP6 | β | R | Q | V | R | E | L | E | S5 | Y | I | D | S5 | L | L | V | R | V | M | E | E | T | P | N | I | L | R | I | P | R | - | 0 | >5 | >5 |
| RFP7 | β | R | Q | V | R | E | L | E | D | Y | I | D | S5 | L | L | V | S5 | V | M | E | E | T | P | N | I | L | R | I | P | R | - | 2 | 0.114 | 0.67 |
| RFP8 | β | R | Q | V | R | E | L | E | D | Y | I | D | N | L | L | V | S5 | V | M | E | S5 | T | P | N | I | L | R | I | P | R | - | 1 | 0.039 | 0.78 |
| RFP9 | β | R | Q | V | R | E | L | E | D | N | S5 | I | D | S5 | L | L | V | R | V | M | E | E | T | P | N | I | L | R | I | P | R | - | 1 | 2.34 | 1.5 |
| Fip3 | | | | | | | | | | | | | | | | | | |
| RFP10 | β | R | I | N | F | R | L | Q | S5 | Y | I | D | S5 | I | I | V | R | I | M | E | T | N | P | S | I | L | E | V | K | | + | 1 | >5 | >5 |
| RFP11 | β | R | I | N | F | R | L | Q | D | Y | I | D | S5 | I | I | V | S5 | I | M | E | T | N | P | S | I | L | E | V | K | | - | 1 | 0.01 | 0.06 |
| RFP12 | β | R | I | N | F | R | L | Q | D | Y | I | D | R | I | I | V | S5 | I | M | E | S5 | N | P | S | I | L | E | V | K | | | 0 | 0.015 | 0.18 |
| RFP13 | β | R | I | N | F | R | L | Q | D | S5 | I | D | R | I | I | V | R | I | M | E | T | N | P | S | I | L | E | V | K | | + | 1 | 0.093 | 0.4 |
| RFP1 | β | N | F | R | L | Q | D | Y | I | D | R | I | I | V | A | I | M | E | T | N | P | S | I | L | E | V | K | | | | | | 1.7 | >5 |
| RFP1-OX | β | N | F | R | L | Q | D | Y | I | D | R | I | I | V | A | I | $M_O$ | E | T | N | P | S | I | L | E | V | K | | | | | | 8.1 | >5 |

FITC-RFP
FITC-PEG$_1$-
β-Peptide-CONH$_2$

Figure 7

| | Sequence | Charge | Rab11 $K_D$ (uM) | Rab25 $K_D$ (uM) |
|---|---|---|---|---|
| RFP14 | βRQVRELENYIDRLLVSVNLESTPNILRIPR | +1 | 0.01 | 0.05 |
| RFP15 | βRINFRLQNYIDSIIVSINLETNPSILRVK | +2 | 0.01 | >5 |
| RFP16 | βRINFRLQNSIDRSSIVRINLETNPSILEVK | +2 | 0.05 | 0.09 |
| RFP17 | βRINFRLQNSIDRSSIVRIFETNPSILEVK | +2 | 0.06 | 0.06 |
| RFP18 | βRINFRLQNYIDSIIVSIFETNPSILRVK | +2 | 0.02 | >5 |
| RFP19 | βRINFDLQNYIRSIIVSINLETNPSILRVK | +2 | >5 | >5 |
| RFP20 | βRINFDLQNYIRSIIVSIAETNPSILRVK | +2 | 0.32 | 0.1 |

SEQUENCE LISTING

```
<160> NUMBER OF SEQ ID NOS: 87

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1
```

Lys Lys Glu Phe
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Glu Arg Asp Thr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Lys Gln Glu Glu
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Glu Gln Glu Glu
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Ile Asn Phe Arg
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

His Ile Arg Glu
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Arg Glu Leu Glu

-continued

```
<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 8

Phe Arg Leu Arg
1

<210> SEQ ID NO 9
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X = D, Q, or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (8)..(8)
<223> OTHER INFORMATION: X = Y or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (11)..(11)
<223> OTHER INFORMATION: X = N, R, K, amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (12)..(12)
<223> OTHER INFORMATION: X = L, I or amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (15)..(15)
<223> OTHER INFORMATION: X = R, A or amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (19)..(19)
<223> OTHER INFORMATION: X = E, T, H or amino acid of formula (i) with
      an alkenyl side chain as shown on page 40, or a stapled derivative
      thereof as shown on page 44 of specification

<400> SEQUENCE: 9

Gln Val Arg Glu Leu Glu Xaa Xaa Ile Asp Xaa Xaa Leu Val Xaa Val
1               5                   10                  15

Met Glu Xaa Thr Pro Asn Ile Leu Arg Ile
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
```

```
<222> LOCATION: (7)..(7)
<223> OTHER INFORMATION: X = D, Q or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (8)..(8)
<223> OTHER INFORMATION: X = Y or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (11)..(11)
<223> OTHER INFORMATION: X = N, R, K, amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (12)..(12)
<223> OTHER INFORMATION: X = L, I or amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (15)..(15)
<223> OTHER INFORMATION: X = R, A or amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (19)..(19)
<223> OTHER INFORMATION: X = E, T, H or amino acid of formula (i) with
      an alkenyl side chain as shown on page 40, or a stapled derivative
      thereof as shown on page 44 of specification

<400> SEQUENCE: 10

His Ile Arg Glu Leu Glu Xaa Xaa Ile Asp Xaa Xaa Leu Val Xaa Val
1               5                   10                  15

Met Glu Xaa Thr Pro Ser Ile Leu Arg Val
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X = D, Q or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (8)..(8)
<223> OTHER INFORMATION: X = Y or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (11)..(11)
<223> OTHER INFORMATION: X = N, R, K, amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (12)..(12)
<223> OTHER INFORMATION: X = L, I or amino acid of formula (i) with an
      alkenyl side chain or formula (ii) with a dialkenyl side chain
      shown on page 40, or a stapled derivative thereof shown on page 44
      of specification
```

```
<220> FEATURE:
<221> NAME/KEY: MOD_RES
<222> LOCATION: (15)..(15)
<223> OTHER INFORMATION: X = R, A or amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (19)..(19)
<223> OTHER INFORMATION: X = E, T, H or amino acid of formula (i) with
      an alkenyl side chain as shown on page 40, or a stapled derivative
      thereof as shown on page 44 of specification

<400> SEQUENCE: 11

Ile Asn Phe Arg Leu Gln Xaa Xaa Ile Asp Xaa Xaa Ile Val Xaa Ile
1               5                   10                  15

Met Glu Xaa Asn Pro Ser Ile Leu Glu Val
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X = D, Q or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (8)..(8)
<223> OTHER INFORMATION: X = Y or amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (11)..(11)
<223> OTHER INFORMATION: X = N, R, K, amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (12)..(12)
<223> OTHER INFORMATION: X = L, I or amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (15)..(15)
<223> OTHER INFORMATION: X = R, A or amino acid of formula (i) with an
      alkenyl side chain or formula (ii) with a dialkenyl side chain
      shown on page 40, or a stapled derivative thereof shown on page 44
      of specification
<220> FEATURE:
<221> NAME/KEY: MOD_RES
<222> LOCATION: (19)..(19)
<223> OTHER INFORMATION: X = E, T, H, amino acid of formula (i) with an
      alkenyl side chain as shown on page 40, or a stapled derivative
      thereof as shown on page 44 of specification

<400> SEQUENCE: 12

Ile Asn Phe Arg Leu Arg Xaa Xaa Met Asp Xaa Xaa Ile Leu Xaa Ile
1               5                   10                  15

Leu Asp Xaa Asn Pro Ser Ile Leu Glu Ile
            20                  25

<210> SEQ ID NO 13
```

```
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is an amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (11)..(11)
<223> OTHER INFORMATION: X is an amino acid of formula (i) with an
      alkenyl side chain as shown on page 40, or a stapled derivative
      thereof as shown on page 44 of specification

<400> SEQUENCE: 13

Gln Val Arg Glu Leu Glu Xaa Tyr Ile Asp Xaa Leu Leu Val Arg Val
1               5                   10                  15

Met Glu Glu Thr Pro Asn Ile Leu Arg Ile
            20                  25

<210> SEQ ID NO 14
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is an amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (12)..(12)
<223> OTHER INFORMATION: X is an amino acid of formula (i) with an
      alkenyl side chain as shown on page 40, or a stapled derivative
      thereof as shown on page 44 of specification

<400> SEQUENCE: 14

Gln Val Arg Glu Leu Glu Asp Xaa Ile Asp Asn Xaa Leu Val Arg Val
1               5                   10                  15

Met Glu Glu Thr Pro Asn Ile Leu Arg Ile
            20                  25

<210> SEQ ID NO 15
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is an amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (15)..(15)
<223> OTHER INFORMATION: X is an amino acid of formula (i) with an
      alkenyl side chain as shown on page 40, or a stapled derivative
      thereof as shown on page 44 of specification

<400> SEQUENCE: 15

Gln Val Arg Glu Leu Glu Asp Tyr Ile Asp Xaa Leu Leu Val Xaa Val
1               5                   10                  15
```

```
Met Glu Glu Thr Pro Asn Ile Leu Arg Ile
            20                  25

<210> SEQ ID NO 16
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: X is an amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (19)..(19)
<223> OTHER INFORMATION: X is an amino acid of formula (i) with an
      alkenyl side chain as shown on page 40, or a stapled derivative
      thereof as shown on page 44 of specification

<400> SEQUENCE: 16

Gln Val Arg Glu Leu Glu Asp Tyr Ile Asp Asn Leu Leu Val Xaa Val
1               5                   10                  15

Met Glu Xaa Thr Pro Asn Ile Leu Arg Ile
            20                  25

<210> SEQ ID NO 17
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is an amino acid of formula (i) with an
      alkenyl side chain as shown on page 40, or a stapled derivative
      thereof as shown on page 44 of specification
<220> FEATURE:
<221> NAME/KEY: MOD_RES
<222> LOCATION: (11)..(11)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (15)..(15)
<223> OTHER INFORMATION: X is an amino acid of formula (i) with an
      alkenyl side chain as shown on page 40, or a stapled derivative
      thereof as shown on page 44 of specification

<400> SEQUENCE: 17

Gln Val Arg Glu Leu Glu Xaa Tyr Ile Asp Xaa Leu Leu Val Xaa Val
1               5                   10                  15

Met Glu Glu Thr Pro Asn Ile Leu Arg Ile
            20                  25

<210> SEQ ID NO 18
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification
<220> FEATURE:
```

-continued

```
<221> NAME/KEY: MOD_RES
<222> LOCATION: (15)..(15)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (19)..(19)
<223> OTHER INFORMATION: X is amino acid of formula (i) with an alkenyl
      side chain as shown on page 40, or a stapled derivative thereof as
      shown on page 44 of specification

<400> SEQUENCE: 18

Gln Val Arg Glu Leu Glu Asp Tyr Ile Asp Xaa Leu Leu Val Xaa Val
1               5                   10                  15

Met Glu Xaa Thr Pro Asn Ile Leu Arg Ile
            20                  25

<210> SEQ ID NO 19
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification

<400> SEQUENCE: 19

His Ile Arg Glu Leu Glu Xaa Tyr Ile Asp Xaa Leu Leu Val Arg Val
1               5                   10                  15

Met Glu Glu Thr Pro Ser Ile Leu Arg Val
            20                  25

<210> SEQ ID NO 20
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (12)..(12)
<223> OTHER INFORMATION: X is amino acid of formula (i) with an alkenyl
      side chain as shown on page 40, or a stapled derivative thereof as
      shown on page 44 of specification

<400> SEQUENCE: 20

His Ile Arg Glu Leu Glu Asp Xaa Ile Asp Asn Xaa Leu Val Arg Val
1               5                   10                  15

Met Glu Glu Thr Pro Ser Ile Leu Arg Val
            20                  25

<210> SEQ ID NO 21
<211> LENGTH: 26
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification

<400> SEQUENCE: 21

His Ile Arg Glu Leu Glu Asp Tyr Ile Asp Xaa Leu Leu Val Xaa Val
1               5                   10                  15

Met Glu Arg Thr Pro Ser Ile Leu Arg Val
            20                  25

<210> SEQ ID NO 22
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (19)..(19)
<223> OTHER INFORMATION: X is amino acid of formula (i) with an alkenyl
      side chain as shown on page 40, or a stapled derivative thereof as
      shown on page 44 of specification

<400> SEQUENCE: 22

His Ile Arg Glu Leu Glu Asp Tyr Ile Asp Asn Leu Leu Val Xaa Val
1               5                   10                  15

Met Glu Xaa Thr Pro Ser Ile Leu Arg Val
            20                  25

<210> SEQ ID NO 23
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (11)..(11)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification
```

```
<400> SEQUENCE: 23

His Ile Arg Glu Leu Glu Xaa Tyr Ile Asp Xaa Leu Leu Val Xaa Val
1               5                   10                  15

Met Glu Glu Thr Pro Ser Ile Leu Arg Val
            20                  25

<210> SEQ ID NO 24
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (15)..(15)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (19)..(19)
<223> OTHER INFORMATION: X is amino acid of formula (i) with an alkenyl
      side chain as shown on page 40, or a stapled derivative thereof as
      shown on page 44 of specification

<400> SEQUENCE: 24

His Ile Arg Glu Leu Glu Asp Tyr Ile Asp Xaa Leu Leu Val Xaa Val
1               5                   10                  15

Met Glu Xaa Thr Pro Ser Ile Leu Arg Val
            20                  25

<210> SEQ ID NO 25
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification

<400> SEQUENCE: 25

Ile Asn Phe Arg Leu Gln Xaa Tyr Ile Asp Xaa Ile Ile Val Ala Ile
1               5                   10                  15

Met Glu Thr Asn Pro Ser Ile Leu Glu Val
            20                  25

<210> SEQ ID NO 26
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
```

```
<222> LOCATION: (8)..(8)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (12)..(12)
<223> OTHER INFORMATION: X is amino acid of formula (i) with an alkenyl
      side chain as shown on page 40, or a stapled derivative thereof as
      shown on page 44 of specification

<400> SEQUENCE: 26

Ile Asn Phe Arg Leu Gln Asp Xaa Ile Asp Arg Xaa Ile Val Ala Ile
1               5                  10                  15

Met Glu Thr Asn Pro Ser Ile Leu Glu Val
            20                  25

<210> SEQ ID NO 27
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification

<400> SEQUENCE: 27

Ile Asn Phe Arg Leu Gln Asp Tyr Ile Asp Xaa Ile Ile Val Xaa Ile
1               5                  10                  15

Met Glu Thr Asn Pro Ser Ile Leu Glu Val
            20                  25

<210> SEQ ID NO 28
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (19)..(19)
<223> OTHER INFORMATION: X is amino acid of formula (i) with an alkenyl
      side chain as shown on page 40, or a stapled derivative thereof as
      shown on page 44 of specification

<400> SEQUENCE: 28

Ile Asn Phe Arg Leu Gln Asp Tyr Ile Asp Arg Ile Ile Val Xaa Ile
1               5                  10                  15

Met Glu Xaa Asn Pro Ser Ile Leu Glu Val
            20                  25

<210> SEQ ID NO 29
<211> LENGTH: 26
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (11)..(11)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification

<400> SEQUENCE: 29

Ile Asn Phe Arg Leu Gln Xaa Tyr Ile Asp Xaa Ile Ile Val Xaa Ile
1               5                   10                  15

Met Glu Thr Asn Pro Ser Ile Leu Glu Val
            20                  25

<210> SEQ ID NO 30
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (15)..(15)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (19)..(19)
<223> OTHER INFORMATION: X is amino acid of formula (i) with an alkenyl
      side chain as shown on page 40, or a stapled derivative thereof as
      shown on page 44 of specification

<400> SEQUENCE: 30

Ile Asn Phe Arg Leu Gln Asp Tyr Ile Asp Xaa Ile Ile Val Xaa Ile
1               5                   10                  15

Met Glu Xaa Asn Pro Ser Ile Leu Glu Val
            20                  25

<210> SEQ ID NO 31
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
```

```
<222> LOCATION: (11)..(11)
<223> OTHER INFORMATION: X is amino acid of formula (i) with an alkenyl
      side chain as shown on page 40, or a stapled derivative thereof as
      shown on page 44 of specification

<400> SEQUENCE: 31

Ile Asn Phe Arg Leu Arg Xaa Tyr Met Asp Xaa Ile Ile Leu Ala Ile
1               5                   10                  15

Leu Asp His Asn Pro Ser Ile Leu Glu Ile
            20                  25

<210> SEQ ID NO 32
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (12)..(12)
<223> OTHER INFORMATION: X is amino acid of formula (i) with an alkenyl
      side chain as shown on page 40, or a stapled derivative thereof as
      shown on page 44 of specification

<400> SEQUENCE: 32

Ile Asn Phe Arg Leu Arg Gln Xaa Met Asp Lys Xaa Ile Leu Ala Ile
1               5                   10                  15

Leu Asp His Asn Pro Ser Ile Leu Glu Ile
            20                  25

<210> SEQ ID NO 33
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification

<400> SEQUENCE: 33

Ile Asn Phe Arg Leu Arg Gln Tyr Met Asp Xaa Ile Ile Leu Xaa Ile
1               5                   10                  15

Leu Asp His Asn Pro Ser Ile Leu Glu Ile
            20                  25

<210> SEQ ID NO 34
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
```

```
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (19)..(19)
<223> OTHER INFORMATION: X is amino acid of formula (i) with an alkenyl
      side chain as shown on page 40, or a stapled derivative thereof as
      shown on page 44 of specification

<400> SEQUENCE: 34

Ile Asn Phe Arg Leu Arg Gln Tyr Met Asp Lys Ile Ile Leu Xaa Ile
1               5                   10                  15

Leu Asp Xaa Asn Pro Ser Ile Leu Glu Ile
            20                  25

<210> SEQ ID NO 35
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (11)..(11)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (15)..(15)
<223> OTHER INFORMATION: X is amino acid of formula (i) with an alkenyl
      side chain as shown on page 40, or a stapled derivative thereof as
      shown on page 44 of specification

<400> SEQUENCE: 35

Ile Asn Phe Arg Leu Arg Xaa Tyr Met Asp Xaa Ile Ile Leu Xaa Ile
1               5                   10                  15

Leu Asp His Asn Pro Ser Ile Leu Glu Ile
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula (i) with an alkenyl
      side chain as shown on page 40, or a stapled derivative thereof as
      shown on page 44 of specification
<220> FEATURE:
<221> NAME/KEY: MOD_RES
<222> LOCATION: (15)..(15)
<223> OTHER INFORMATION: X is amino acid of formula (ii) with a
      dialkenyl side chain shown on page 40, or a stapled derivative
      thereof shown on page 44 of specification
<220> FEATURE:
<221> NAME/KEY: MOD_RES
<222> LOCATION: (19)..(19)
<223> OTHER INFORMATION: X is amino acid of formula (i) with an alkenyl
      side chain as shown on page 40, or a stapled derivative thereof as
      shown on page 44 of specification

<400> SEQUENCE: 36
```

```
Ile Asn Phe Arg Leu Arg Gln Tyr Met Asp Xaa Ile Ile Leu Xaa Ile
1               5                   10                  15

Leu Asp Xaa Asn Pro Ser Ile Leu Glu Ile
            20                  25

<210> SEQ ID NO 37
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof

<400> SEQUENCE: 37

Gln Val Arg Glu Leu Glu Xaa Tyr Ile Asp Xaa Leu Leu Val Arg Val
1               5                   10                  15

Met Glu Glu Thr Pro Asn Ile Leu Arg Ile
            20                  25

<210> SEQ ID NO 38
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (12)..(12)
<223> OTHER INFORMATION: X is amino acid of formula A5 with a methyl and
      a pentenyl side chain as shown on page 42 of specification, or a
      stapled derivative thereof

<400> SEQUENCE: 38

Gln Val Arg Glu Leu Glu Asp Xaa Ile Asp Asn Xaa Leu Val Arg Val
1               5                   10                  15

Met Glu Glu Thr Pro Asn Ile Leu Arg Ile
            20                  25

<210> SEQ ID NO 39
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (15)..(15)
```

```
<223> OTHER INFORMATION: X is amino acid of formula A5 with a methyl and
      a pentenyl side chain as shown on page 42 of specification, or a
      stapled derivative thereof

<400> SEQUENCE: 39

Gln Val Arg Glu Leu Glu Asp Tyr Ile Asp Xaa Leu Leu Val Xaa Val
1               5                   10                  15

Met Glu Glu Thr Pro Asn Ile Leu Arg Ile
            20                  25

<210> SEQ ID NO 40
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (19)..(19)
<223> OTHER INFORMATION: X is amino acid of formula A5 with a methyl and
      a pentenyl side chain as shown on page 42 of specification, or a
      stapled derivative thereof

<400> SEQUENCE: 40

Gln Val Arg Glu Leu Glu Asp Tyr Ile Asp Asn Leu Leu Val Xaa Val
1               5                   10                  15

Met Glu Xaa Thr Pro Asn Ile Leu Arg Ile
            20                  25

<210> SEQ ID NO 41
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof

<400> SEQUENCE: 41

His Ile Arg Glu Leu Glu Xaa Tyr Ile Asp Xaa Leu Leu Val Arg Val
1               5                   10                  15

Met Glu Glu Thr Pro Ser Ile Leu Arg Val
            20                  25

<210> SEQ ID NO 42
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula A5 with a methyl and
```

```
        a pentenyl side chain as shown on page 42 of specification, or a
        stapled derivative thereof
<220> FEATURE:
<221> NAME/KEY: MOD_RES
<222> LOCATION: (12)..(12)
<223> OTHER INFORMATION: X is amino acid of formula A5 with a methyl and
        a pentenyl side chain as shown on page 42 of specification, or a
        stapled derivative thereof

<400> SEQUENCE: 42

His Ile Arg Glu Leu Glu Asp Xaa Ile Asp Asn Xaa Leu Val Arg Val
1               5                   10                  15

Met Glu Glu Thr Pro Ser Ile Leu Arg Val
            20                  25

<210> SEQ ID NO 43
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula A5 with a methyl and
        a pentenyl side chain as shown on page 42 of specification, or a
        stapled derivative thereof
<220> FEATURE:
<221> NAME/KEY: MOD_RES
<222> LOCATION: (15)..(15)
<223> OTHER INFORMATION: X is amino acid of formula A5 with a methyl and
        a pentenyl side chain as shown on page 42 of specification, or a
        stapled derivative thereof

<400> SEQUENCE: 43

His Ile Arg Glu Leu Glu Asp Tyr Ile Asp Xaa Leu Leu Val Xaa Val
1               5                   10                  15

Met Glu Arg Thr Pro Ser Ile Leu Arg Val
            20                  25

<210> SEQ ID NO 44
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: X is amino acid of formula A5 with a methyl and
        a pentenyl side chain as shown on page 42 of specification, or a
        stapled derivative thereof
<220> FEATURE:
<221> NAME/KEY: MOD_RES
<222> LOCATION: (19)..(19)
<223> OTHER INFORMATION: X is amino acid of formula A5 with a methyl and
        a pentenyl side chain as shown on page 42 of specification, or a
        stapled derivative thereof

<400> SEQUENCE: 44

His Ile Arg Glu Leu Glu Asp Tyr Ile Asp Asn Leu Leu Val Xaa Val
1               5                   10                  15

Met Glu Xaa Thr Pro Ser Ile Leu Arg Val
            20                  25

<210> SEQ ID NO 45
<211> LENGTH: 26
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof

<400> SEQUENCE: 45

Ile Asn Phe Arg Leu Gln Xaa Tyr Ile Asp Xaa Ile Ile Val Ala Ile
1               5                   10                  15

Met Glu Thr Asn Pro Ser Ile Leu Glu Val
            20                  25

<210> SEQ ID NO 46
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (12)..(12)
<223> OTHER INFORMATION: X is amino acid of formula A5 with a methyl and
      a pentenyl side chain as shown on page 42 of specification, or a
      stapled derivative thereof

<400> SEQUENCE: 46

Ile Asn Phe Arg Leu Gln Asp Xaa Ile Asp Arg Xaa Ile Val Ala Ile
1               5                   10                  15

Met Glu Thr Asn Pro Ser Ile Leu Glu Val
            20                  25

<210> SEQ ID NO 47
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof

<400> SEQUENCE: 47

Ile Asn Phe Arg Leu Gln Asp Tyr Ile Asp Xaa Ile Ile Val Xaa Ile
1               5                   10                  15

Met Glu Thr Asn Pro Ser Ile Leu Glu Val
            20                  25
```

```
<210> SEQ ID NO 48
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (19)..(19)
<223> OTHER INFORMATION: X is amino acid of formula A5 with a methyl and
      a pentenyl side chain as shown on page 42 of specification, or a
      stapled derivative thereof

<400> SEQUENCE: 48

Ile Asn Phe Arg Leu Gln Asp Tyr Ile Asp Arg Ile Ile Val Xaa Ile
1               5                   10                  15

Met Glu Xaa Asn Pro Ser Ile Leu Glu Val
            20                  25

<210> SEQ ID NO 49
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: misc_feature
<222> LOCATION: (11)..(11)
<223> OTHER INFORMATION: X is amino acid of formula A5 with a methyl and
      a pentenyl side chain as shown on page 42 of specification, or a
      stapled derivative thereof

<400> SEQUENCE: 49

Ile Asn Phe Arg Leu Arg Xaa Tyr Met Asp Xaa Ile Ile Leu Ala Ile
1               5                   10                  15

Leu Asp His Asn Pro Ser Ile Leu Glu Ile
            20                  25

<210> SEQ ID NO 50
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (12)..(12)
<223> OTHER INFORMATION: X is amino acid of formula A5 with a methyl and
      a pentenyl side chain as shown on page 42 of specification, or a
      stapled derivative thereof

<400> SEQUENCE: 50

Ile Asn Phe Arg Leu Arg Gln Xaa Met Asp Lys Xaa Ile Leu Ala Ile
1               5                   10                  15
```

```
Leu Asp His Asn Pro Ser Ile Leu Glu Ile
            20                  25

<210> SEQ ID NO 51
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof

<400> SEQUENCE: 51

Ile Asn Phe Arg Leu Arg Gln Tyr Met Asp Xaa Ile Ile Leu Xaa Ile
1               5                   10                  15

Leu Asp His Asn Pro Ser Ile Leu Glu Ile
            20                  25

<210> SEQ ID NO 52
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (19)..(19)
<223> OTHER INFORMATION: X is amino acid of formula A5 with a methyl and
      a pentenyl side chain as shown on page 42 of specification, or a
      stapled derivative thereof

<400> SEQUENCE: 52

Ile Asn Phe Arg Leu Arg Gln Tyr Met Asp Lys Ile Ile Leu Xaa Ile
1               5                   10                  15

Leu Asp Xaa Asn Pro Ser Ile Leu Glu Ile
            20                  25

<210> SEQ ID NO 53
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (11)..(11)
<223> OTHER INFORMATION: X is amino acid of formula B5 with a dipentenyl
      side chain as shown on page 52 of specification, or a stapled
      derivative thereof
```

```
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof

<400> SEQUENCE: 53

Gln Val Arg Glu Leu Glu Xaa Tyr Ile Asp Xaa Leu Leu Val Xaa Val
1               5                   10                  15

Met Glu Glu Thr Pro Asn Ile Leu Arg Ile
            20                  25

<210> SEQ ID NO 54
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (15)..(15)
<223> OTHER INFORMATION: X is amino acid of formula B5 with a dipentenyl
      side chain as shown on page 52 of specification, or a stapled
      derivative thereof
<220> FEATURE:
<221> NAME/KEY: MOD_RES
<222> LOCATION: (19)..(19)
<223> OTHER INFORMATION: X is amino acid of formula A5 with a methyl and
      a pentenyl side chain as shown on page 42 of specification, or a
      stapled derivative thereof

<400> SEQUENCE: 54

Gln Val Arg Glu Leu Glu Asp Tyr Ile Asp Xaa Leu Leu Val Xaa Val
1               5                   10                  15

Met Glu Xaa Thr Pro Asn Ile Leu Arg Ile
            20                  25

<210> SEQ ID NO 55
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (11)..(11)
<223> OTHER INFORMATION: X is amino acid of formula B5 with a dipentenyl
      side chain as shown on page 52 of specification, or a stapled
      derivative thereof
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof

<400> SEQUENCE: 55

His Ile Arg Glu Leu Glu Xaa Tyr Ile Asp Xaa Leu Leu Val Xaa Val
1               5                   10                  15
```

```
Met Glu Glu Thr Pro Ser Ile Leu Arg Val
            20                  25

<210> SEQ ID NO 56
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (15)..(15)
<223> OTHER INFORMATION: X is amino acid of formula B5 with a dipentenyl
      side chain as shown on page 52 of specification, or a stapled
      derivative thereof
<220> FEATURE:
<221> NAME/KEY: MOD_RES
<222> LOCATION: (19)..(19)
<223> OTHER INFORMATION: X is amino acid of formula A5 with a methyl and
      a pentenyl side chain as shown on page 42 of specification, or a
      stapled derivative thereof

<400> SEQUENCE: 56

His Ile Arg Glu Leu Glu Asp Tyr Ile Asp Xaa Leu Leu Val Xaa Val
1               5                   10                  15

Met Glu Xaa Thr Pro Ser Ile Leu Arg Val
            20                  25

<210> SEQ ID NO 57
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (11)..(11)
<223> OTHER INFORMATION: X is amino acid of formula B5 with a dipentenyl
      side chain as shown on page 52 of specification, or a stapled
      derivative thereof
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof

<400> SEQUENCE: 57

Ile Asn Phe Arg Leu Gln Xaa Tyr Ile Asp Xaa Ile Ile Val Xaa Ile
1               5                   10                  15

Met Glu Thr Asn Pro Ser Ile Leu Glu Val
            20                  25

<210> SEQ ID NO 58
<211> LENGTH: 26
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (15)..(15)
<223> OTHER INFORMATION: X is amino acid of formula B5 with a dipentenyl
      side chain as shown on page 52 of specification, or a stapled
      derivative thereof
<220> FEATURE:
<221> NAME/KEY: MOD_RES
<222> LOCATION: (19)..(19)
<223> OTHER INFORMATION: X is amino acid of formula A5 with a methyl and
      a pentenyl side chain as shown on page 42 of specification, or a
      stapled derivative thereof

<400> SEQUENCE: 58

Ile Asn Phe Arg Leu Gln Asp Tyr Ile Asp Xaa Ile Ile Val Xaa Ile
1               5                   10                  15

Met Glu Xaa Asn Pro Ser Ile Leu Glu Val
            20                  25

<210> SEQ ID NO 59
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (11)..(11)
<223> OTHER INFORMATION: X is amino acid of formula B5 with a dipentenyl
      side chain as shown on page 52 of specification, or a stapled
      derivative thereof
<220> FEATURE:
<221> NAME/KEY: MOD_RES
<222> LOCATION: (15)..(15)
<223> OTHER INFORMATION: X is amino acid of formula A5 with a methyl and
      a pentenyl side chain as shown on page 42 of specification, or a
      stapled derivative thereof

<400> SEQUENCE: 59

Ile Asn Phe Arg Leu Arg Xaa Tyr Met Asp Xaa Ile Ile Leu Xaa Ile
1               5                   10                  15

Leu Asp His Asn Pro Ser Ile Leu Glu Ile
            20                  25

<210> SEQ ID NO 60
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: X is amino acid of formula A5 with a methyl and
      a pentenyl side chain as shown on page 42 of specification, or a
      stapled derivative thereof
<220> FEATURE:
<221> NAME/KEY: MOD_RES
<222> LOCATION: (15)..(15)
<223> OTHER INFORMATION: X is amino acid of formula B5 with a dipentenyl
      side chain as shown on page 52 of specification, or a stapled
```

```
        derivative thereof
<220> FEATURE:
<221> NAME/KEY: MOD_RES
<222> LOCATION: (19)..(19)
<223> OTHER INFORMATION: X is amino acid of formula A5 with a methyl and
      a pentenyl side chain as shown on page 42 of specification, or a
      stapled derivative thereof

<400> SEQUENCE: 60

Ile Asn Phe Arg Leu Arg Gln Tyr Met Asp Xaa Ile Ile Leu Xaa Ile
1               5                   10                  15

Leu Asp Xaa Asn Pro Ser Ile Leu Glu Ile
            20                  25

<210> SEQ ID NO 61
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 61

Lys Lys Glu Phe Gln Val Arg Glu Leu Glu Asp Tyr Ile Asp Asn Leu
1               5                   10                  15

Leu Val Arg Val Met Glu Glu Thr Pro Asn Ile Leu Arg Ile Pro Ala
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 62

Glu Arg Asp Thr His Ile Arg Glu Leu Glu Asp Tyr Ile Asp Asn Leu
1               5                   10                  15

Leu Val Arg Val Met Glu Glu Thr Pro Ser Ile Leu Arg Val Pro Tyr
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 63

Lys Gln Glu Glu Ile Asn Phe Arg Leu Gln Asp Tyr Ile Asp Arg Ile
1               5                   10                  15

Ile Val Ala Ile Met Glu Thr Asn Pro Ser Ile Leu Glu Val Lys
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 64

Glu Gln Glu Glu Ile Asn Phe Arg Leu Arg Gln Tyr Met Asp Lys Ile
1               5                   10                  15

Ile Leu Ala Ile Leu Asp His Asn Pro Ser Ile Leu Glu Ile Lys His
            20                  25                  30
```

```
<210> SEQ ID NO 65
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (12)..(12)
<223> OTHER INFORMATION: X is amino acid of formula A5 with a methyl and
      a pentenyl side chain and with a S configuration as shown on page
      43 of specification, or a stapled derivative thereof

<400> SEQUENCE: 65

Arg Gln Val Arg Glu Leu Glu Xaa Tyr Ile Asp Xaa Leu Leu Val Arg
1               5                   10                  15

Val Met Glu Glu Thr Pro Asn Ile Leu Arg Ile Pro Arg
            20                  25

<210> SEQ ID NO 66
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof

<400> SEQUENCE: 66

Arg Gln Val Arg Glu Leu Glu Asp Tyr Ile Asp Xaa Leu Leu Val Xaa
1               5                   10                  15

Val Met Glu Glu Thr Pro Asn Ile Leu Arg Ile Pro Arg
            20                  25

<210> SEQ ID NO 67
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (20)..(20)
<223> OTHER INFORMATION: X is amino acid of formula A5 with a methyl and
      a pentenyl side chain and with a S configuration as shown on page
      43 of specification, or a stapled derivative thereof

<400> SEQUENCE: 67
```

```
Arg Gln Val Arg Glu Leu Glu Asp Tyr Ile Asp Asn Leu Leu Val Xaa
1               5                   10                  15

Val Met Glu Xaa Thr Pro Asn Ile Leu Arg Ile Pro Arg
            20                  25
```

<210> SEQ ID NO 68
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (13)..(13)
<223> OTHER INFORMATION: X is amino acid of formula A5 with a methyl and
      a pentenyl side chain and with a S configuration as shown on page
      43 of specification, or a stapled derivative thereof

<400> SEQUENCE: 68

```
Arg Gln Val Arg Glu Leu Glu Asp Xaa Ile Asp Asn Xaa Leu Val Arg
1               5                   10                  15

Val Met Glu Glu Thr Pro Asn Ile Leu Arg Ile Pro Arg
            20                  25
```

<210> SEQ ID NO 69
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (12)..(12)
<223> OTHER INFORMATION: X is amino acid of formula A5 with a methyl and
      a pentenyl side chain and with a S configuration as shown on page
      43 of specification, or a stapled derivative thereof

<400> SEQUENCE: 69

```
Arg Ile Asn Phe Arg Leu Gln Xaa Tyr Ile Asp Xaa Ile Ile Val Arg
1               5                   10                  15

Ile Met Glu Thr Asn Pro Ser Ile Leu Glu Val Lys
            20                  25
```

<210> SEQ ID NO 70
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (16)..(16)
<223> OTHER INFORMATION: X is amino acid of formula A5 with a methyl and -continued a pentenyl side chain and with a S configuration as shown on page
43 of specification, or a stapled derivative thereof

<400> SEQUENCE: 70

Arg Ile Asn Phe Arg Leu Gln Asp Tyr Ile Asp Xaa Ile Ile Val Xaa
1               5                   10                  15

Ile Met Glu Thr Asn Pro Ser Ile Leu Glu Val Lys
            20                  25

<210> SEQ ID NO 71
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (20)..(20)
<223> OTHER INFORMATION: X is amino acid of formula A5 with a methyl and
      a pentenyl side chain and with a S configuration as shown on page
      43 of specification, or a stapled derivative thereof

<400> SEQUENCE: 71

Arg Ile Asn Phe Arg Leu Gln Asp Tyr Ile Asp Arg Ile Ile Val Xaa
1               5                   10                  15

Ile Met Glu Xaa Asn Pro Ser Ile Leu Glu Val Lys
            20                  25

<210> SEQ ID NO 72
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (13)..(13)
<223> OTHER INFORMATION: X is amino acid of formula A5 with a methyl and
      a pentenyl side chain and with a S configuration as shown on page
      43 of specification, or a stapled derivative thereof

<400> SEQUENCE: 72

Arg Ile Asn Phe Arg Leu Gln Asp Xaa Ile Asp Arg Xaa Ile Val Arg
1               5                   10                  15

Ile Met Glu Thr Asn Pro Ser Ile Leu Glu Val Lys
            20                  25

<210> SEQ ID NO 73
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 73

Asn Phe Arg Leu Gln Asp Tyr Ile Asp Arg Ile Ile Val Ala Ile Met
1               5                   10                  15

```
Glu Thr Asn Pro Ser Ile Leu Glu Val Lys
            20                  25

<210> SEQ ID NO 74
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (16)..(16)
<223> OTHER INFORMATION: Met is a methionine that is oxidized

<400> SEQUENCE: 74

Asn Phe Arg Leu Gln Asp Tyr Ile Asp Arg Ile Ile Val Ala Ile Met
1               5                   10                  15

Glu Thr Asn Pro Ser Ile Leu Glu Val Lys
            20                  25

<210> SEQ ID NO 75
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (18)..(18)
<223> OTHER INFORMATION: X is norleucine isostere
<220> FEATURE:
<221> NAME/KEY: MOD_RES
<222> LOCATION: (20)..(20)
<223> OTHER INFORMATION: X is amino acid of formula A5 with a methyl and
      a pentenyl side chain and with a S configuration as shown on page
      43 of specification, or a stapled derivative thereof

<400> SEQUENCE: 75

Arg Gln Val Arg Glu Leu Glu Asn Tyr Ile Asp Arg Leu Leu Val Xaa
1               5                   10                  15

Val Asn Glu Xaa Thr Pro Asn Ile Leu Arg Ile Pro Arg
            20                  25

<210> SEQ ID NO 76
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (18)..(18)
<223> OTHER INFORMATION: X is norleucine isostere
```

<400> SEQUENCE: 76

Arg Ile Asn Phe Arg Leu Gln Asn Tyr Ile Asp Xaa Ile Ile Val Xaa
1               5                   10                  15

Ile Asn Glu Thr Asn Pro Ser Ile Leu Arg Val Lys
            20                  25

<210> SEQ ID NO 77
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (13)..(13)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (18)..(18)
<223> OTHER INFORMATION: X is norleucine isostere

<400> SEQUENCE: 77

Arg Ile Asn Phe Arg Leu Gln Asn Xaa Ile Asp Arg Xaa Ile Val Arg
1               5                   10                  15

Ile Asn Glu Thr Asn Pro Ser Ile Leu Glu Val Lys
            20                  25

<210> SEQ ID NO 78
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (13)..(13)
<223> OTHER INFORMATION: X is amino acid of formula A5 with a methyl and
      a pentenyl side chain and with a S configuration as shown on page
      43 of specification, or a stapled derivative thereof

<400> SEQUENCE: 78

Arg Ile Asn Phe Arg Leu Gln Asn Xaa Ile Asp Arg Xaa Ile Val Arg
1               5                   10                  15

Ile Phe Glu Thr Asn Pro Ser Ile Leu Glu Val Lys
            20                  25

<210> SEQ ID NO 79
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (12)..(12)

```
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof

<400> SEQUENCE: 79

Arg Ile Asn Phe Arg Leu Gln Asn Tyr Ile Asp Xaa Ile Ile Val Xaa
1               5                   10                  15

Ile Phe Glu Thr Asn Pro Ser Ile Leu Glu Val Lys
            20                  25

<210> SEQ ID NO 80
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (18)..(18)
<223> OTHER INFORMATION: X is norleucine isostere

<400> SEQUENCE: 80

Arg Ile Asn Phe Asp Leu Gln Asn Tyr Ile Arg Xaa Ile Ile Val Xaa
1               5                   10                  15

Ile Asn Glu Thr Asn Pro Ser Ile Leu Glu Val Lys
            20                  25

<210> SEQ ID NO 81
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (16)..(16)
<223> OTHER INFORMATION: X is amino acid of formula A5 with a methyl and
      a pentenyl side chain and with a S configuration as shown on page
      43 of specification, or a stapled derivative thereof

<400> SEQUENCE: 81

Arg Ile Asn Phe Asp Leu Gln Asn Tyr Ile Arg Xaa Ile Ile Val Xaa
1               5                   10                  15

Ile Ala Glu Thr Asn Pro Ser Ile Leu Glu Val Lys
            20                  25
```

```
<210> SEQ ID NO 82
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (13)..(13)
<223> OTHER INFORMATION: X is amino acid of formula A5 with a methyl and
      a pentenyl side chain and with a S configuration as shown on page
      43 of specification, or a stapled derivative thereof

<400> SEQUENCE: 82

Arg Ile Asn Phe Arg Leu Gln Asn Xaa Ile Asp Arg Xaa Ile Val Arg
1               5                   10                  15

Ile Phe Glu Thr Asn Pro Ser Ile Leu Arg Val Lys
            20                  25

<210> SEQ ID NO 83
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (13)..(13)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (18)..(18)
<223> OTHER INFORMATION: X is norleucine isostere

<400> SEQUENCE: 83

Arg Ile Asn Phe Arg Leu Gln Asn Xaa Ile Asp Arg Xaa Ile Val Arg
1               5                   10                  15

Ile Asn Glu Thr Asn Pro Ser Ile Leu Arg Val Lys
            20                  25

<210> SEQ ID NO 84
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: X is amino acid of formula A5 with a methyl and
      a pentenyl side chain and with a S configuration as shown on page
      43 of specification, or a stapled derivative thereof
<220> FEATURE:
<221> NAME/KEY: MOD_RES
<222> LOCATION: (13)..(13)
<223> OTHER INFORMATION: X is amino acid of formula A5 with a methyl and
      a pentenyl side chain and with a S configuration as shown on page
      43 of specification, or a stapled derivative thereof
```

```
<400> SEQUENCE: 84

Arg Ile Asn Phe Arg Leu Gln Asn Xaa Ile Asp Arg Xaa Ala Ala Arg
1               5                   10                  15

Ile Ala Glu Thr Asn Pro Ser Ile Leu Glu Val Lys
            20                  25

<210> SEQ ID NO 85
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 85

Gln Val Arg Glu
1

<210> SEQ ID NO 86
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 86

His His His His His His
1               5

<210> SEQ ID NO 87
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 87

Phe Arg Leu Gln
1
```

STABILIZED POLYPEPTIDES AS REGULATORS OF RAB GTPASE FUNCTION

RELATED APPLICATIONS

The present application is a national stage filing under 35 U.S.C. §371 of international PCT application, PCT/US2012/042738, filed Jun. 15, 2012, which claims priority under 35 U.S.C. §119(e) to U.S. provisional patent application, U.S. Ser. No 61/498,382, filed Jun. 17, 2011, each of which is incorporated herein by reference.

BACKGROUND OF THE INVENTION

The important biological roles that peptides and proteins play as hormones, enzyme inhibitors, substrates, gene regulators, and neurotransmitters has led to the use of peptides and/or peptide mimetics as therapeutic agents. The peptide's bioactive conformation, combining structural elements such as alpha-helices, beta-sheets, turns, and/or loops, is important as it allows for selective biological recognition of receptors, enzymes, and nucleic acids, thereby influencing cell-cell communication and/or controlling vital cellular functions, such as metabolism, immune defense, and cell division (see, e.g., Babine et al., *Chem. Rev.* (1997) 97:1359). Unfortunately, the utility of peptides as drugs is severely limited by several factors, including their rapid degradation by proteases under physiological conditions, their poor cell permeability, and their lack of binding specificity resulting from conformational flexibility. Moreover, alpha-helical peptides have a propensity for unraveling and forming random coils, which are, in most cases, biologically less active, or even inactive, and are highly susceptible to proteolytic degradation.

Many research groups have developed strategies for the design and synthesis of more robust peptides as therapeutics. For example, one strategy has been to incorporate more robust functionalities into the peptide chain while still maintaining the peptide's unique conformation and secondary structure (see, e.g., Gante, *Angew. Chem. Int. Ed. Engl.* (1994) 33:1699-1720; Liskamp, *Recl. Trav. Chim. Pays-Bas* (1994) 113:1; Giannis, *Angew. Chem. Int. Ed. Engl.* (1993) 32:1244; Bailey, *Peptide Chemistry*, Wiley, New York (1990), 182; and references cited therein). Another approach has been to stabilize the peptide via covalent cross-links (see, e.g., Phelan et al., *J. Am. Chem. Soc.* (1997) 119:455; Leuc et al., *Proc. Natl. Acad. Sci. USA* (2003) 100: 11273; Bracken et al., *J. Am. Chem. Soc.* (1994) 116:6432; Yan et al., *Bioorg. Med. Chem.* (2004) 14:1403). However, the majority of reported approaches involved the use of polar and/or labile cross-linking groups.

"Peptide stapling" is a term coined for a synthetic methodology used to covalently join two olefin-containing side chains present in a polypeptide chain by ring closing metathesis (RCM) (see, e.g., Blackwell et al., *J. Org. Chem.* (2001) 66:5291-5302; Blackwell et al., *Angew. Chem. Int. Ed.* (1998) 37:3281). Stapling of a polypeptide using a hydrocarbon cross-linker created from an olefin metathesis reaction has been shown to help maintain a peptide's native conformation, particularly under physiological conditions (see, e.g., U.S. Pat. Nos. 7,192,713; 7,723,469; 7,786,072; U.S. Patent Application Publication Nos: 2010-0184645; 2010-0168388; 2010-0081611; 2009-0176964; 2009-0149630; 2006-0008848; PCT Application Publication Nos: WO 2010/011313; WO 2008/121767; WO 2008/095063; WO 2008/061192; WO 2005/044839; Schafmeister et al., *J. Am. Chem. Soc.* (2000) 122:5891-5892; Walensky et al., *Science* (2004) 305:1466-1470). The stapled polypeptide strategy in which an all-hydrocarbon cross-link is generated by olefin metathesis is an efficient approach to increase the helical character of polypeptides to target α-helical binding motifs. Unlike their unstapled analogues these hydrocarbon-stapled polypeptides have shown to be α-helical, protease-resistant, and cell permeable.

There are sixty known RAB GTPase isoforms and six RAB-family interacting protein (RAB-FIP or FIP) isoforms known. Each FIP isoform contains a highly conserved C-terminal RAB-binding domain (RabBD) of approximately thirty amino acids (see, e.g., Stenmark et al., *Genome Biol* (2011) 2:3007) important for RAB-FIP binding interactions and subsequent biological function. The conserved RabBD has a partial alpha-helical structure that undergoes a conformational change upon RAB binding. RAB function is coupled through effector proteins, including GTP transferases, GAP proteins, geranyl transferases, and RAB Coupling Proteins/RAB family interacting proteins (FIPs). Some diseases such as those resulting in bleeding and pigmentation disorders (e.g., Griscelli syndrome, Hermansky-Pudlak syndrome), mental retardation, neuropathy (e.g., Charcot-Marie-Tooth (CMT) disease), kidney disease (e.g., tuberous sclerosis), and blindness (e.g., choroideremeia) arise from direct loss of function mutations of RAB GTPases or associated regulatory molecules (see, e.g., Stein et al., *Advanced Drug Delivery Reviews* (2003) 55:1421-1437). In contrast, in a number of cancers (e.g., prostate, liver, breast, ovarian) as well as vascular, lung, and thyroid diseases, the overexpression of certain RAB GTPases have been correlated with disease pathogenesis (see, e.g., Stein supra; Chia et al., *Biochimica et Biophysica Acta* (2009) 2:110-116; Cheng et al., *Nature Medicine* (2004) 10:1251-1256). The development of compounds that target RAB proteins and modulate the endocytic protein trafficking pathway is a worthwhile effort in the search for new and improved therapeutics.

SUMMARY OF THE INVENTION

Provided herein are inventive polypeptides comprising a modified C-terminal RAB binding domain (RabBD) of Rab family interacting proteins (FIPs) stabilized by peptide stapling or stitching. Also provided herein are methods for modulating RAB function comprising contacting an inventive stapled polypeptide with a RAB protein. In certain embodiments, the inventive stapled polypeptides bind to RAB protein. In certain embodiments, the inventive stapled polypeptides are useful in the treatment of a condition, e.g., a condition associated with aberrant RAB function, e.g., by inhibition of RAB. Exemplary conditions include, but are not limited to, a proliferative, a neurological, an immunological, an endocrinologic, a cardiovascular, a hematologic, or an inflammatory condition. In certain embodiments, the condition a bleeding disorder, a pigmentation disorder, mental retardation, neuropathy (e.g., Charcot-Marie-Tooth (CMT) disease), kidney disease (e.g., tuberous sclerosis), blindness (e.g., choroideremeia), cancer (e.g., prostate cancer, liver cancer, breast cancer, ovarian cancer) as well as vascular disease, lung disease, and thyroid disease.

Also provided are synthetic precursors to the inventive stapled polypeptides, referred to herein as unstapled polypeptides, and methods of making the inventive stapled polypeptides therefrom.

This application refers to various issued patent, published patent applications, journal articles, and other publications, all of which are incorporated herein by reference.

The details of one or more embodiments of the invention are set forth herein. Other features, objects, and advantages of the invention will be apparent from the description, the figures, the examples, and the claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

"Stapling" or "hydrocarbon-stapling," as used herein, is a process by which two terminally unsaturated amino acid side chains in a polypeptide chain react with each in the presence of a ring closing metathesis catalyst to generate a C—C double bonded cross-link between the two amino acids (a "staple"). Stapling engenders constraint on a secondary structure, such as an alpha helical structure. The length and geometry of the cross-link can be optimized to improve the yield of the desired secondary structure content. The constraint provided can, for example, prevent the secondary structure to unfold and/or can reinforce the shape of the secondary structure, and thus makes the secondary structure more stable. Multiple stapling is also referred to herein as "stitching." See, e.g., U.S. Pat. Nos. 7,192,713; 7,723,469; 7,786,072; U.S. Patent Application Publication Nos: 2010-0184645; 2010-0168388; 2010-0081611; 2009-0176964; 2009-0149630; 2006-0008848; PCT Application Publication Nos: WO 2010/011313; WO 2008/121767; WO 2008/095063; WO 2008/061192; and WO 2005/044839, which depict stapling and stitching of polypeptides. In certain embodiments, stapling may occur at i,i+3, i,i+4, and/or i,i+7 positions of the polypeptide.

An "unstapled" polypeptide or amino acid sequence is a polypeptide or sequence comprising at least two amino acids having sites of terminal unsaturation capable of undergoing ring closing metathesis to generate a cross-link between the two amino acids, thereby providing a "stapled" polypeptide. A stapled polypeptide with more than one staple, i.e., two, three, four, five, six, seven, eight, nine, or ten staples, may also be referred to as a "stitched" polypeptide. After the unstapled polypeptide is synthesized the polypeptide is contacted with a ring closing metathesis (RCM) catalyst to promote stapling of the polypeptide (Bernal et al., J. Am. Chem. Soc. 2007, 129, 2456-2457). In certain embodiments, the RCM catalyst is a ruthenuim catalyst. Suitable RCM catalysts are described in, for example, Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299.

The compounds of the present invention (e.g., amino acids, and unstapled, partially stapled, and stapled polypeptides) may exist in particular geometric or stereoisomeric forms. The present invention contemplates all such compounds, including cis- and trans-isomers, R- and S-enantiomers, diastereomers, (D)- and (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments, the compound of the present invention is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E.L. Eliel, Ed., Univ. of Notre Dame Press, Notre Dame, Ind. 1972).

It will be appreciated that the compounds of the present invention, as described herein, may be substituted with any number of substituents or functional moieties. As used herein, "optionally substituted" refers to a group as substituted or unsubstituted. In general, the term "substituted" whether preceded by the term "optionally" or not, and substituents contained in Formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, aryalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The term "stable moiety," as used herein, preferably refers to a moiety which possess stability sufficient to allow manufacture, and which maintains its integrity for a sufficient period of time to be useful for the purposes detailed herein. The present invention contemplates any and all such combinations in order to arrive at a stable substituent/moiety. Additional examples of generally applicable substituents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substituent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1-4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$alkyl). In another embodiment, the alkyl group employed contains 1-15 carbon atoms ($C_{1-15}$alkyl). In another embodiment, the alkyl group employed contains 1-10 carbon atoms ($C_{1-10}$alkyl). In another embodiment, the alkyl group employed contains 1-8 carbon atoms ($C_{1-8}$alkyl). In another embodiment, the alkyl group employed contains 1-6 carbon atoms ($C_{1-6}$alkyl). In another embodiment, the alkyl group employed contains 1-5 carbon atoms ($C_{1-5}$alkyl). In another embodiment, the alkyl group employed contains 1-4 carbon atoms ($C_{1-4}$alkyl). In another embodiment, the alkyl group employed contains 1-3 carbon atoms ($C_{1-3}$alkyl). In another embodiment, the alkyl group employed contains 1-2 carbon atoms ($C_{1-2}$alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$alkenyl). In some embodiments, the alkenyl group employed in the invention contains 2-15 carbon atoms ($C_{2-15}$alkenyl). In another embodiment, the alkenyl group employed contains 2-10 carbon atoms ($C_{2-10}$alkenyl). In still other embodiments, the alkenyl group contains 2-8 carbon atoms ($C_{2-8}$alkenyl). In yet other embodiments, the alkenyl group contains 2-6 carbons ($C_{2-6}$alkenyl). In yet other embodiments, the alkenyl group contains 2-5 carbons ($C_{2-5}$alkenyl). In yet other embodiments, the alkenyl group contains 2-4 carbons ($C_{2-4}$alkenyl). In yet other embodiments, the alkenyl group contains 2-3 carbons ($C_{2-3}$alkenyl). In yet other embodiments, the alkenyl group contains 2 carbons ($C_2$alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$alkynyl). In some embodiments, the alkynyl group employed in the invention contains 2-15 carbon atoms ($C_{2-15}$alkynyl). In another embodiment, the alkynyl group employed contains 2-10 carbon atoms ($C_{2-10}$alkynyl). In still other embodiments, the alkynyl group contains 2-8 carbon atoms ($C_{2-8}$alkynyl). In still other embodiments, the alkynyl group contains 2-6 carbon atoms ($C_{2-6}$alkynyl). In still other embodiments, the alkynyl group contains 2-5 carbon atoms ($C_{2-5}$alkynyl). In still other embodiments, the alkynyl group contains 2-4 carbon atoms ($C_{2-4}$alkynyl). In still other embodiments, the alkynyl group contains 2-3 carbon atoms ($C_{2-3}$alkynyl). In still other embodiments, the alkynyl group contains 2 carbon atoms ($C_2$alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "carbocyclic" or "carbocyclyl" as used herein, refers to an as used herein, refers to a cyclic aliphatic group containing 3-10 carbon ring atoms ($C_{3-10}$carbocyclic). Carbocyclic group substituents include, but are not limited to, any of the substituents described herein, that result in the formation of a stable moiety.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that further contains one or more heteroatoms (e.g., oxygen, sulfur, nitrogen, phosphorus, or silicon atoms) between carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms and 1-6 heteroatoms ($C_{1-20}$heteroaliphatic). In certain embodiments, the heteroaliphatic group contains 1-10 carbon atoms and 1-4 heteroatoms ($C_{1-10}$heteroaliphatic). In certain embodiments, the heteroaliphatic group contains 1-6 carbon atoms and 1-3 heteroatoms ($C_{1-6}$heteroaliphatic). In certain embodiments, the heteroaliphatic group contains 1-5 carbon atoms and 1-3 heteroatoms ($C_{1-5}$heteroaliphatic). In certain embodiments, the heteroaliphatic group contains 1-4 carbon atoms and 1-2 heteroatoms ($C_{1-4}$heteroaliphatic). In certain embodiments, the heteroaliphatic group contains 1-3 carbon atoms and 1 heteroatom ($C_{1-3}$heteroaliphatic). In certain embodiments, the heteroaliphatic group contains 1-2 carbon atoms and 1 heteroatom ($C_{1-2}$heteroaliphatic). Heteroaliphatic group substituents include, but are not limited to, any of the substituents described herein, that result in the formation of a stable moiety.

The term "heteroalkyl," as used herein, refers to an alkyl moiety, as defined herein, which contain one or more heteroatoms (e.g., oxygen, sulfur, nitrogen, phosphorus, or silicon atoms) in between carbon atoms. In certain embodiments, the heteroalkyl group contains 1-20 carbon atoms and 1-6 heteroatoms ($C_{1-20}$ heteroalkyl). In certain embodiments, the heteroalkyl group contains 1-10 carbon atoms and 1-4 heteroatoms ($C_{1-10}$ heteroalkyl). In certain embodiments, the heteroalkyl group contains 1-6 carbon atoms and 1-3 heteroatoms ($C_{1-6}$ heteroalkyl). In certain embodiments, the heteroalkyl group contains 1-5 carbon atoms and 1-3 heteroatoms ($C_{1-5}$ heteroalkyl). In certain embodiments, the heteroalkyl group contains 1-4 carbon atoms and 1-2 heteroatoms ($C_{1-4}$ heteroalkyl). In certain embodiments, the heteroalkyl group contains 1-3 carbon atoms and 1 heteroatom ($C_{1-3}$ heteroalkyl). In certain embodiments, the heteroalkyl group contains 1-2 carbon atoms and 1 heteroatom ($C_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety.

The term "heteroalkenyl," as used herein, refers to an alkenyl moiety, as defined herein, which further contains one or more heteroatoms (e.g., oxygen, sulfur, nitrogen, phosphorus, or silicon atoms) in between carbon atoms. In certain embodiments, the heteroalkenyl group contains 2-20 carbon atoms and 1-6 heteroatoms ($C_{2-20}$ heteroalkenyl). In certain embodiments, the heteroalkenyl group contains 2-10 carbon atoms and 1-4 heteroatoms ($C_{2-10}$ heteroalkenyl). In certain embodiments, the heteroalkenyl group contains 2-6 carbon atoms and 1-3 heteroatoms ($C_{2-6}$ heteroalkenyl). In certain embodiments, the heteroalkenyl group contains 2-5 carbon atoms and 1-3 heteroatoms ($C_{2-5}$ heteroalkenyl). In certain embodiments, the heteroalkenyl group contains 2-4 carbon atoms and 1-2 heteroatoms ($C_{2-4}$ heteroalkenyl). In certain embodiments, the heteroalkenyl group contains 2-3 carbon atoms and 1 heteroatom ($C_{2-3}$ heteroalkenyl). The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which further contains one or more heteroatoms (e.g., oxygen, sulfur, nitrogen, phosphorus, or silicon atoms) in between carbon atoms. In certain embodiments, the heteroalkynyl group contains 2-20 carbon atoms and 1-6 heteroatoms ($C_{2-20}$ heteroalkynyl). In certain embodiments, the heteroalkynyl group contains 2-10 carbon atoms and 1-4 heteroatoms ($C_{2-10}$ heteroalkynyl). In certain embodiments, the heteroalkynyl group contains 2-6 carbon atoms and 1-3 heteroatoms ($C_{2-6}$ heteroalkynyl). In certain embodiments, the heteroalkynyl group contains 2-5 carbon atoms and 1-3 heteroatoms ($C_{2-5}$ heteroalkynyl). In certain embodiments, the heteroalkynyl group contains 2-4 carbon atoms and 1-2 heteroatoms ($C_{2-4}$ heteroalkynyl). In certain embodiments, the heteroalkynyl group contains 2-3 carbon atoms and 1 heteroatom ($C_{2-3}$ heteroalkynyl). The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety.

The term "aryl," as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but are not limited to, phenyl, biphenyl, naphthyl, and the like, which may bear one or more substituents. Aryl substituents include, but are not limited to, any of the substituents described herein, that result in the formation of a stable moiety. The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

The term "heteroaryl," as used herein, refers to an aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety. The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

The term "acyl," as used herein, is a subset of a substituted alkyl group, and refers to a group having the general formula —C(=O)$R^A$, —C(=O)O$R^A$, -C(=O)—O—C(=O)$R^A$, —C(=O)S$R^A$, —C(=O)N($R^A$)$_2$, —C(=S)$R^A$, —C(=S)N($R^A$)$_2$, and —C(=S)S($R^A$), —C(=NR$^A$)$R^A$, —C(=NR$^A$)OR$^A$, —C(=NR$^A$)SR$^A$, and —C(∀NR$^A$)N($R^A$)$_2$, wherein $R^A$ is hydrogen; halogen; substituted or unsubstituted hydroxyl; substituted or unsubstituted thiol; substituted or unsubstituted amino; acyl; optionally substituted aliphatic; optionally substituted heteroaliphatic; optionally substituted alkyl; optionally substituted alkenyl; optionally substituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety.

The term "acylene," as used herein, is a subset of a substituted alkylene, substituted alkenylene, substituted alkynylene, substituted heteroalkylene, substituted heteroalkenylene, or substituted heteroalkynylene group, and refers to an acyl group having the general formulae: —$R^O$—($C_{50\,X}^1$)—$R^O$—, —$R^{uO}$—$X^2$(C=$X^1$)—$R^O$—, or —$R^O$—$X^2$(C=$X^1$)$X^3$—$R^O$—, where $X^1$, $X^2$, and $X^3$ is, independently, oxygen, sulfur, or NR$^r$, wherein R$^r$ is hydrogen or optionally substituted aliphatic, and $R^O$ is an optionally substituted alkylene, alkenylene, alkynylene, heteroalkylene, heteroalkenylene, or heteroalkynylene group, as defined herein. Exemplary acylene groups wherein $R^O$ is alkylene includes —(CH$_2$)$_T$—O(C=O)—(CH$_2$)$_T$—; —(CH$_2$)$_T$—NR$^r$(C=O)—(CH$_2$)$_T$—; —(CH$_2$)$_T$—O(C=NR$^r$)—(CH$_2$)$_T$—; —(CH$_2$)$_T$—NR$^r$(C=NR$^r$)—(CH$_2$)$_T$—; —(CH$_2$)$_T$—(C=O)—(CH$_2$)$_T$—; —(CH$_2$)$_T$—(C=NR$^r$)—(CH$_2$)$_T$—; —(CH$_2$)$_T$—S(C=S)—(CH$_2$)$_T$—; —(CH$_2$)$_T$—NR$^r$(C=S)—(CH$_2$)$_T$—; —(CH$_2$)$_T$—S(C=NR$^r$)—(CH$_2$)$_T$—; —(CH$_2$)$_T$—O(C=S)—(CH$_2$)$_T$—; —(CH$_2$)$_T$—(C=S)—(CH$_2$)$_T$—; or —(CH$_2$)$_T$—S(C=O)—(CH$_2$)$_T$—, and the like, which may bear one or more substituents; and wherein each instance of T is, independently, an integer between 0 to 20. Acylene groups may be cyclic or acyclic, branched or unbranched, substituted or unsubstituted. Acylene substituents include, but are not limited to, any of the substituents described herein, that result in the formation of a stable moiety.

The term "amino," as used herein, refers to a group of the formula (—NH$_2$). A "substituted amino" refers either to a mono-substituted amine (—NHR$^h$) of a disubstituted amine (—NR$^h_2$), wherein the R$^h$ substituent is any substituent as described herein that results in the formation of a stable moiety (e.g., an amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the di-substituted amino group (—NR$^h_2$) form a 5- to 6-membered heterocyclic ring.

The term "hydroxy" or "hydroxyl," as used herein, refers to a group of the formula (—OH). A "substituted hydroxyl" refers to a group of the formula (—OR$^1$), wherein R$^1$ can be any substituent which results in a stable moiety (e.g., a hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "thio" or "thiol," as used herein, refers to a group of the formula (—SH). A "substituted thiol" refers to a group of the formula (—SR$^r$), wherein R$^r$ can be any substituent that results in the formation of a stable moiety (e.g., a thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "imino," as used herein, refers to a group of the formula (=NR$^r$), wherein R$^r$ corresponds to hydrogen or any substituent as described herein, that results in the formation of a stable moiety (for example, an amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "azido," as used herein, refers to a group of the formula (—N$_3$).

The term "cyano," as used herein, refers to a group of the formula (—CN).

The terms "halo" and "halogen," as used herein, refer to an atom selected from fluorine (fluoro, —F), chlorine (chloro, —Cl), bromine (bromo, —Br), and iodine (iodo, —I).

The term "isocyano," as used herein, refers to a group of the formula (—NC).

The term "nitro," as used herein, refers to a group of the formula (—NO$_2$).

The term "oxo," as used herein, refers to a group of the formula (=O).

The term "thiooxo," as used herein, refers to a group of the formula (=S).

An "amino-protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5- dimethyl-3-oxo-1-cyclohexenyl)amine, N-borane derivative, N-diphenylborinic acid derivative, N-[phenyhpentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "carboxylic acid protecting group" or "protected carboxylic acid," as used herein, are well known in the art and include those described in detail in Greene (1999). Examples of protected carboxylic acids further include, but are not limited to, silyl-, alkyl-, alkenyl-, aryl-, and arylalkyl-protected carboxylic acids. Examples of silyl groups include trimethylsilyl, triethylsilyl, t-butyldimethylsilyl, t-butyldiphenylsilyl, triisopropylsilyl, and the like. Examples of alkyl groups include methyl, benzyl, p-methoxybenzyl, 3,4-dimethoxybenzyl, trityl, t-butyl, tetrahydropyran-2-yl. Examples of alkenyl groups include allyl. Examples of aryl groups include optionally substituted phenyl, biphenyl, or naphthyl. Examples of arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "hydroxyl protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4'4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t- butoxydisiloxane-1,3-diylidene derivative (TBDS), cyclic carbonates, cyclic boronates, ethyl boronate, and phenyl boronate.

A "thiol protecting group," as used herein, are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of protected thiol groups include, but are not limited to, thioesters, carbonates, sulfonates allyl thioethers, thioethers, silyl thioethers, alkyl thioethers, arylalkyl thioethers, and alkyloxyalkyl thioethers. Examples of ester groups include formates, acetates, proprionates, pentanoates, crotonates, and benzoates. Specific examples of ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of silyl groups include trimethylsilyl, triethylsilyl, t-butyldimethylsilyl, t-butyldiphenylsilyl, triisopropylsilyl ether, and other trialkylsilyl ethers. Examples of alkyl groups include methyl, benzyl, p-methoxybenzyl, 3,4-dimethoxybenzyl, trityl, t-butyl, and allyl ether, or derivatives thereof. Examples of arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

As used herein, the symbol -[$X_{AA}$]- refers to an amino acid, e.g., of the formula:

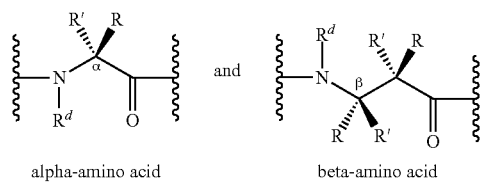

alpha-amino acid     beta-amino acid wherein each instance of R and R' independently are selected from the group consisting of hydrogen, optionally substituted aliphatic, optionally substituted heteroaliphatic, optionally substituted aryl, optionally substituted heteroaryl, and R$^d$ is hydrogen or an amino protecting group. Amino acids encompassed by the above two formulae include, without limitation, natural alpha-amino acids such as D- and L-isomers of the 20 common naturally occurring alpha-amino acids found in polypeptides and proteins (e.g., A, R, N, C, D, Q, E, G, H, I, L, K, M, F, P, S, T, W, Y, V, as depicted in Table 1 below), unnatural alpha-amino acids (examples of which are depicted in Table 2 below), natural beta-amino acids (e.g., beta-alanine), and unnatural beta-amino acids.

TABLE 1

Natural alpha-amino acids

| | R | R' |
|---|---|---|
| L-Alanine (A) | —CH$_3$ | —H |
| L-Arginine (R) | —CH$_2$CH$_2$CH$_2$—NHC(=NH)NH$_2$ | —H |
| L-Asparagine (N) | —CH$_2$C(=O)NH$_2$ | —H |

TABLE 1-continued

Natural alpha-amino acids

| | R | R' |
|---|---|---|
| L-Aspartic acid (D) | —CH$_2$CO$_2$H | —H |
| L-Cysteine (C) | —CH$_2$SH | —H |
| L-Glutamic acid (E) | —CH$_2$CH$_2$CO$_2$H | —H |
| L-Glutamine (Q) | —CH$_2$CH$_2$C(=O)NH$_2$ | —H |
| Glycine (G) | —H | —H |
| L-Histidine (H) | —CH$_2$-2-(1H-imidazole) | —H |
| L-Isoleucine (I) | -sec-butyl | —H |
| L-Leucine (L) | -iso-butyl | —H |
| L-Lysine (K) | —CH$_2$CH$_2$CH$_2$CH$_2$NH$_2$ | —H |
| L-Methionine (M) | —CH$_2$CH$_2$SCH$_3$ | —H |
| L-Phenylalanine (F) | —CH$_2$Ph | —H |
| L-Proline (P) | -2-(pyrrolidine) | —H |
| L-Serine (S) | —CH$_2$OH | —H |
| L-Threonine (T) | —CH$_2$CH(OH)(CH$_3$) | —H |
| L-Tryptophan (W) | —CH$_2$-3-(1H-indole) | —H |
| L-Tyrosine (Y) | —CH$_2$-(p-hydroxyphenyl) | —H |
| L-Valine (V) | -isopropyl | —H |

TABLE 2

Unnatural alpha-amino acids

| | R | R' |
|---|---|---|
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |
| Di-vinyl | —CH=CH$_2$ | —CH=CH$_2$ |

| | R and R' are equal to: |
|---|---|
| α-methyl-Alanine (Aib) | —CH$_3$, —CH$_3$ |
| α-methyl-Arginine | —CH$_3$, —CH$_2$CH$_2$CH$_2$—NHC(=NH)NH$_2$ |
| α-methyl-Asparagine | —CH$_3$, —CH$_2$C(=O)NH$_2$ |
| α-methyl-Aspartic acid | —CH$_3$, —CH$_2$CO$_2$H |
| α-methyl-Cysteine | —CH$_3$, —CH$_2$SH |
| α-methyl-Glutamic acid | —CH$_3$, —CH$_2$CH$_2$CO$_2$H |
| α-methyl-Glutamine | —CH$_3$, —CH$_2$CH$_2$C(=O)NH$_2$ |
| α-methyl-Histidine | —CH$_3$, —CH$_2$-2-(1H-imidazole) |
| α-methyl-Isoleucine | —CH$_3$, -sec-butyl |
| α-methyl-Leucine | —CH$_3$, -iso-butyl |
| α-methyl-Lysine | —CH$_3$, —CH$_2$CH$_2$CH$_2$CH$_2$NH$_2$ |
| α-methyl-Methionine | —CH$_3$, —CH$_2$CH$_2$SCH$_3$ |
| α-methyl-Phenylalanine | —CH$_3$, —CH$_2$Ph |
| α-methyl-Proline | —CH$_3$, -2-(pyrrolidine) |
| α-methyl-Serine | —CH$_3$, —CH$_2$OH |
| α-methyl-Threonine | —CH$_3$, —CH$_2$CH(OH)(CH$_3$) |
| α-methyl-Tryptophan | —CH$_3$, —CH$_2$-3-(1H-indole) |
| α-methyl-Tyrosine | —CH$_3$, —CH$_2$-(p-hydroxyphenyl) |
| α-methyl-Valine | —CH$_3$, -isopropyl |
| Di-vinyl | —CH=CH$_2$, —CH=CH$_2$ |
| Norleucine | —H, —CH$_2$CH$_2$CH$_2$CH$_3$ |

There are many known unnatural amino acids any of which may be included in the polypeptides of the present invention. See, for example, S. Hunt, *The Non-Protein Amino Acids: In Chemistry and Biochemistry of the Amino*

*Acids*, edited by G. C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine.

Certain unnatural amino acids are included into the polypeptide chain for peptide stapling or stitching. These unnatural amino acids include a terminal unsaturated moiety, such as a double or triple bond. Exemplary amino acids with terminal olefinic unsaturation include, but are not limited to, —(CH$_2$)$_g$—S—(CH$_2$)$_g$CH=CH$_2$; —(CH$_2$)$_g$—O—(CH$_2$)$_g$CH=CH$_2$; —(CH$_2$)$_g$—NH—(CH$_2$)$_g$CH=CH$_2$; —(CH$_2$)$_g$—(C=O)—S—(CH$_2$)$_g$CH=CH$_2$; —(CH$_2$)$_g$—(C=O)—O—(CH$_2$)$_g$CH=CH$_2$; —(CH$_2$)$_g$—(C=O)—NH—(CH$_2$)$_g$CH=CH$_2$; —CH$_2$CH$_2$CH$_2$CH$_2$—NH—(CH$_2$)$_g$CH=CH$_2$; —(C$_6$H$_5$)-p—O—(CH$_2$)$_g$CH=CH$_2$; —CH(CH$_3$)—O—(CH$_2$)$_g$CH=CH$_2$; —CH$_2$CH(—O—CH=CH$_2$)(CH$_3$); -histidine—N((CH$_2$)$_g$CH=CH$_2$); -tryptophan-N((CH$_2$)$_g$CH=CH$_2$); and —(CH$_2$)$_{g+1}$(CH=CH$_2$), wherein each instance of g is, independently, 0 to 10, inclusive. Specific amino acids with terminal unsaturation are further described and depicted herein.

"Protein," "peptide" and "polypeptide" are terms used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. Inventive polypeptides contain unnatural amino acids comprising terminal unsaturated side chains which may be joined via ring closing metathesis to form one or more staples, natural amino acids, and optionally one or more unnatural amino acids such as depicted in Table 2. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

As used herein, the phrase "alpha-helical" refers to a polypeptide or amino acid sequence adopting, on average, backbone (φ, ψ) dihedral angles in a range from about (−90°, −15°) to about (−35°, −70°). Alternatively, the phrase "alpha-helical" refers to a polypeptide adopting dihedral angles such that the ψ dihedral angle of one residue and the φ dihedral angle of the next residue sums, on average, about −80° to about −125°. In certan embodiments, the polypeptide adopts dihedral angles such that the ψ dihedral angle of one residue and the φ dihedral angle of the next residue sums, on average, about −100° to about −110°. In certain embodiments, the polypeptide adopts dihedral angles such that the ψ dihedral angle of one residue and the φ dihedral angle of the next residue sums, on average, about −105°. Furthermore, the phrase "alpha-helical" may also refer to a polypeptide having at least 50%, 60%, 70%, 80%, 90%, or 95% of the amino acids provided in the polypeptide chain in an alpha-helical conformation, and/or with dihedral angles as specified herein. Confirmation of a polypeptide's alpha-helical secondary structure may be ascertained by known analytical techniques, such as x-ray crystallography, electron crystallography, fiber diffraction, fluorescence anisotropy, circular dichroism (CD), and nuclear magnetic resonance (NMR) spectroscopy.

As used herein, the phrase "improved alpha helicity" or "improved alpha helical character" refers to any polypeptide of the present invention which, upon stapling, stabilizes, imparts, or increases alpha helicity to the stapled polypeptide as compared to the unstapled polypeptide, which may or may not be alpha helical. Improved alpha helical character encompasses stapled polypeptides which are characterized as having less than 50% alpha helicity by CD spectroscopy, but are confirmed alpha helical by X-ray or NMR spectroscopy, e.g., adopting, on average, backbone (φ, ψ) dihedral angles in a range from about (−90°, −15°) to about (−35°, −70°) and/or adopting dihedral angles such that the ψ dihedral angle of one residue and the φ dihedral angle of the next residue sums, on average, about −80° to about −125°. In certan embodiments, the stapled polypeptide with improved alpha helicity adopts dihedral angles such that the ψ dihedral angle of one residue and the φ dihedral angle of the next residue sums, on average, about −100° to about −110°. In certain embodiments, the the stapled polypeptide with improved alpha helicity adopts dihedral angles such that the ψ dihedral angle of one residue and the φ dihedral angle of the next residue sums, on average, about −105°.

As used herein, the term "resin" refers to a resin useful for solid phase synthesis. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis,* 2nd edition, Pierce Chemical Company, Rockford, 1984, the entire contents of each of which are hereby incorporated herein by reference.

As used herein, when two entities are "associated with" one another they are linked by a direct or indirect covalent or non-covalent interaction. In certain embodiments, the association is covalent, and the entities are said to be "conjugated" to one another. In other embodiments, the association is non-covalent. Non-covalent interactions include hydrogen bonding, van der Waals interactions, hydrophobic interactions, magnetic interactions, electrostatic interactions, pi stacking, etc. An indirect covalent interaction is when two entities are covalently associated through a linker.

As used herein, a "label" refers to a moiety that has at least one element, isotope, or functional group incorporated into the moiety which enables detection of the inventive polypeptide to which the label is attached. Labels can be directly attached (i.e., via a bond) or can be attached by a tether (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a tether). It will be appreciated that the label may be attached to or incorporated into the inventive polypeptide at any position.

In general, a label can fall into any one (or more) of five classes: a) a label which contains isotopic moieties, which may be radioactive or heavy isotopes, including, but not limited to, $^2$H, $^3$H, $^{13}$C, $^{14}$C, $^{15}$N, $^{18}$F, $^{31}$P, $^{32}$P, $^{35}$S, $^{67}$Ga, $^{76}$Br, $^{99m}$Tc (Tc-99m), $^{111}$In, $^{123}$I, $^{125}$I, $^{131}$I, $^{153}$Gd, $^{169}$Yb and $^{186}$Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluoresceinisothiocyanat (FITC); d) a label which has one or more photo affinity moieties; and e) a label which is a ligand forwith one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluoresceinisothiocyanat (FITC). In certain embodiments, the label comprises a ligand moiety with one or more known binding partners. In certain embodiments, the label comprises biotin.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the animal is a mammal. The animal may be a male or female and at any stage of development. A non-human animal may be a transgenic animal.

"Treat," "treating" and "treatment" contemplate an action that occurs while a subject is suffering from a condition and that reduces the severity of the condition or retards or slows the progression of the condition ("therapeutic treatment"), and also contemplates an action that occurs before a subject begins to suffer from the condition and that inhibits or reduces the severity of the condition ("prophylactic treatment").

As used herein, "condition," "disease," and "disorder" are used interchangeably.

An "effective amount" of a compound of the present invention refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive polypeptide may reduce the tumor burden or stop the growth or spread of a tumor.

A "therapeutically effective amount" of a compound of the present invention is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of the present invention is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

BRIEF DESCRIPTION OF THE DRAWINGS

FIG. 1 depicts a crystal structure of RAB/FIP binding.

FIG. 4A depicts a representative FITC-conjugated stapled FIP peptide containing an N-terminal beta-alanine spacer, a monoethylene glycol spacer, and a fluorescein isothiocyanate (FITC) cap. FIG. 4B describes a panel of stapled FIP peptides (RFPs) with four staple positions highlighted, representing class I (FIP1) and class II (FIP3) RAB family interacting proteins (FIPs) (SEQ ID NOs: 65-74 from top to bottom).

FIG. 7 is a panel of RFPs (RFP14-RFP20) with four staple positions highlighted (SEQ ID NOs: 75-81 from top to bottom).

DETAILED DESCRIPTION OF CERTAIN EMBODIMENTS OF THE INVENTION

Figure 2:
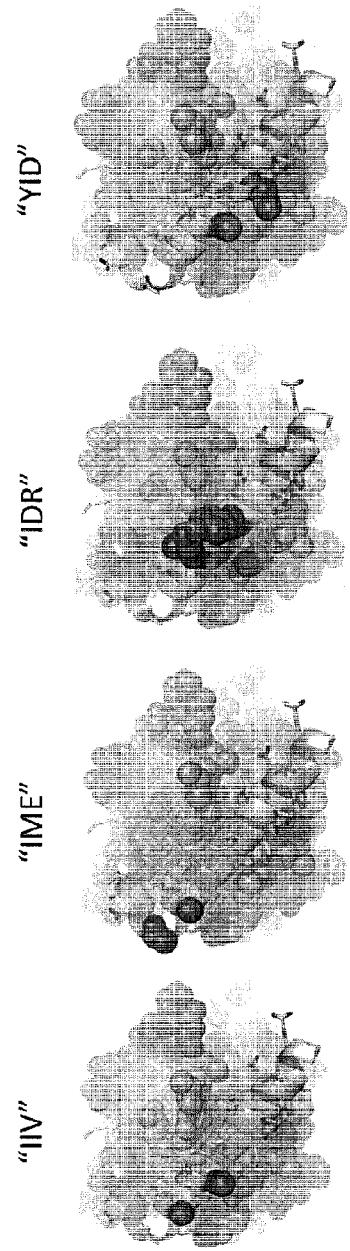
FIG. 2A depicts the $S_5$ alpha-methyl, alpha-pentenyl amino acid sites in FIP1-FIP4 (highlighted in grey, SEQ ID NOs: 61-64 from top to bottom).
FIG. 2B shows four staple positions that were identified. The corresponding residues in FIP3 are labeled dark grey.

Provided herein are inventive polypeptides comprising a modified C-terminal RAB binding domain (RabBD) of Rab family interacting proteins (FIPs) stabilized by peptide stapling or stitching. Also provided herein are methods for modulating RAB function comprising contacting an inventive stapled polypeptide with a RAB protein. RAB proteins regulate protein trafficking, for example, membrane receptor trafficking, through endosomal compartments. In certain embodiments, the inventive stapled polypeptides bind to RAB protein. In certain embodiments, the inventive stapled polypeptides are useful in the treatment of conditions associated with aberrant RAB function, e.g., by inhibition of RAB.

Also provided are synthetic precursors to the inventive stapled polypeptides, also referred to herein as unstapled polypeptides.

Polypeptides

As generally described above, the present invention provides inventive stapled polypeptides, and unstapled precursors thereof. The inventive stapled polypeptides comprise a 26-mer stapled alpha helical amino acid sequence -[$X_{1-26}$]- which, in certain embodiments, binds to RAB protein thereby inhibiting its function. The sequence -[$X_{1-26}$]- comprises one or more staples, e.g., one, two, three, or four staples, wherein the amino acids which participate in the staple are separated by two or more amino acids.

In one aspect, provided is an unstapled polypeptide of Formula (I):

  (I)

or a pharmaceutically acceptable salt thereof;
wherein:
each instance of $X_{AA}$ is a natural amino acid or an unnatural amino acid;
s is 0 or an integer between 1 and 100, inclusive;
t is 0 or an integer between 1 and 100, inclusive;
$R^f$ is an N-terminal group selected from the group consisting of hydrogen; optionally substituted aliphatic; optionally substituted heteroaliphatic; optionally substituted aryl; optionally substituted heteroaryl; acyl; a resin; an amino protecting group; and a label optionally joined by a linker, wherein the linker is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; and acylene;
$R^e$ is a C-terminal group selected from the group consisting of hydrogen; optionally substituted aliphatic; optionally substituted heteroaliphatic; optionally substituted aryl; optionally substituted heteroaryl; —$OR^E$, —$N(R^E)_2$, or —$SR^E$, wherein each instance of $R^E$ is, independently, hydrogen; optionally substituted aliphatic; optionally substituted heteroaliphatic; optionally substituted aryl; optionally substituted heteroaryl; acyl; a resin; a protecting group; or two $R^E$ groups taken together form an optionally substituted heterocyclic or optionally substituted heteroaryl ring;
-[$X_{1-26}$]- is an unstapled amino sequence of the formula:

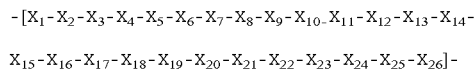

wherein:
$X_1$ is an amino acid selected from the group consisting of Q, H, and I;
$X_2$ is an amino acid selected from the group consisting of V, I, and N;
$X_3$ is an amino acid selected from the group consisting of R and F;
$X_4$ is an amino acid selected from the group consisting of E and R;
$X_5$ is amino acid L;
$X_6$ is an amino acid selected from the group consisting of E, Q, and R;
$X_7$ is an amino acid selected from the group consisting of D, Q, and an amino acid of formula (i);
$X_8$ is an amino acid selected from the group consisting of Y and an amino acid of formula (i);
$X_9$ is an amino acid selected from the group consisting of I and M;
$X_{10}$ is amino acid D;
$X_{11}$ is an amino acid selected from the group consisting of N, R, K, and an amino acid of formula (i) or (ii);
$X_{12}$ is an amino acid selected from the group consisting of L, I, and an amino acid of formula (i) or (ii);
$X_{13}$ is an amino acid selected from the group consisting of L and I;
$X_{14}$ is an amino acid selected from the group consisting of V and L;
$X_{15}$ is an amino acid selected from the group consisting of R, A, and an amino acid of formula (i) or (ii);
$X_{16}$ is an amino acid selected from the group consisting of V and I;
$X_{17}$ is an amino acid selected from the group consisting of M and L;
$X_{18}$ is an amino acid selected from the group consisting of E and D;
$X_{19}$ is an amino acid selected from the group consisting of E, T, H and an amino acid of formula (i);
$X_{20}$ is an amino acid selected from the group consisting of T and N;
$X_{21}$ is amino acid P;
$X_{22}$ is an amino acid selected from the group consisting of N and S;
$X_{23}$ is amino acid I;
$X_{24}$ is amino acid L;
$X_{25}$ is an amino acid selected from the group consisting of R and E;
$X_{26}$ is an amino acid selected from the group consisting of I and V; provided that the amino acid sequence comprises at least two independent occurrences of an amino acid of formula (i) or (ii);
wherein the amino acid of formula (i) is:

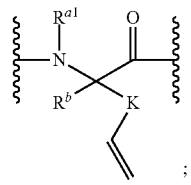

and the amino acid of Formula (ii) is:

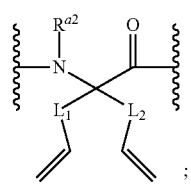

wherein:
each instance of K, $L_1$, and $L_2$, is, independently, optionally substituted alkylene; optionally substituted heteroalkylene; optionally substituted arylene; or optionally substituted heteroarylene;
each instance of $R^{a1}$ and $R^{a2}$ is, independently, hydrogen; optionally substituted aliphatic; optionally substituted heteroaliphatic; optionally substituted aryl; optionally substituted heteroaryl; acyl; or an amino protecting group; and each instance of $R^b$ is, independently, hydrogen; optionally substituted aliphatic; optionally substituted heteroaliphatic; optionally substituted aryl; or optionally substituted heteroaryl.

Stapling of the polypeptide of Formula (I) by ring closing metathesis, and optionally synthetically modifying the resulting double bond of the staple, provides a stapled polypeptide of Formula (II):

$$R^f\text{-}[X_{AA}]_s\text{-}[X_{1\text{-}26}]\text{-}[X_{AA}]_t\text{-}R^e \quad\quad (II)$$

or a pharmaceutically acceptable salt thereof;
wherein:
each instance of $X_{AA}$ is a natural amino acid or unnatural amino acid;
s is 0 or an integer between 1 and 100, inclusive;
t is 0 or an integer between 1 and 100, inclusive;
$R^f$ is an N-terminal group selected from the group consisting of hydrogen; optionally substituted aliphatic; optionally substituted heteroaliphatic; optionally substituted aryl; optionally substituted heteroaryl; acyl; a resin; an amino protecting group; and a label optionally joined by a linker, wherein the linker is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; and acylene;
$R^e$ is a C-terminal group selected from the group consisting of hydrogen; optionally substituted aliphatic; optionally substituted heteroaliphatic; optionally substituted aryl; optionally substituted heteroaryl; —$OR^E$, —$N(R^E)_2$, or —$SR^E$, wherein each instance of $R^E$ is, independently, hydrogen; optionally substituted aliphatic; optionally substituted heteroaliphatic; optionally substituted aryl; optionally substituted heteroaryl; acyl; a resin; a protecting group; or two $R^E$ groups taken together form an optionally substituted heterocyclic or optionally substituted heteroaryl ring; and
-[$X_{1\text{-}26}$]- is a stapled amino sequence of the Formula:

$$-[X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}$$
$$X_{15}\text{-}X_{16}\text{-}X_{17}\text{-}X_{18}\text{-}X_{19}\text{-}X_{20}\text{-}X_{21}\text{-}X_{22}\text{-}X_{23}\text{-}X_{24}\text{-}X_{25}\text{-}X_{26}]\text{-}$$

wherein:
$X_1$ is an amino acid selected from the group consisting of Q, H, and I;
$X_2$ is an amino acid selected from the group consisting of V, I, and N;
$X_3$ is an amino acid selected from the group consisting of R and F;
$X_4$ is an amino acid selected from the group consisting of E and R;
$X_5$ is amino acid L;
$X_6$ is an amino acid selected from the group consisting of E, Q and R;
$X_7$ is an amino acid selected from the group consisting of D and Q, or $X_7$ and $X_{11}$ are stapled amino acids of Formula (iii), or $X_7$, $X_{11}$ and $X_{15}$ are stapled amino acids of Formula (iv);
$X_8$ is amino acid Y, or $X_8$ and $X_{12}$ are stapled amino acids of Formula (iii);
$X_9$ is an amino acid selected from the group consisting of I and M;
$X_{10}$ is amino acid D;

$X_{11}$ is an amino acid selected from the group consisting of N, R, and K, or $X_7$ and $X_{11}$ are stapled amino acids of Formula (iii), or $X_7$, $X_{11}$ and $X_{15}$ are stapled amino acids of Formula (iv), or $X_{11}$, $X_{15}$ and $X_{19}$ are stapled amino acids of Formula (iv);
$X_{12}$ is an amino acid selected from the group consisting of L and I, or $X_8$ and $X_{12}$ are stapled amino acids of Formula (iii), or $X_{12}$ and $X_{15}$ are stapled amino acids of Formula (iii);
$X_{13}$ is an amino acid selected from the group consisting of L and I;
$X_{14}$ is an amino acid selected from the group consisting of V and L;
$X_{15}$ is an amino acid selected from the group consisting of R and A, or $X_{12}$ and $X_{15}$ are stapled amino acids of Formula (iii); or $X_{15}$ and $X_{19}$ are stapled amino acids of Formula (iii), or $X_7$, $X_{11}$, and $X_{15}$ are stapled amino acids of Formula (iv), or $X_{11}$, $X_{15}$, and $X_{19}$ are stapled amino acids of Formula (iv);
$X_{16}$ is an amino acid selected from the group consisting of V and I;
$X_{17}$ is an amino acid selected from the group consisting of M and L;
$X_{18}$ is an amino acid selected from the group consisting of E and D;
$X_{19}$ is E, T, or H, or $X_{15}$ and $X_{19}$ are stapled amino acids of Formula (iii), or $X_{11}$, $X_{15}$, and $X_{19}$ are stapled amino acids of Formula (iv);
$X_{20}$ is an amino acid selected from the group consisting of T and N;
$X_{21}$ is amino acid P;
$X_{22}$ is an amino acid selected from the group consisting of N and S;
$X_{23}$ is amino acid I;
$X_{24}$ is amino acid L;
$X_{25}$ is an amino acid selected from the group consisting of R and E;
$X_{26}$ is an amino acid selected from the group consisting of I and V;
provided that the amino acid sequence comprises at least one occurrence of stapled amino acids of Formula (iii) or (iv);
wherein the stapled amino acids of Formula (iii) is:

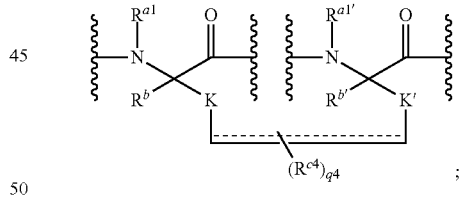

and wherein the stapled amino acids of Formula (iv) is:

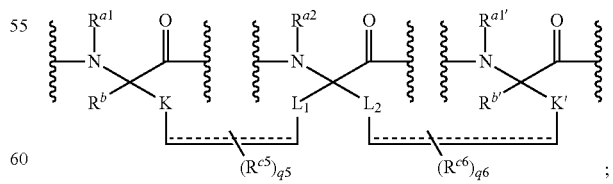

wherein:
each instance of K, K', $L_1$, and $L_2$, is, independently, optionally substituted alkylene; optionally substituted heteroalkylene; optionally substituted arylene; or optionally substituted heteroarylene;

each instance of $R^{a1}$, $R^{a1\prime}$, and $R^{a2}$ is, independently, hydrogen; optionally substituted aliphatic; optionally substituted heteroaliphatic; optionally substituted aryl; optionally substituted heteroaryl; acyl; or an amino protecting group;

each instance of $R^b$ and $R^{b\prime}$ is, independently, hydrogen; optionally substituted aliphatic; optionally substituted heteroaliphatic; optionally substituted aryl; optionally substituted heteroaryl;

each instance of ==== independently represents a single or double bond; P each instance of $R^{c4}$, $R^{c5}$, and $R^{c6}$ is independently hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro; and each instance of $q^{c4}$, $q^{c5}$, and $q^{c6}$ is independently 0, an integer between 1 and 2 when ==== represents a double bond, or an integer between 1 and 4, inclusive, when ==== represents a single bond.

As generally defined above for Formulae (I) and (II), each instance of $X_{AA}$ is independently a natural amino acid or an unnatural amino acid, i.e., of the Formula:

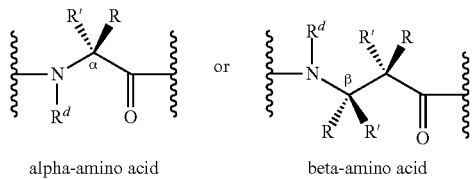

alpha-amino acid    beta-amino acid wherein each instance of R and R' independently are selected from the group consisting of hydrogen, optionally substituted aliphatic, optionally substituted heteroaliphatic, optionally substituted aryl, optionally substituted heteroaryl, and $R^d$ is hydrogen or an amino protecting group. In certain embodiments, $R^d$ is an amino protecting group. In certain embodiments, $R^d$ is hydrogen. In certain embodiments, R and R' are groups as listed in Tables 1 or 2. For example, in certain embodiments, each instance of $X_{AA}$ is independently a natural amino acid (e.g., selected from a natural alpha-amino acid as listed in Table 1 or a natural beta-amino acid, e.g., beta-alanine) or an unnatural amino acid (e.g., selected from an unnatural alpha-amino acid as listed in Table 2). In certain embodiments, each instance of $X_{AA}$ is independently a natural alpha-amino acid or natural beta-amino acid. In certain embodiments, each instance of $X_{AA}$ is independently a natural alpha amino acid as listed in Table 1. In certain embodiments, each instance of $X_{AA}$ is a natural alpha amino acid independently selected from the group consisting of K, E, F, R, D, T, P, A, Y, H, and Q. However, in certain embodiments, at least one instance of $X_{AA}$ is an unnatural amino acid, e.g., an unnatural alpha-amino acid as listed in Table 2.

As generally defined above for Formulae (I) and (II), s and t define the number of amino acids $X_{AA}$ at the N-terminus and C-terminus, respectively. In certain embodiments, s is 0 or an integer between 1 and 50, between 1 and 40, between 1 and 30, between 1 and 20, between 1 and 10, or between 1 and 5 (e.g., 1, 2, 3, 4, or 5), inclusive. In certain embodiments, s is 0, 1, 2, 3, or 4. In certain embodiments, s is 4. In certain embodiments, t is 0 or an integer between 1 and 50, between 1 and 40, between 1 and 30, between 1 and 20, between 1 and 10, or between 1 and 5 (e.g., 1, 2, 3, 4, or 5), inclusive. In certain embodiments, t is 0, 1, 2, 3, or 4. In certain embodiments, t is 1 or 2.

In certain embodiments, $-[X_{AA}]_s-$ corresponds to four amino acids selected from any one of the following sequences:

```
-[K-K-E-F]-;          (SEQ ID NO: 1)

-[E-R-D-T]-;          (SEQ ID NO: 2)

-[K-Q-E-E]-;          (SEQ ID NO: 3)
and

-[E-Q-E-E]-.          (SEQ ID NO: 4)
```

In certain embodiments, $-[X_{AA}]_t-$ corresponds to one to two amino acids selected from any one of the following sequences:

```
-[P-A]-;

-[P-Y]-;

-[K]-;
and

-[K-H]-.
```

As generally defined above for Formulae (I) and (II), $R^f$ is an N-terminal group selected from the group consisting of hydrogen; optionally substituted aliphatic; optionally substituted heteroaliphatic; optionally substituted aryl; optionally substituted heteroaryl; acyl; a resin; an amino protecting group; and a label optionally joined by a linker, wherein the linker is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; and acylene, or a combination thereof.

In certain embodiments, $R^f$ is hydrogen (e.g., to provide an $-NH(R^d)$ terminal group). In certain embodiments, $R^f$ is optionally substituted aliphatic (e.g., $-CH_3$, $-CH_2CH_3$). In certain embodiments, $R^f$ is optionally substituted heteroaliphatic. In certain embodiments, $R^f$ is optionally substituted aryl. In certain embodiments, $R^f$ is optionally substituted heteroaryl. In certain embodiments, $R^f$ is acyl (e.g., acetyl $(-COCH_3)$). In certain embodiments, $R^f$ is a resin. In certain embodiments, $R^f$ is an amino protecting group (e.g., -Boc, -Fmoc).

In certain embodiments, $R^f$ comprises a label optionally joined by a linker to the polypeptide, wherein the linker is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; and acylene, or a combination thereof. Exemplary labels include, but are not limited to FITC and biotin:

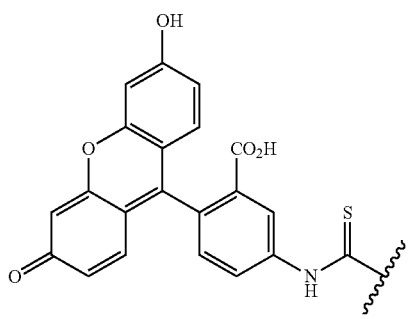
FITC

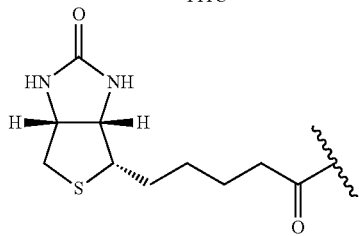
Biotin

In certain embodiments, $R^f$ is a label directly joined to the polypeptide (i.e., through a bond). In certain embodiments, $R^f$ is a label indirectly joined to the inventive polypeptide through a linker, wherein the linker is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; and acylene, or a combination thereof.

In certain embodiments, the linker joinging the label to the polypeptide is a optionally substituted alkylene. In certain embodiments, the linker is an optionally substituted alkenylene. In certain embodiments, the linker is an optionally substituted alkynylene. In certain embodiments, the linker is an optionally substituted heteroalkylene. In certain embodiments, the linker is an optionally substituted heteroalkenylene. In certain embodiments, the linker is an optionally substituted heteroalkynylene. In certain embodiments, the linker is an optionally substituted arylene. In certain embodiments, the linker is an optionally substituted heteroarylene. In certain embodiments, the linker is an optionally substituted acylene.

In certain embodiments, the linker is an optionally substituted heteroalkylene selected from the group consisting of:

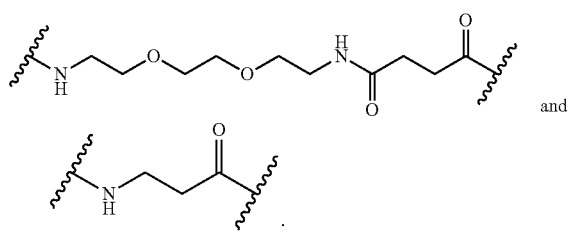

and

As generally defined above for Formula (I) and (II), $R^e$ is a C-terminal group selected from the group consisting of hydrogen; optionally substituted aliphatic; optionally substituted heteroaliphatic; optionally substituted aryl; optionally substituted heteroaryl; $-OR^E$, $-N(R^E)_2$, or $-SR^E$, wherein each instance of $R^E$ is, independently, hydrogen; optionally substituted aliphatic; optionally substituted heteroaliphatic; optionally substituted aryl; optionally substituted heteroaryl; acyl; a resin; a protecting group; or two $R^E$ groups taken together form an optionally substituted heterocyclic or optionally substituted heteroaryl ring.

In certaine embodiments, $R^e$ is hydrogen, e.g., to provide an aldehyde (—CHO) as the C-terminal group. In certain embodiments, $R^e$ is optionally substituted aliphatic; optionally substituted heteroaliphatic; optionally substituted aryl; or optionally substituted heteroaryl in order to provide a ketone as the C-terminal group.

In certain embodiments, $R^e$ is $-OR^E$, and $R^E$ is hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a hydroxyl protecting group, e.g., to provide a carboxylic acid or ester C-terminal group.

In certain embodiments, $R^e$ is $-SR^E$, and $R^E$ is hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a suitable thiol protecting group, e.g., to provide a thioacid or thioester C-terminal group.

In certain embodiments, $R^e$ is $-N(R^E)_2$, and each instance of $R^E$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; an amino protecting group; or two $R^E$ groups together form a substituted or unsubstituted 5- to 6-membered heterocyclic or heteroaromatic ring, e.g., to provide an amide as the C-terminal group.

As generally defined above for Formulae (I) or (II), the group -[$X_{1-26}$]- refers to an amino acid sequence wherein the amino acid sequence comprises at least two amino acids which are capable of forming, or have together formed, a staple. Such amino acids may be present at positions $X_7$, $X_8$, $X_{11}$, $X_{12}$, $X_{15}$, and $X_{19}$ of the sequence and correspond to an amino acid of Formula (i) or (ii), or a stapled amino acids of Formula (iii) or (iv). The other amino acids in the sequence, e.g., $X_{1-6}$, $X_9$, $X_{10}$, $X_{13}$, $X_{14}$, $X_{16-18}$, and $X_{20-26}$, cannot participate or have not participated in the staple forming reaction.

In certain embodiments, -[$X_1$-$X_2$]- is -[I-N]-. In certain embodiments, -[$X_1$-$X_2$]- is -[Q-V]-. In certain embodiments, -[$X_1$-$X_2$]- is -[H-I]-.

In certain embodiments, -[$X_1$-$X_2$-$X_3$-$X_4$]- is -[I-N-F-R]- (SEQ ID NO: 5). In certain embodiments, -[$X_1$-$X_2$-$X_3$-$X_4$]- is -[Q-V-R-E]- (SEQ ID NO: 85). In certain embodiments, -[$X_1$-$X_2$-$X_3$-$X_4$]- is -[H-I-R-E]- (SEQ ID NO: 6).

In certain embodiments, -[$X_3$-$X_4$-$X_5$-$X_6$]- is -[R-E-L-E]- (SEQ ID NO: 7). In certain embodiments, -[$X_3$-$X_4$-$X_5$]- is -[R-E-L]-. In certain embodiments, -[$X_3$-$X_4$-$X_5$-$X_6$]- is -[F-R-L-Q]- (SEQ ID NO: 87). In certain embodiments, -[$X_3$-$X_4$-$X_5$-$X_6$]- is -[F-R-L-R]- (SEQ ID NO: 8). In certain embodiments, -[$X_3$-$X_4$-$X_5$]- is -[F-R-L]-.

In certain embodiments, -[$X_9$]- is -[I]-. In certain embodiments, -[$X_9$]- is -[M]-. In certain embodiments, -[$X_9$-$X_{10}$]- is -[I-D]-. In certain embodiments, -[$X_9$-$X_{10}$]- is -[M-D]-.

In certain embodiments, -[$X_{13}$]- is -[L]-. In certain embodiments, -[$X_{13}$]- is -[I]-. In certain embodiments, -[$X_{14}$]- is -[V]-. In certain embodiments, -[$X_{14}$]- is -[L]-. In certain embodiments, -[$X_{13}$-$X_{14}$]- is -[L-V]-. In certain embodiments, -[$X_{13}$-$X_{14}$]- is -[I-V]-. In certain embodiments, -[$X_{13}$-$X_{14}$]- is -[U-L]-.

In certain embodiments, -[$X_{16}$-$X_{17}$-$X_{18}$]- is -[V-M-E]-. In certain embodiments, -[$X_{16}$-$X_{17}$-$X_{18}$]- is -[I-M-E]-. In certain embodiments, -[$X_{16}$-$X_{17}$-$X_{18}$]- is -[I-L-D]-. In certain embodiments, -[$X_{17}$-$X_{18}$]- is -[M-E]-. In certain embodiments, -[$X_{17}$-$X_{18}$]- is -[L-D]-.

In certain embodiments, -[$X_{20}$]- is -[T]-. In certain embodiments, -[$X_{20}$]- is -[P]-. In certain embodiments, -[$X_{20}$-$X_{21}$]- is -[T-P]-. In certain embodiments, -[$X_{20}$-$X_{21}$]- is -[N-P]-.

In certain embodiments, -[$X_{22}$-$X_{23}$-$X_{24}$]- is -[N-I-L]-. In certain embodiments, -[$X_{22}$-$X_{23}$-$X_{24}$]- is -[S-I-L]-.

In certain embodiments, -[$X_{25}$-$X_{26}$]- is -[R-I]-. In certain embodiments, -[$X_{25}$-$X_{26}$]- is -[R-V]-. In certain embodiments, -[$X_{25}$-$X_{26}$]- is -[E-V]-. In certain embodiments, -[$X_{25}$-$X_{26}$]- is -[E-I]-.

As generally defined above, the polypeptide of Formula (I) is an unstapled polypeptide and may independently comprise amino acids of the Formula (i) at positions $X_7$, $X_8$, and $X_{19}$ of the sequence, and amino acids of the Formula (i) or (ii) at positions $X_{11}$, $X_{12}$, and $X_{15}$ of the sequence:

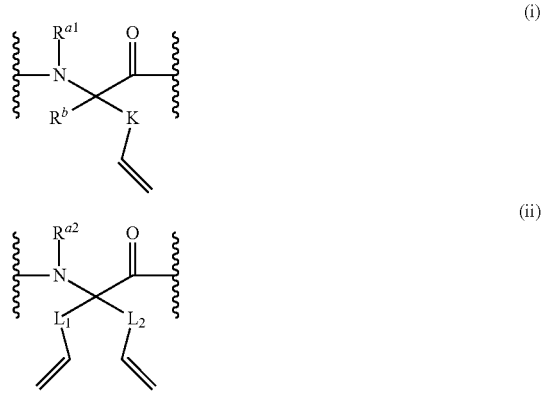

wherein:

each instance of K, $L_1$, and $L_2$, is, independently, optionally substituted alkylene or optionally substituted heteroalkylene; optionally substituted arylene; or optionally substituted heteroarylene;

each instance of $R^{a1}$ and $R^{a2}$ is, independently, hydrogen; optionally substituted aliphatic; optionally substituted heteroaliphatic; optionally substituted aryl; optionally substituted heteroaryl; acyl; or an amino protecting group; and each instance of $R^b$ is, independently, hydrogen; optionally substituted aliphatic; optionally substituted heteroaliphatic; optionally substituted aryl; or optionally substituted heteroaryl.

In certain embodiments, the amino acid sequence comprises at least two independent occurrences of an amino acid of Formula (i) or (ii) separated by two or three amino acids. In certain embodiments, the amino acid sequence comprises at least two independent occurrences of an amino acid of Formula (i) or (ii) separated by two amino acids. In certain embodiments, the amino acid sequence comprises at least two independent occurrences of an amino acid of Formula (i) or (ii) separated by three amino acids. In certain embodiments, the amino acid sequence comprises two independent occurrences of an amino acid of Formula (i) separated by two amino acids. In certain embodiments, the amino acid sequence comprises two independent occurrences of an amino acid of Formula (i) separated by three amino acids. In certain embodiments, the amino acid sequence comprises two independent occurrences of an amino acid of Formula (i) separated by three amino acids from one occurrence of an amino acid of Formula (ii).

In certain embodiments, when $X_7$ is an amino acid of Formula (i) then $X_{11}$ is an amino acid of Formula (i) and $X_8$ is not an amino acid of Formula (i).

In certain embodiments, when $X_8$ is an amino acid of Formula (i) then $X_{12}$ is an amino acid of Formula (i), and $X_7$ is not an amino acid of Formula (i).

In certain embodiments, when $X_{11}$ is an amino acid of Formula (i) then $X_7$ or $X_{15}$ is an amino acid of Formula (i) and $X_8$ and $X_{12}$ are not amino acids of Formula (i).

In certain embodiments, when $X_{11}$ is an amino acid of Formula (ii) then $X_7$ is an amino acid of Formula (i) and $X_{15}$ is an amino acid of Formula (i), and $X_8$ and $X_{12}$ are not amino acids of Formula (i).

In certain embodiments, when $X_{12}$ is an amino acid of Formula (i) then $X_8$ or $X_{15}$ is an amino acid of Formula (i), and $X_{11}$ is not an amino acid of Formula (i) or (ii).

In certain embodiments, when $X_{15}$ is an amino acid of Formula (i) then $X_{11}$, $X_{12}$, or $X_{19}$ is an amino acid of Formula (i); and when $X_{15}$ is an amino acid of Formula (ii) then $X_{11}$ and $X_{19}$ are each independently an amino acid of Formula (i).

In certain embodiments, when $X_{19}$ is an amino acid of Formula (i) then $X_{15}$ is an amino acid of Formula (i), or $X_{15}$ is an amino acid of Formula (ii) and $X_{11}$ is an amino acid of Formula (i).

In certain embodiments, K is optionally substituted alkylene. In certain embodiments, K is optionally substituted heteroalkylene. In certain embodiments, K is optionally substituted arylene. In certain embodiments, K is optionally substituted heteroarylene. In certain embodiments, K is optionally substituted $C_{1-6}$ alkylene, e.g., optionally substituted $C_{2-6}$ alkylene, optionally substituted $C_{3-6}$ alkylene, optionally substituted $C_{4-6}$ alkylene, optionally substituted $C_{5-6}$ alkylene, optionally substituted $C_2$ alkylene, optionally substituted $C_3$ alkylene, optionally substituted $C_4$ alkylene, optionally substituted $C_5$ alkylene, or an optionally substituted $C_6$ alkylene. In certain embodiments, K is an unsubstituted group. For example, in certain embodiments, K is an unsubstituted $C_{1-6}$ alkylene, e.g., unsubstituted $C_{2-6}$ alkylene, unsubstituted $C_{3-6}$ alkylene, unsubstituted $C_{4-6}$ alkylene, unsubstituted $C_{5-6}$ alkylene, unsubstituted $C_2$ alkylene, unsubstituted $C_3$ alkylene, unsubstituted $C_4$ alkylene, unsubstituted $C_5$ alkylene, or an unsubstituted $C_6$ alkylene.

In certain embodiments, each instance of $L_1$ and $L_2$ is independently optionally substituted alkylene. In certain embodiments, each instance of $L_1$ and $L_2$ is independently optionally substituted heteroalkylene. In certain embodiments, each instance of $L_1$ and $L_2$ is independently optionally substituted arylene. In certain embodiments, each instance of $L_1$ and $L_2$ is independently optionally substituted heteroarylene. In certain preferred embodiments, each instance of $L_1$ and $L_2$ is independently optionally substituted $C_{1-6}$ alkylene, e.g., optionally substituted $C_{2-6}$ alkylene, optionally substituted $C_{3-6}$ alkylene, optionally substituted $C_{4-6}$ alkylene, optionally substituted $C_{5-6}$ alkylene, optionally substituted $C_2$ alkylene, optionally substituted $C_3$ alkylene, optionally substituted $C_4$ alkylene, optionally substituted $C_5$ alkylene, or an optionally substituted $C_6$ alkylene. In certain embodiments, each instance of $L_1$ and $L_2$ is independently is an unsubstituted group. For example, in certain embodiments, each instance of $L_1$ and $L_2$ is independently is an unsubstituted $C_{1-6}$ alkylene, e.g., unsubstituted $C_{2-6}$ alkylene, unsubstituted $C_{3-6}$ alkylene, unsubstituted $C_{4-6}$ alkylene, unsubstituted $C_{5-6}$ alkylene, unsubstituted $C_2$ alkylene, unsubstituted $C_3$ alkylene, unsubstituted $C_4$ alkylene, unsubstituted $C_5$ alkylene, or an unsubstituted $C_6$ alkylene. In certain embodiments, each instance of $L_1$ and $L_2$ is the same. In certain embodiments, each instance of $L_1$ and $L_2$ is different.

In certain embodiments, each instance of $R^{a1}$ and $R^{a2}$ is, independently, hydrogen, acyl, or an amino protecting group. In certain embodiments, each instance of $R^{a1}$ and $R^{a2}$ is hydrogen.

In certain embodiments, each instance of $R^b$ is, independently hydrogen or optionally substituted aliphatic. In certain embodiments, each instance of $R^b$ is hydrogen or $C_{1-6}$alkyl. In certain embodiments, each instance of $R^b$ is hydrogen or —$CH_3$.

In certain embodiments, the amino acid of Formula (i) is selected from the group consisting of:

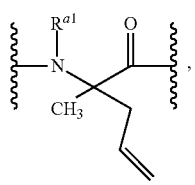

$A_3$

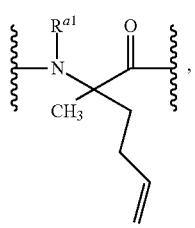

$A_4$

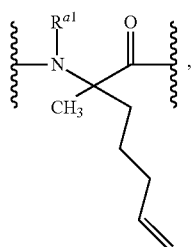

$A_5$

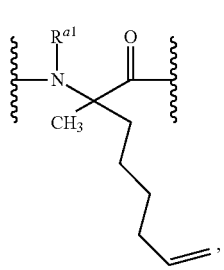

$A_6$

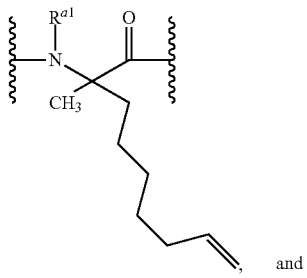

$A_7$ and

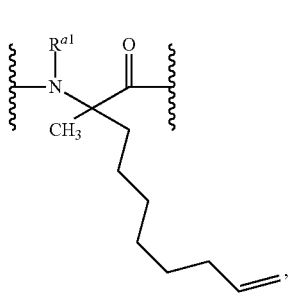

$A_8$

In certain embodiments, each instance of the amino acid of Formula (i) is $A_5$. In certain embodiments, each instance of the amino acid of Formula (i) is $A_8$.

In certain embodiments, the alpha carbon of the amino acid of Formula (i) is in the (S) configuration. In certain embodiments, the alpha carbon of the amino acid of Formula (i) is in the (R) configuration.

In certain embodiments, the amino acid of Formula (i) is selected from the group consisting of:

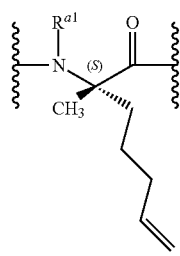

S-$A_5$ (S)-2-amino-2-methylhept-6-enoic acid,

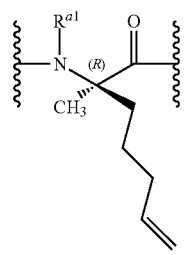

R-$A_5$ (R)-2-amino-2-methylhept-6-enoic acid,

S-A8

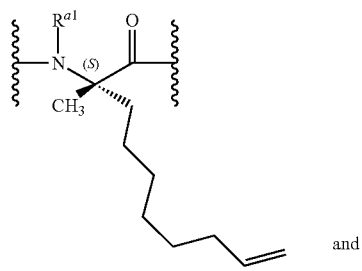

(S)-2-amino-2-methyldec-9-enoic acid,

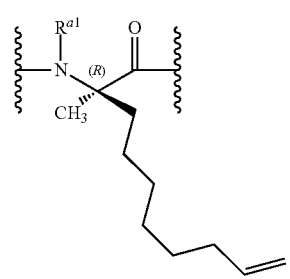

(R)-2-amino-2-methyldec-9-enoic acid.

In certain embodiments, each instance of the amino acid of Formula (i) is S-A$_5$ (also referred to herein as S$_5$). In certain embodiments, each instance of the amino acid of Formula (i) is S-A$_8$ (also referred to herein as S$_8$).

Exemplary amino acids of Formula (ii) include, but are not limited to,

B$_3$

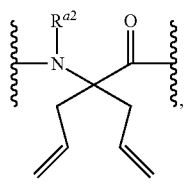

B$_4$

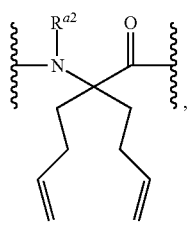

B$_5$

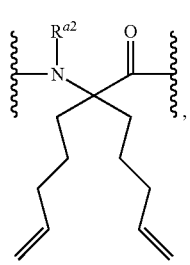

R-A$_8$

B$_6$

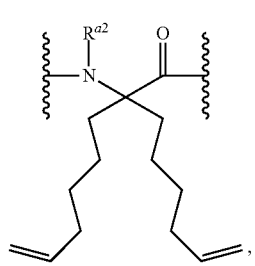

B$_7$

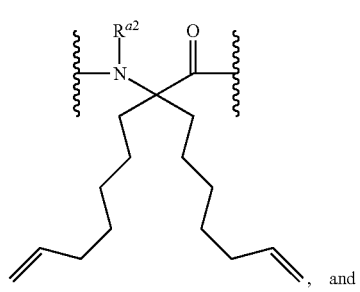

, and

B$_8$

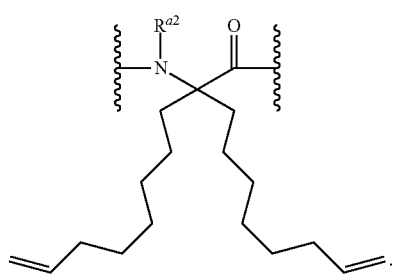

.

In certain embodiments, each instance of the amino acid of Formula (ii) is B$_5$.

In certain embodiments, each instance of the amino acid of Formula (i) is A$_5$ and each instance of the amino acid of Formula (ii) is B$_5$. In certain embodiments, each instance of the amino acid of Formula (i) is S-A$_5$ and each instance of the amino acid of Formula (ii) is B$_5$.

As generally defined above, the polypeptide of Formula (II) is a stapled polypeptide and may independently comprise stapled amino acids of Formula (iii) at $X_7$, $X_8$, $X_{11}$, $X_{12}$, $X_{15}$, and/or $X_{19}$ of the sequence, and/or stapled amino acids of Formula (iv) at $X_{11}$, $X_{12}$, or $X_{15}$ of the sequence:

(iii)

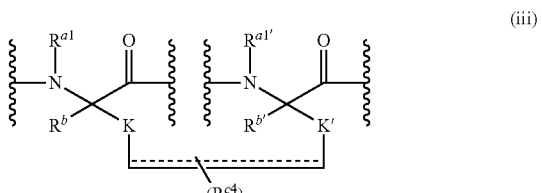

(iv)

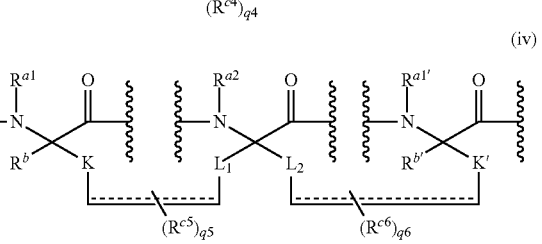

wherein:

each instance of K, K', $L_1$, and $L_2$, is, independently, optionally substituted alkylene; optionally substituted heteroalkylene; optionally substituted arylene; or optionally substituted heteroarylene;

each instance of $R^{a1}$, $R^{a1\prime}$, and $R^{a2}$ is, independently, hydrogen; optionally substituted aliphatic; optionally substituted heteroaliphatic; optionally substituted aryl; optionally substituted heteroaryl; acyl; or an amino protecting group;

each instance of $R^b$ and $R^{b\prime}$ is, independently, hydrogen; optionally substituted aliphatic; optionally substituted heteroaliphatic; optionally substituted aryl; optionally substituted heteroaryl;

each instance of ==== independently represents a single or double bond;

each instance of $R^{c4}$, $R^{c5}$, and $R^{c6}$ is independently hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro; and each instance of $q^{c4}$, $q^{c5}$, and $q^{c6}$ is independently 0, 1, or 2 when ==== represents a double bond, or an integer between 1 and 4, inclusive, when ==== represents a single bond.

In certain embodiments, each instance of K and K' is independently optionally substituted alkylene. In certain embodiments, each instance of K and K' is independently optionally substituted heteroalkylene. In certain embodiments, each instance of K and K' is independently optionally substituted arylene. In certain embodiments, each instance of K and K' is independently optionally substituted heteroarylene. In certain embodiments, each instance of K and K' is independently optionally substituted $C_{1-6}$ alkylene, e.g., optionally substituted $C_{2-6}$ alkylene, optionally substituted $C_{3-6}$ alkylene, optionally substituted $C_{4-6}$ alkylene, optionally substituted $C_{5-6}$ alkylene, optionally substituted $C_2$ alkylene, optionally substituted $C_3$ alkylene, optionally substituted $C_4$ alkylene, optionally substituted $C_5$ alkylene, or an optionally substituted $C_6$ alkylene. In certain embodiments, each instance of K and K' is independently an unsubstituted group. For example, in certain embodiments, each instance of K and K' is independently an unsubstituted $C_{1-6}$ alkylene, e.g., unsubstituted $C_{2-6}$ alkylene, unsubstituted $C_{3-6}$ alkylene, unsubstituted $C_{4-6}$ alkylene, unsubstituted $C_{5-6}$ alkylene, unsubstituted $C_2$ alkylene, unsubstituted $C_3$ alkylene, unsubstituted $C_4$ alkylene, unsubstituted $C_5$ alkylene, or an unsubstituted $C_6$ alkylene.

In certain embodiments, each instance of $L_1$ and $L_2$ is independently optionally substituted alkylene. In certain embodiments, each instance of $L_1$ and $L_2$ is independently optionally substituted heteroalkylene. In certain embodiments, each instance of $L_1$ and $L_2$ is independently optionally substituted arylene. In certain embodiments, each instance of $L_1$ and $L_2$ is independently optionally substituted heteroarylene. In certain preferred embodiments, each instance of $L_1$ and $L_2$ is independently optionally substituted $C_{1-6}$ alkylene, e.g., optionally substituted $C_{2-6}$ alkylene, optionally substituted $C_{3-6}$ alkylene, optionally substituted $C_{4-6}$ alkylene, optionally substituted $C_{5-6}$ alkylene, optionally substituted $C_2$ alkylene, optionally substituted $C_3$ alkylene, optionally substituted $C_4$ alkylene, optionally substituted $C_5$ alkylene, or an optionally substituted $C_6$ alkylene.

In certain embodiments, each instance of $L_1$ and $L_2$ is independently is an unsubstituted group. For example, in certain embodiments, each instance of $L_1$ and $L_2$ is independently is an unsubstituted $C_{1-6}$ alkylene, e.g., unsubstituted $C_{2-6}$ alkylene, unsubstituted $C_{3-6}$ alkylene, unsubstituted $C_{4-6}$ alkylene, unsubstituted $C_{5-6}$ alkylene, unsubstituted $C_2$ alkylene, unsubstituted $C_3$ alkylene, unsubstituted $C_4$ alkylene, unsubstituted $C_5$ alkylene, or an unsubstituted $C_6$ alkylene. In certain embodiments, each instance of $L_1$ and $L_2$ is the same. In certain embodiments, each instance of $L_1$ and $L_2$ is different.

In certain embodiments, each instance of $R^{a1}$, $R^{a1\prime}$, and $R^{a2}$ is, independently, hydrogen, acyl, or an amino protecting group. In certain embodiments, each instance of $R^{a1}$, $R^{a1\prime}$, and $R^{a2}$ is hydrogen.

In certain embodiments, each instance of $R^b$ and $R^{b\prime}$ is, independently, hydrogen or optionally substituted aliphatic. In certain embodiments, each instance of $R^b$ and $R^{b\prime}$ is, independently, hydrogen or $C_{1-6}$alkyl. In certain embodiments, each instance of $R^b$ and $R^{b\prime}$ is, independently, hydrogen or —$CH_3$.

In certain embodiments, each instance of ==== independently represents a single bond.

In certain embodiments, each instance of ==== independently represents a double bond.

In certain embodiments, each instance of $R^{c4}$, $R^{c5}$, and $R^{c6}$ is independently hydrogen, and each instance of $q^{c4}$, $q^{c5}$, and $q^{c6}$ is 0.

In certain embodiments, each instance of $q^{c4}$, $q^{c5}$, and $q^{c6}$ is independently 0, 1, or 2 when ==== represents a double bond.

In certain embodiments, each instance of $q^{c4}$, $q^{c5}$, and $q^{c6}$ is independently 0 or an integer between 1 and 4, inclusive, (i.e., 1, 2, 3, or 4) when ==== represents a single bond.

In certain embodiments, the amino acid of Formula (iii) corresponds to the group:

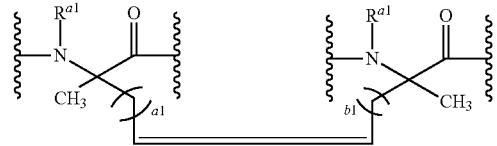

wherein a1 and b1 are an integer between 1 and 6, inclusive. In certain embodiments, both a1 and b1 are 1. In certain embodiments, both a1 and b1 are 2. In certain embodiments, both a1 and b1 are 3. In certain embodiments, both a1 and b1 are 4. In certain embodiments, both a1 and b1 are 5. In certain embodiments, both a1 and b1 are 6. As used herein, when both a1 and b1 are 3, the amino acids are both referred to as stapled $A_5$-$A_5$. As used herein, when both a1 and b1 are 6, the amino acids are both referred to as stapled $A_8$-$A_8$.

In certain embodiments, the amino acid of Formula (iv) corresponds to the group:

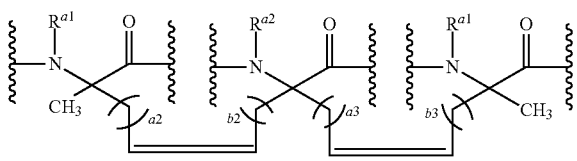

wherein each instance of a2, b2, a3, and b3 is independently an integer between 1 and 6 inclusive. In certain embodiments, each instance of a2, b2, a3, and b3 are 1. In certain embodiments, each instance of a2, b2, a3, and b3 are 2. In certain embodiments, each instance of a2, b2, a3, and b3 are 3. In certain embodiments, each instance of a2, b2, a3, and b3 are 4. In certain embodiments, each instance of a2, b2, a3, and b3 are 5. In certain embodiments, each instance of a2, b2, a3, and b3 are 6. As used herein, when each instance of a2, b2, a3, and b3 is 3, the amino acids are both referred to as stapled $A_5$-$B_5$-$A_5$. As used herein, when each instance of a2, b2, a3, and b3 is 6, the amino acids are both referred to as stapled $A_8$-$B_8$-$A_8$.

In certain embodiments, the amino acid sequence -[$X_{1-26}$]- is alpha helical. In certain embodiments, the unstapled amino acid sequence -[$X_{1-26}$]- is alpha helical. In certain embodiments, the stapled amino acid sequence -[$X_{1-26}$]- is alpha helical. In certain embodiments, stapling the amino acid sequence -[$X_{1-26}$]- results in improved alpha helicity.

In certain embodiments, the amino acid sequence -[$X_{1-26}$]- comprises a RAB binding domain.

In certain embodiments, the amino acid sequence -[$X_{1-26}$]- is a modified amino acid sequence corresponding to residues 1247-1272 of Fip1:

[SEQ ID NO: 9]
-Q-V-R-E-L-E-$X_7$-$X_8$-I-D-$X_{11}$-$X_{12}$-L-V-$X_{15}$-V-M-E-$X_{19}$-T-P-N-I-L-R-I-.

In certain embodiments, the amino acid sequence -[$X_{1-26}$]- is a modified amino acid sequence corresponding to residues 473-498 of Fip2:

[SEQ ID NO: 10]
-H-I-R-E-L-E-$X_7$-$X_8$-I-D-$X_{11}$-$X_{12}$-L-V-$X_{15}$-V-M-E-$X_{19}$-T-P-S-I-L-R-V-.

In certain embodiments, the amino acid sequence -[$X_{1-26}$]- is a modified amino acid sequence corresponding to residues 730-757 of Fip3:

[SEQ ID NO: 11]
-I-N-F-R-L-Q-$X_7$-$X_8$-I-D-$X_{11}$-$X_{12}$-I-V-$X_{15}$-I-M-E-$X_{19}$-N-P-S-I-L-E-V-.

In certain embodiments, the amino acid sequence -[$X_{1-26}$]- is a modified amino acid sequence corresponding to residues 610-635 of Fip4:

[SEQ ID NO: 12]
-I-N-F-R-L-R-$X_7$-$X_8$-M-D-$X_{11}$-$X_{12}$-I-L-$X_{15}$-I-L-D-$X_{19}$-N-P-S-I-L-E-I-.

In certain embodiments of Formula (I) and (II), the the group -[$X_{1-26}$]- corresponds to any one of the following amino acid sequences:

(SEQ ID NO: 13; Fip 1 $X_7$-$X_{11}$; "YID")
-Q-V-R-E-L-E-*-Y-I-D-*-L-L-V-R-V-M-E-E-T-P-N-I-L-R-I-;

(SEQ ID NO: 14; Fip 1 $X_8$-$X_{12}$; "IDN")
-Q-V-R-E-L-E-D-*-I-D-N-*-L-V-R-V-M-E-E-T-P-N-I-L-R-I-;

(SEQ ID NO: 15; Fip 1 $X_{11}$-$X_{15}$; "LLV")
-Q-V-R-E-L-E-D-Y-I-D-*-L-L-V-*-V-M-E-E-T-P-N-I-L-R-I-;

(SEQ ID NO: 16; Fip 1 $X_{15}$-$X_{19}$ "VME")
-Q-V-R-E-L-E-D-Y-I-D-N-L-L-V-*-V-M-E-*-T-P-N-I-L-R-I-;

(SEQ ID NO: 17; Fip 1 $X_7$-$X_{11}$-$X_{15}$)
-Q-V-R-E-L-E-*-Y-I-D-^-L-L-V-*-V-M-E-E-T-P-N-I-L-R-I-;

(SEQ ID NO: 18; Fip 1 $X_{11}$-$X_{15}$-$X_{19}$)
-Q-V-R-E-L-E-D-Y-I-D-*-L-L-V-^-V-M-E-*-T-P-N-I-L-R-I-;

(SEQ ID NO: 19; Fip 2 $X_7$-$X_{11}$ "YID")
-H-I-R-E-L-E-*-Y-I-D-*-L-L-V-R-V-M-E-E-T-P-S-I-L-R-V-;

(SEQ ID NO: 20; Fip 2 $X_8$-$X_{12}$ "IDN")
-H-I-R-E-L-E-D-*-I-D-N-*-L-V-R-V-M-E-E-T-P-S-I-L-R-V-;

(SEQ ID NO: 21; Fip 2 $X_{11}$-$X_{15}$ "LLV")
-H-I-R-E-L-E-D-Y-I-D-*-L-L-V-*-V-M-E-R-T-P-S-I-L-R-V-;

(SEQ ID NO: 22; Fip 2 $X_{15}$-$X_{19}$ "VME")
-H-I-R-E-L-E-D-Y-I-D-N-L-L-V-*-V-M-E-*-T-P-S-I-L-R-V-;

(SEQ ID NO: 23; Fip 2 $X_7$-$X_{11}$-$X_{15}$)
-H-I-R-E-L-E-*-Y-I-D-^-L-L-V-*-V-M-E-E-T-P-S-I-L-R-V-;

(SEQ ID NO: 24; Fip 2 $X_{11}$-$X_{15}$-$X_{19}$)
-H-I-R-E-L-E-D-Y-I-D-*-L-L-V-^-V-M-E-*-T-P-S-I-L-R-V-;

(SEQ ID NO: 25; Fip 3 $X_7$-$X_{11}$ "YID")
-I-N-F-R-L-Q-*-Y-I-D-*-I-I-V-A-I-M-E-T-N-P-S-I-L-E-V-;

(SEQ ID NO: 26; Fip 3 $X_8$-$X_{12}$ "IDR")
-I-N-F-R-L-Q-D-*-I-D-R-*-I-V-A-I-M-E-T-N-P-S-I-L-E-V-;

(SEQ ID NO: 27; Fip 3 $X_{11}$-$X_{15}$ "IIV")
-I-N-F-R-L-Q-D-Y-I-D-*-I-I-V-*-I-M-E-T-N-P-S-I-L-E-V-;

(SEQ ID NO: 28; Fip 3 $X_{15}$-$X_{19}$ "IME")
-I-N-F-R-L-Q-D-Y-I-D-R-I-I-V-*-I-M-E-*-N-P-S-I-L-E-V-;

(SEQ ID NO: 29; Fip 3 $X_7$-$X_{11}$-$X_{15}$)
-I-N-F-R-L-Q-*-Y-I-D-^-I-I-V-*-I-M-E-T-N-P-S-I-L-E-V-;

-continued (SEQ ID NO: 30; Fip 3 $X_{11}$-$X_{15}$-$X_{19}$)
-I-N-F-R-L-Q-D-Y-I-D-*-I-I-V-^-I-M-E-*-N-P-S-I-
L-E-V-;

(SEQ ID NO: 31; Fip 4 $X_7$-$X_{11}$ "YMD")
-I-N-F-R-L-R-*-Y-M-D-*-I-I-L-A-I-L-D-H-N-P-S-I-
L-E-I-;

(SEQ ID NO: 32; Fip 4 $X_8$-$X_{12}$ "MDK")
-I-N-F-R-L-R-Q-*-M-D-K-*-I-L-A-I-L-D-H-N-P-S-I-
L-E-I-;

(SEQ ID NO: 33; Fip 4 $X_{11}$-$X_{15}$ "IIL")
-I-N-F-R-L-R-Q-Y-M-D-*-I-I-L-*-I-L-D-H-N-P-S-I-
L-E-I-;

(SEQ ID NO: 34; Fip 4 $X_{15}$-$X_{19}$ "ILD")
-I-N-F-R-L-R-Q-Y-M-D-K-I-I-L-*-I-L-D-*-N-P-S-I-
L-E-I-;

(SEQ ID NO: 35; Fip 4 $X_7$-$X_{11}$-$X_{15}$)
-I-N-F-R-L-R-*-Y-M-D-^-I-I-L-*-I-L-D-H-N-P-S-I-
L-E-I-;

(SEQ ID NO: 36; Fip 4 $X_{11}$-$X_{15}$-$X_{19}$)
-I-N-F-R-L-R-Q-Y-M-D-*-I-I-L-^-I-L-D-*-N-P-S-I-
L-E-I-.

wherein the amino acid sequence corresponds to an unstapled amino acid sequence if:
(1) the amino acid sequence comprises two amino acids symbolized by an asterix (*), and each instance of the symbol (*) independently corresponds to an amino acid of the Formula (i); or
(2) the amino acid sequence comprises an amino acid symbolized by a carrot (^) and two amino acids symbolized by the asterix (*), and each instance of the symbol (^) corresponds to an amino acid of Formula (ii) and each instance of the symbol (*) independently corresponds to the amino acid of (i);

and wherein the amino acid sequence corresponds to a stapled amino acid sequence if:
(1) the amino acid sequence comprises two amino acids symbolized by an asterix (*), and each instance of the symbol (*) independently corresponds to two stapled amino acids of the Formula (iii); or
(2) the amino acid sequence comprises an amino acid symbolized by a carrot (^) and two amino acids symbolized by the asterix (*), and the symbols (*)-(^)-(*) correspond to three stapled amino acids of the Formula (iv).

In certain embodiments of Formula (I), each instance of the symbol (*) corresponds to the amino acid $A_5$. In certain embodiments of Formula (I), each instance of the symbol (*) corresponds to the amino acid $A_8$. In certain embodiments of Formula (I), each instance of the symbol (*) corresponds to the amino acid S-$A_5$. In certain embodiments of Formula (I), each instance of the symbol (*) corresponds to the amino acid S-$A_8$.

In certain embodiments of Formula (II), two instances of the symbol (*) corresponds to correspond to two stapled $A_5$ amino acids, e.g., two stapled S-$A_5$ amino acids. In certain embodiments of Formula (II), two instances of the symbol (*) corresponds to correspond to two stapled $A_8$ amino acids, e.g., two stapled S-$A_8$ amino acids.

In certain embodiments of Formula (I), the carrot symbol (^) corresponds to the amino acid $B_5$. In certain embodiments of Formula (I), the carrot symbol (^) corresponds to the amino acid $B_8$.

In certain embodiments of Formula (II), wherein the amino acid sequence comprises one staple, two instances of (*) correspond to stapled $A_5$-$A_5$ amino acids; e.g., two stapled (S-$A_5$)-(S-$A_5$) amino acids or two stapled (S-$A_8$)-(S-$A_8$) amino acids.

In certain embodiments of Formula (II), wherein the amino acid sequence comprises two staples, the symbols (*)-(^)-(*) correspond to three stapled $A_5$-$B_5$-$A_5$ amino acids, e.g., three stapled (S-$A_5$)-$B_5$-(S-$A_5$) amino acids, or three stapled (S-$A_8$)-$B_8$-(S-$A_8$) amino acids.

In certain embodiments of Formula (I) and (II), the amino acid sequence corresponds to any one of the following sequences:

(SEQ ID NO: 37)
-Q-V-R-E-L-E-$A_5$-Y-I-D-$A_5$-L-L-V-R-V-M-E-E-T-P-N-I-
L-R-I-;

(SEQ ID NO: 38)
-Q-V-R-E-L-E-D-$A_5$-I-D-N-$A_5$-L-V-R-V-M-E-E-T-P-N-I-
L-R-I-;

(SEQ ID NO: 39)
-Q-V-R-E-L-E-D-Y-I-D-$A_5$-L-L-V-$A_5$-V-M-E-E-T-P-N-I-
L-R-I-;

(SEQ ID NO: 40)
-Q-V-R-E-L-E-D-Y-I-D-N-L-L-V-$A_5$-V-M-E-$A_5$-T-P-N-I-
L-R-I-;

(SEQ ID NO: 41)
-H-I-R-E-L-E-$A_5$-Y-I-D-$A_5$-L-L-V-R-V-M-E-E-T-P-S-I-
L-R-V-;

(SEQ ID NO: 42)
-H-I-R-E-L-E-D-$A_5$-I-D-N-$A_5$-L-V-R-V-M-E-E-T-P-S-I-
L-R-V-;

(SEQ ID NO: 43)
-H-I-R-E-L-E-D-Y-I-D-$A_5$-L-L-V-$A_5$-V-M-E-R-T-P-S-I-
L-R-V-;

(SEQ ID NO: 44)
-H-I-R-E-L-E-D-Y-I-D-N-L-L-V-$A_5$-V-M-E-$A_5$-T-P-S-I-
L-R-V-;

(SEQ ID NO: 45)
-I-N-F-R-L-Q-$A_5$-Y-I-D-$A_5$-I-I-V-A-I-M-E-T-N-P-S-I-
L-E-V-;

(SEQ ID NO: 46)
-I-N-F-R-L-Q-D-$A_5$-I-D-R-$A_5$-I-V-A-I-M-E-T-N-P-S-I-
L-E-V-;

(SEQ ID NO: 47)
-I-N-F-R-L-Q-D-Y-I-D-$A_5$-I-I-V-$A_5$-I-M-E-T-N-P-S-I-
L-E-V-;

-continued (SEQ ID NO: 48)
-I-N-F-R-L-Q-D-Y-I-D-R-I-I-V-A$_5$-I-M-E-A$_5$-N-P-S-I-L-E-V-;

(SEQ ID NO: 49)
-I-N-F-R-L-R-A$_5$-Y-M-D-A$_5$-I-I-L-A-I-L-D-H-N-P-S-I-L-E-I-;

(SEQ ID NO: 50)
-I-N-F-R-L-R-Q-A$_5$-M-D-K-A$_5$-I-L-A-I-L-D-H-N-P-S-I-L-E-I-;

(SEQ ID NO: 51)
-I-N-F-R-L-R-Q-Y-M-D-A$_5$-I-I-L-A$_5$-I-L-D-H-N-P-S-I-L-E-I-;
and (SEQ ID NO: 52)
-I-N-F-R-L-R-Q-Y-M-D-K-I-I-L-A$_5$-I-L-D-A$_5$-N-P-S-I-L-E-I-;

(SEQ ID NO: 53)
-Q-V-R-E-L-E-A$_5$-Y-I-D-B$_5$-L-L-V-A$_5$-V-M-E-E-T-P-N-I-L-R-I-;

(SEQ ID NO: 54)
-Q-V-R-E-L-E-D-Y-I-D-A$_5$-L-L-V-B$_5$-V-M-E-A$_5$-T-P-N-I-L-R-I-;

(SEQ ID NO: 55)
-H-I-R-E-L-E-A$_5$-Y-I-D-B$_5$-L-L-V-A$_5$-V-M-E-E-T-P-S-I-L-R-V-;

(SEQ ID NO: 56)
-H-I-R-E-L-E-D-Y-I-D-A$_5$-L-L-V-B$_5$-V-M-E-A$_5$-T-P-S-I-L-R-V-;

(SEQ ID NO: 57)
-I-N-F-R-L-Q-A$_5$-Y-I-D-B$_5$-I-I-V-A$_5$-I-M-E-T-N-P-S-I-L-E-V-;

(SEQ ID NO: 58)
-I-N-F-R-L-Q-D-Y-I-D-A$_5$-I-I-V-B$_5$-I-M-E-A$_5$-N-P-S-I-L-E-V-;

(SEQ ID NO: 59)
-I-N-F-R-L-R-A$_5$-Y-M-D-B$_5$-I-I-L-A$_5$-I-L-D-H-N-P-S-I-L-E-I-;

(SEQ ID NO: 60)
-I-N-F-R-L-R-Q-Y-M-D-A$_5$-I-I-L-B$_5$-I-L-D-A$_5$-N-P-S-I-L-E-I-.

wherein $A_5$ is the amino acid:

or two $A_5$ amino acids are joined to form an $A_5$-$A_5$ staple. and wherein $B_5$ is the amino acid:

or two $A_5$ amino acids and one $B_5$ amino acid are joined to form an $A_5$-$B_5$-$A_5$ staple.

In certain embodiments, $A_5$ is the amino acid S-$A_5$, or two $A_5$ amino acids are joined to form an (S-$A_5$)-(S-$A_5$) staple. In certain embodiments, $A_5$ is the amino acid S-$A_5$, or two $A_5$ amino acids and one $B_5$ amino acid are joined to form an (S-$A_5$)-$B_5$-(S-$A_5$) staple.

Substitution of an amino acid for another amino acid sharing similar chemical properties is contemplated by the present invention. For example, methionine (M), alanine (A), leucine (L), glutamate (E), and lysine (K) have especially high alpha-helix forming propensities. In contrast, proline (P) and glycine (G) are alpha-helix disruptors. Arginine (R), histidine (H), and lysine (L) contain amino functionalized side chains which are basic and may be positively charged. Aspartic acid (D) and glutamic acid (E) contain carboxylic acid (—$CO_2H$) functionalized side chains which are acidic and may be negatively charged. Serine (S) and threonine (T) each contain hydroxyl (—OH) functionalized side chains. Asaparagine (N) and glutamine (G) each contain amide (—$CONH_2$) functionalized side chains. Alanine (A), valine (V), isoleucine (I), leucine (L), methionine (M), phenylalanine (F), and tryptophan (W) are classified as hydrophobic. The present invention contemplates one or more point mutations to the amino acid sequences, as recited above and herein, by substitution of one or more amino acids for one or more different amino acids. In certain embodiments, the polypeptide includes one, two, three, four, or five point mutations. In certain embodiments, the polypeptide includes one, two, three, four, five, or more additional amino acids. In certain embodiments, the polypeptide has one, two, three, four, or five amino acids removed from the sequence. In certain embodiments, the resulting amino acid sequence is 95%, 97%, 98%, or 99% homologous to the amino acid sequence as recited herein.

Two or more amino acids present in an inventive polypeptide may be further conjugated to each other, e.g., via Click chemistry. Click chemistry is a chemical philosophy introduced by Sharpless in 2001 and describes chemistry tailored to generate substances quickly and reliably by joining small units together (see, e.g., Kolb, Finn and Sharpless *Angewandte Chemie International Edition* (2001) 40: 2004-2021; Evans, *Australian Journal of Chemistry* (2007) 60: 384-395). The reactions in Click chemistry should be modular, wide in scope, give high chemical yields, generate inoffensive byproducts, be stereospecific, be physiologically stable, exhibit a large thermodynamic driving force (e.g., >84 kJ/mol to favor a reaction with a single reaction product), and/or have high atom economy. Several reactions have been identified which fit this concept:

(1) The Huisgen 1,3-dipolar cycloaddition (e.g., the Cu(I)-catalyzed stepwise variant, often referred to simply as the "click reaction"; see, e.g., Tornoe et al., *Journal of Organic Chemistry* (2002) 67: 3057-3064). Copper and ruthenium are the commonly used catalysts in the reaction. The use of copper as a catalyst results in the formation of 1,4-regioisomer whereas ruthenium results in formation of the 1,5-regioisomer;

(2) Other cycloaddition reactions, such as the Diels-Alder reaction;

(3) Nucleophilic addition to small strained rings like epoxides and aziridines;

(4) Nucleophilic addition to activated carbonyl groups; and (4) Addition reactions to carbon-carbon double or triple bonds.

In certain embodiments, the polypeptides are further modified to render the polypeptides cell permeable. Cell permeability of an inventive peptide may be increased, for example by a) introducing an additional R, Q, or W residue, and/or b) adding one or more additional R, Q, or W residues at the N- and/or C-terminus of the polypeptide.

The staple(s) of polypeptides of Formula (II) may further comprise additional synthetic modification(s). Any chemical or biological modification may be made. In certain embodiments, such modifications include reduction, oxidation, and nucleophilc or electrophilic additions to the double bond provided from a metathesis reaction of the cross-link to provide a synthetically modified stapled polypeptide. One of ordinary skill in the art will appreciate that a wide variety of conditions may be employed to promote such transformations, therefore, a wide variety of conditions are envisioned; see generally, *March's Advanced Organic Chemistry: Reactions, Mechanisms, and Structure*, M. B. Smith and J. March, 5th Edition, John Wiley & Sons, 2001; *Advanced Organic Chemistry, Part B: Reactions and Synthesis*, Carey and Sundberg, 3rd Edition, Plenum Press, New York, 1993; and *Comprehensive Organic Transformations*, R. C. Larock, 2nd Edition, John Wiley & Sons, 1999, the entirety of each of which is hereby incorporated herein by reference. Exemplary conditions may be any reagent reactive with a double bond. In certain embodiments, the reagent is able to react with a double bond, for example, via a hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized single bond. As one of ordinary skill in the art will clearly recognize, these above-described transformations will introduce functionalities compatible with the particular stabilized structures and the desired biological interactions; such functionalities include, but are not limited to, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol, halo; cyano; nitro; azido; imino; oxo; and thiooxo.

Other modifications may further include conjugation of the stapled polypeptide, or a synthetically modified stapled polypeptide, with a biologically active agent, label or diagnostic agent anywhere on the polypeptide scaffold, e.g., such as at the N-terminus of the polypeptide, the C-terminus of the polypeptide, on an amino acid side chain of the polypeptide, or at one or more modified or unmodified stapled sites. Such modification may be useful in delivery of the peptide or biologically active agent to a cell, tissue, or organ. Such modifications may allow for targeting to a particular type of cell or tissue. Conjugation of an agent (e.g., a label, a diagnostic agent, a biologically active agent) to the inventive polypeptide may be achieved in a variety of different ways. The agent may be covalently conjugated, directly or indirectly, to the polypeptide at the site of stapling, or to the N-terminus or the C-terminus of the polypetide chain. Alternatively, the agent may be noncovalently conjugated, directly or indirectly, to the polypeptide at the site of stapling, or to the N-terminus or the C-terminus of the polypetide chain. Indirect covalent conjugation is by means of one or more covalent bonds. Indirect noncovalent conjugation is by means of one or more noncovalent bonds. Conjugation may also be via a combination of non-covalent and covalent forces/bonds. The agent may also be conjugated through a covalent or noncovalent linking group. Any number of covalent bonds may be used in the conjugation of a biologically active agent and/or diagnostic agent to the inventive polypeptide present invention. Such bonds include amide linkages, ester linkages, disulfide linkages, carbon-carbon bonds, carbamate, carbonate, urea, hydrazide, and the like. In some embodiments, the bond is cleavable under physiological conditions (e.g., enzymatically cleavable, cleavable with a high or low pH, with heat, light, ultrasound, x-ray, etc.). However, in some embodiments, the bond is not cleavable.

Uses of the Inventive Stapled Polypeptides

In certain embodiments, the inventive stapled polypeptides can be used to alter one or more characteristics of the target RAB. In certain embodiments, the characteristics of the RAB is altered in such a way that this alteration affects cell fate and/or cell behavior. In certain embodiments, changes in cell fate or cell behavior as a result of changes in one or more characteristics of the target affect the disease state of a subject, such as a mammal, for example, a human. In certain embodiments, inventive stapled polypeptides can be used to treat disease. In certain embodiments, inventive stapled polypeptides can be used to probe or elucidate biological pathways in research. The probing of a biological pathway can be performed both in vitro such as in cell or tissue culture, or in vivo, such as in an animal, e.g., humans, mice, rats, hamsters, fish, or primates.

The inventive stapled polypeptides described herein, in certain embodiments, comprise amino acid sequences that bind efficiently to RAB. The inventive stapled polypeptides described herein comprise sequences that are approximately 26 amino acids long. In other embodiments, the peptides are approximately approximately 26-100, 26-150, 26-200, 26-250, 26-300, 26-350, 26-400, 26-450, or 26-500 amino acids long. In certain embodiments, these sequences comprise, when correctly folded, secondary structures, such as α-helices (Shiba T et al., *PNAS*, 2006, 103; 15416-21; FIG. 1).

In certain embodiments, the inventive stapled polypeptides comprise stapled α-helical portions that are suitable for targeting helical interaction motifs. Such peptides may be used as inhibitory peptides capable of antagonizing intracellular protein protein-interactions. For example, in certain embodiments, the inventive stapled polypeptides bind to RAB. In some embodiments, the inventive polypeptides that bind to RAB can disrupt the interaction of RAB with RAB Family Interacting Protein (FIP) by specifically binding to and blocking the interaction site in RAB that is facilitates interaction with FIP (of FIP heterodimers) (FIG. 1). In some embodiments, the disruption of the RAB/FIP interaction limits or suppresses the activation, endocytic recycling, cellular localization or expression of RAB/FIP target genes and gene products, e.g. EGFR, H-Ras, Her-2, and AKT. In some instances, RAB overexpression leads to increased cell proliferation, decreased sensitivity to apoptosis by serum starvation, chemotherapy, anoikis, and ultra violet (UV) irradiation (see, e.g., Cheng et al. *Cancer Research* 2005; 65:2516-2519). In certain embodiments, the disruption of the RAB/FIP interaction prevents increased cell proliferatrion and decreased sensitivity to apoptosis. In other embodiments, the inventive polypeptides that bind to RAB is derived from a HP amino acid sequence. In certain embodiments, the amino acid sequence -[$X_{1-26}$]- is derived from FIP1. In certain embodiments, the amino acid sequence -[$X_{1-26}$]- is derived from FIP2. In certain embodiments, the amino acid sequence -[$X_{1-26}$]- is derived from FIP3. In certain embodiments, the amino acid sequence -[$X_{1-26}$]- is derived from FIP4.

In yet other embodiments, the inventive stapled polypeptides may be derived from a peptide library screening approach. In certain embodiments, the inventive stapled polypeptides may be modified further, e.g. to substitute non-natural amino acids for natural amino acids, to add or substitute positively charged amino acids for uncharged or negatively charged amino acids, to improve upon RAB-RFP binding interactions (increase binding affinity or specificity) or to add N-terminal or C-terminal moieties, such as tags or labels.

In certain embodiments, methods of treating a condition are provided which include administering to a subject diagnosed with or having susceptibility to the condition, an effective amount of an inventive stapled polypeptide, or pharmaceutically acceptable salt thereof. Exemplary conditions which may be treated include, but are not limited to, proliferative, neurological, immunological, endocrinologic, cardiovascular, hematologic, and inflammatory diseases, disorders. In certain embodiments, cancers which may be treated by administration of an inventive RAB targeting polypeptide are listed in Table I:

In certain embodiments, the inventive stapled polypeptides are used to treat conditions associated with abberrant RAB protein levels and/or RAB activity, e.g. in cells dysfunctional in degrading RAB and/or cells in which FIP/RAB target proteins or genes are ectopically expressed. In specific embodiments, such cells are cancer cells.

Current strategies for targeting RAB signaling have mostly focused on anticancer therapies. The inventive stapled polypeptides described herein may also be used for treatment of other diseases, such as RAB-associated neurodegenerative diseases, degenerative bone diseases, and cardiovascular diseases (see website: projectreporter.nih.gov/project_info_description.cfm ?icde=0&aid=7989509). Activated RAB signaling plays a role in ovarian and breast cancer development (Cheng et al. *Cancer Research* 2005; 65:2516-2519).

Mutation of RABs or associated regulatory proteins causes numerous human genetic diseases, for example, Griscelli syndrome. Several genetic diseases are caused by partial dysfunction of multiple RAB proteins resulting from mutations in general regulators of RAB activity; RAB escort protein-1 (choroideremia), RAB geranylgeranyl transferase (Hermansky-Pudlak syndrome) and RAB GDP dissociation inhibitor-α (X-linked mental retardation). In infectious diseases caused by intracellular microorganisms, the function of endocytic RAB is altered either as part of host defences or as part of survival strategy of the pathogen (Seabra et al. *Trends in Molecular Medicine* 2002;8(1):23-30). Cancer, neurodegeneration and diabetes represent examples of acquired human diseases resulting from the up- or down-regulation or aberrant function of RABs. The broad range of physiologic processes and organ systems affected by altered RAB activity is based on pivotal roles in responding to cell signaling and metabolic demand through the coordinate regulation of membrane trafficking. The Rab-regulated processes of cargo sorting, cytoskeletal translocation of vesicles and appropriate fusion with the target membranes control cell metabolism, viability, growth and differentiation (Agola et al. *Clin Genet* 2011;June 8:Epub ahead of print).

In certain embodiments, the inventive stapled polypeptides may be used for regenerative medicine, such as for treating osteoporosis by modulating osteoblast differentiation and/or bone formation. They may also be used in the treatment of neurodegenerative diseases, or may be used in stem cell-based therapies to modulate organ regeneration, tissue regeneration, and/or injury healing.

As used herein a proliferative disease, condition, or disorder includes, but is not limited to, benign neoplasms, cancer, hematopoietic neoplastic disorders, proliferative breast disease, proliferative disorders of the lung, prolifera-

TABLE 1

RAB11FIPs are overexprsssed and implicated in the pathophysiology of a number of cancer lineages

| Tumor type | RCP | RAB11FIP2 | RAB11FIP3 | RAB11FIP4 | RAB11FIP5 | RAB11A | RAB11B | RAB25 | RAB23 |
|---|---|---|---|---|---|---|---|---|---|
| Breast | $10^{-8}$ | | | | $10^{-6}$ | $10^{-8}$ | | $10^{-38}$ | |
| Colon | $10^{-50}$ | | | $10^{-16}$ | | $10^{-17}$ | | $10^{-50}$ | |
| Lung | $10^{-11}$ | | | | | | | $10^{-24}$ | |
| Ovarian | | $10^{-11}$ | | $10^{-17}$ | | | | | |
| Renal | | $10^{-12}$ | $10^{-42}$ | | $10^{-50}$ | | | | |
| Endometrial | | $10^{-18}$ | | $10^{-20}$ | | | | $10^{-17}$ | $10^{-13}$ |
| Prostate | | | | | | $10^{-11}$ | | $10^{-10}$ | $10^{-22}$ |
| Bladder | | | | | | | | $10^{-10}$ | |
| Carcinoid | | | $10^{-13}$ | | | | | | | tive disorders of the colon, proliferative disorders of the liver, and proliferative disorders of the ovary.

Examples of cancers include carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi's sarcoma.

Examples of hematopoietic neoplastic disorders include diseases involving hyperplastic/neoplastic cells of hematopoietic origin, e.g., arising from myeloid, lymphoid or erythroid lineages, or precursor cells thereof. In certain embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of proliferative breast diseases include epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of proliferative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, non-inflammatory pleural effusions, pneumothorax, and pleural tumors, including solitary fibrous tumors (pleural fibroma) and malignant mesothelioma.

Examples of proliferative disorders of the colon include, but are not limited to, non-neoplastic polyps, adenomas, familial syndromes, colorectal carcinogenesis, colorectal carcinoma, and carcinoid tumors.

Examples of proliferative disorders of the liver include, but are not limited to, nodular hyperplasias, adenomas, and malignant tumors, including primary carcinoma of the liver and metastatic tumors.

Examples of proliferative disorders of the ovary include ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

Examples of neurological diseases and disorders include Alzheimer's disease, Parkinson's disease, amyotrophic lateral sclerosis (ALS) retinitis pigmentosa, spinal muscular atrophy, and various forms of cerebellar degeneration, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob disease, Gerstmann Straussler-Scheinker Syndrome, Bovine Spongiform Encephalitis, a Prion-mediated disease, Huntington's disease, Pick's disease, Amyotrophic Lateral Schlerosis (ALS), Parkinson's disease, and Lewy Body Disease.

Some examples of immunologic disorders include but are not limited to organ transplant rejection, arthritis, lupus, IBD, Crohn's disease, asthma, multiple sclerosis, diabetes, Graft versus host diseases, autoimmune diseases, psoriasis, rheumatoid arthritis, etc.

Examples of cardiovascular disorders include atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema, and chronic pulmonary disease.

The inventive stapled polypeptides or pharmacutical compositions thereof may serve to treat any the above-described conditions.

Pharmaceutical Compositions

The present invention provides pharmaceutical compositions comprising an inventive stapled polypeptide, or a pharmaceutically acceptable salt thereof, and, optionally, a pharmaceutically acceptable excipient. Such pharmaceutical compositions may optionally comprise one or more additional biologically or therapeutically active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to an inventive stapled polypeptide, as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds, such as chickens, ducks, geese, and/or turkeys.

The formulations of the pharmaceutical compositions described herein may be prepared by any method known or hereafter developed in the art of pharmacology. In general, such preparatory methods include the step of bringing the active ingredient into association with a excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as polyethoxylated castor oil (e.g. CREMOPHOR™), alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients, such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of this invention may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537.

Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Administration

In some embodiments, an effective amount of an inventive stapled polypeptide is delivered to a subject prior to, simultaneously with, and/or after diagnosis of the condition. In some embodiments, a therapeutic amount of an inventive stapled polypeptide is delivered to a subject prior to, simultaneously with, and/or after onset of symptoms of a condition. In some embodiments, the amount of inventive stapled polypeptide is sufficient to treat, alleviate, ameliorate, relieve, delay onset of, inhibit progression of, reduce severity of, and/or reduce incidence of one or more symptoms or features of the condition.

The inventive stapled polypeptides and compositions thereof, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions of the present invention may be administered by any route. In some embodiments, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the inventive composition may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be appreciated that inventive stapled polypeptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

Pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive polypeptide may be administered concurrently with another biologically active agent used to treat the same disorder), and/or they may achieve different effects (e.g., control of any adverse effects). In some embodiments, polypeptides of the invention are administered with a second biologically active agent that is approved by the U.S. Food and Drug Administration.

In will further be appreciated that biologically active agents utilized in this combination may be administered together in a single composition or administered separately in different compositions.

In general, it is expected that biologically active agents utilized in combination be utilized at levels that do not exceed the levels at which they are utilized individually. In some embodiments, the levels utilized in combination will be lower than those utilized individually.

In some embodiments, inventive pharmaceutical compositions may be administered in combination with any biologically active agent or therapeutic regimen that is useful to treat, alleviate, ameliorate, relieve, delay onset of, inhibit progression of, reduce severity of, and/or reduce incidence of one or more symptoms or features of cancer. For example, inventive compositions may be administered in combination with traditional cancer therapies including, but not limited to, surgery, chemotherapy, radiation therapy, hormonal therapy, immunotherapy, complementary or alternative therapy, and any combination of these therapies.

The inventive stapled polypeptides may be used for treatments of any of the diseases described herein, either as single agents or in combination with other agents, that may target additional aspects of the RAB signaling pathways. For example, RAB ligands may be targeted by antisense molecules, RNAi-based strategy, and neutralizing antibodies. RAB may be directly targeted, e.g. by antisense, RNA interference, and/or protein knockdown strategies. Combination therapies involving the inventive polypeptides described herein, may include modulation of one or more of RAB target genes.

RAB signaling pathways exhibit cross-talk to other major signaling pathways. This cross-talk can result in disease or can be implemented in disease progression. In certain embodiments, the inventive polypeptides described herein are used in combination with other agents (e.g., small-molecule compounds and/or human neutralizing antibodies) in combination therapy, for example to increase the efficacy of cancer treatment.

In some embodiments, inventive stapled polypeptides are administered in combination with one or more anti-cancer agents. An anti-cancer agent may be, for instance, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH- 4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'-deoxycoformycin), Semustine (methyl-CCNU), Teniposide (VM-26) or Vindesine sulfate, signal transduction inhibitors (such as MEK, BRAF, AKT, her2, mTOR, and PI3K inhibitors), but it is not so limited.

In some embodiments, inventive compositions are administered in combination with one or more immunotherapeutic agents. An immunotherapeutic agent may be, for instance, Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab or ImmuRAIT-CEA, but it is not so limited.

A therapeutic substance may also be any of the following agents: adrenergic agent; adrenocortical steroid; adrenocortical suppressant; agents for treating cognition, antiplatelets, aldosterone antagonist; amino acid; anabolic; analeptic; analgesic; anesthetic; anorectic; anti-acne agent; anti-adrenergic; anti-allergic; anti-Alzheimer's; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; anxiolytics, appetite suppressant; blood glucose regulator; bone resorption inhibitor; bronchodilator; cardiovascular agent; cholinergic; COX1 inhibitors, COX2 inhibitors, direct thrombin inhibitors, depressant; diagnostic aid; diuretic; dopaminergic agent; estrogen receptor agonist; fibrinolytic; fluorescent agent; free oxygen radical scavenger; gastrointestinal motility effector; glucocorticoid; GPIIb-IIIa antagonists, hair growth stimulant; hemostatic; histamine H2 receptor antagonists; hormone; human growth hormone, hypocholesterolemic; hypoglycemic; hypolipidemic; hypnotics, hypotensive; imaging agent; immunological agents such as immunizing agents, immunomodulators, immunoregulators, immunostimulants, and immunosuppressants; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; proton pump inhibitors, psychotropic; radioactive agent; scabicide; sclerosing agent; sedative; sedative-hypnotic; selective adenosine A1 antagonist; serotonin antagonist; serotonin inhibitor; serotonin receptor antagonist; statins, steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor, signal transduction inhibitors, but it is not so limited.

In certain embodiments, the inventive stapled polypeptides described herein can be combined with other therapies and agents. These therapies and agents may further be combined with yet other therapies and agents. For example, antibody-based therapies can be combined with inhibitors of signal transduction to enhance efficacy of the treatment. The cytotoxic effects of Herceptin® (Trastuzumab, Genentech), which targets HER2, may be enhanced when combined with mTOR inhibitors, EGFR/HER2 inhibitors (e.g., Lapatinib, Tykerb®, GlaxoSmithKline plc). The chemotherapeutic drug fludarabine (Fludara®), may be combined with PI3K and/or mTOR inhibitors to enhance apoptosis of cancer cells, such as leukemia cells. Rapamycin may be combined with paclitaxel (Taxol®, Bristol-Myers Squibb), carboplatin, and/or vinorelbine (Navelbine®) to exert stronger effects on cancers such as cervical cancer and breast cancer. Rapamycin may be combined with the cell cycle check point kinase (ChK1) inhibitor UCN-01 (7-hydroxystaurosporine) in cancer cells that exhibit aberrantly regulated Raf/MEK/ERK, Akt, and/or JNK signal transduction pathways. Farnesyltransferase inhibitors, such as L744832 and R115777 (Zarnestra®) may also be combined with UCN-01 or with agents such as paclitaxel, docetaxel, doxorubicin, 5-flurouracil, cisplatin, melphalan, mitoxantrone, and/or dexamethasone. PI3K inhibitors, such as PWT-458 (pegylated 17-hydroxywortmannin) can be used to modulate glioma, non-small cell lung cancer (NSCLC) and renal cell carcinoma growth and may be combined with paclitaxel and/or rapamycin (pegylated rapamycin). The PI3K inhibitor LY294002 may be combined with doxorubicin to enhance induction of apoptosis. Perifosine® (KRX-0401, Keryx Biopharmaceuticals) an alkylphospholipid that inhibits Akt, may be combined with dexamethasome, doxorubicin, melphalan (Alkeran®), and/or bortezomib (Valcade®, Millennium Pharmaceuticals) to enhance toxicity, e.g. in multiple myeloma. Akt inhibitors (e.g. A-443654, Abbott) and MEK inhibitors (e.g., CI-1040, PD 184352) may be combined with rapamycin and/or paclitaxel to enhance suppression of tumor growth. MEK inhibitors may enhance apoptosis of cancer cells when combined with arsenic trioxide, and may be combined with UCN-01. Suntinib (Sutent®, Pfizer), which inhibits VEGFR, may be used to chemo-sensitize cancer cells when combined with, e.g., cisplatin. Antibodies, such as Bevacizumab (Avastin®, Genentech/Roche), may be combined with kinase inhibitors, such as Suntinib, Sorafenib (Nexavar®, Bayer), Erlotinib (Tarceva®, an EGFR inhibitor) and also with mTOR inhibitors. Many other such combinations of agents and/or therapies are known in the art.

In some embodiments, inventive stapled polypeptides are administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g., chemotherapy, radiation therapy, hormonal therapy, immunotherapy, complementary or alternative therapy) may be employed.

In some embodiments, inventive stapled polypeptides are administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g., a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some embodiments, inventive stapled polypeptides are administered in combination with immunotherapy. Immunotherapy is the use of immune mechanisms against tumors which can be used in various forms of cancer, such as breast cancer (e.g., trastuzumab/Herceptin®), leukemia (e.g., gemtuzumab ozogamicin/Mylotarg®), and non-Hodgkin's lymphoma (e.g., rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

In some embodiments, vaccines can be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes. To give but one example of a cancer vaccine, an experimental vaccine for HPV types 16 and 18 was shown to be 100% successful at preventing infection with these types of HPV and, thus, are able to prevent the majority of cervical cancer cases (Harper et al., 2004, *Lancet,* 364:1757).

In some embodiments, inventive stapled polypeptides are administered in combination with complementary and alternative medicine treatments. Some exemplary complementary measures include, but are not limited to, botanical medicine (e.g., use of mistletoe extract combined with traditional chemotherapy for the treatment of solid tumors); acupuncture for managing chemotherapy-associated nausea and vomiting and in controlling pain associated with surgery; prayer; psychological approaches (e.g., "imaging" or meditation) to aid in pain relief or improve mood. Some exemplary alternative measures include, but are not limited to, diet and other lifestyle changes (e.g., plant-based diet, the grape diet, and the cabbage diet).

In some embodiments, inventive stapled polypeptides are administered in combination with any of the traditional cancer treatments described herein, which are often associated with unpleasant, uncomfortable, and/or dangerous side effects. For example, chronic pain often results from continued tissue damage due to the cancer itself or due to the treatment (i.e., surgery, radiation, chemotherapy). Alternatively or additionally, such therapies are often associated with hair loss, nausea, vomiting, diarrhea, constipation, anemia, malnutrition, depression of immune system, infection, sepsis, hemorrhage, secondary neoplasms, cardiotoxicity, hepatotoxicity, nephrotoxicity, ototoxicity, etc. Thus, inventive compositions which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g., morphine, oxycodone, antiemetics, etc.); nausea and vomiting can be treated with 5-$HT_3$ inhibitors (e.g., dolasetron/Anzemet®, granisetron/Kytril®, ondansetron/Zofran®, palonsetron/Aloxi®) and/or substance P inhibitors (e.g., aprepitant/Emend®); immunosuppression can be treated with a blood transfusion; infection and/or sepsis can be treated with antibiotics (e.g., penicillins, tetracyclines, cephalosporins, sulfonamides, aminoglycosides, etc.); and so forth.

In some embodiments, inventive compositions may be administered and/or inventive diagnostic methods may be performed in combination with any therapeutic agent or therapeutic regimen that is useful to diagnose one or more symptoms or features of cancer (e.g., detect the presence of and/or locate a tumor). In some embodiments, inventive conjugates may be used in combination with one or more other diagnostic agents. To give but one example, conjugates used to detect tumors may be administered in combination with other agents useful in the detection of tumors. For example, inventive conjugates may be administered in combination with traditional tissue biopsy followed by immunohistochemical staining and serological tests (e.g., prostate serum antigen test). Alternatively or additionally, inventive conjugates may be administered in combination with a contrasting agent for use in computed tomography (CT) scans and/or MRI.

EXAMPLES

The following examples are for illustrative purposes only and are not to be construed as limiting the invention in any manner.

Example 1

Stapled RAB Family Interacting Protein (FIP) Peptide Design

Permissive sites for stabilization by insertion of non-natural "$S_5$" alpha-methyl, alpha-pentenyl amino acids, or potentially other stabilizing amino acids for hydrocarbon stapling or "click" Huisgen triazole stapling were identified. FIG. 2A depicts the $S_5$ sites in FIP1-FIP4 (highlighted in grey). The sites were identified based on structural information from various FIP3-RAB11 crystal structures [Shiba T et al., *PNAS*, 2006, 103; 15416-21]. Staple spans are shown as brackets above the sequences. Contacts are denoted by specific symbols (*, ^, ~, #) according to their role in RAB11 binding, FIP3 dimerization, or potential secondary structure stabilization. Considerable sequence or structural homology is conserved between FIP isoforms, although class-II (FIP3/4) FIPs have been shown in the literature to preferentially target RAB11/RAB25. Four suitable staple positions were identified and the corresponding residues in FIP3 are labeled dark grey (FIG. 2B) in the FIP3-RAB11 crystal structure. The "XXX" nomenclature (IIV, IME, IDR, YID) represents the amino acid residues encompassed by the staple in FIP3. These were used generically to look at different staple positions in stapled peptides derived from multiple FIP isoforms.

All peptides were synthesized on an automated, multi-channel Tetras peptide synthesizer (Thuramed) using standard Fmoc-peptide chemistry methods on MBHA rink amide resin in N-methylpyrrolidinone (NMP) or N,N-dimethylformamide (DMF). Fmoc deprotection of the N-terminal amine was typically carried out in 20% piperidine in NMP for 25 minutes while bubbling nitrogen. Following deprotection, the resin was washed with NMP 3×1 minute and rinsed with DCM 1×1 minute. Amide bond formation between the N-terminal amine and the incoming amino acid was performed by adding 10 equivalents of the amino acid dissolved in NMP, followed by addition of 9.9 equivalents of HCTU and 20 equivalents of DIPEA in NMP. Coupling reactions were allowed to proceed for 30-40 minutes or longer if synthesizing a difficult stretch of residues (as was determined empirically). Coupling of non-natural amino acids ($S_5$, $R_8$, $B_5$ or other stapling residues) was performed with 3 equivalents of the amino acid, 2.95 equivalents of HCTU and 10 equivalents of DIPEA in NMP over the course of two or three hours. Chemical cross-linking of non-natural amino acids containing pentenyl side-chains was generally performed using 0.2 equivalents of Grubbs-I catalyst (benzylidene-bis(tricyclohexylphosphine)dichlororuthenium) dissolved in dichloroethane under argon for 2.5 hr, repeated twice. After olefin-metathesis, resin was washed in a 1:4 mixture of DMSO and DCM to removed excess catalyst and other adsorbed reagents from the resin. Peptides were capped with a variety of functionalities at the N-terminus including acetic anhydride (acetylation), fluorescein isothiocyanate (FITC), rhodamine isothiocyanate (Rhodamine), ethylene glycol spacers (denoted $PEG_1$, $PEG_2$ etc.), N-biotinyl-NH-$PEG_2$—COOH or biotin alone (biotinylation).

Upon completion, peptides were simultaneously cleaved from the resin and side-chains were deprotected using a trifluoroacetic acid (TFA) cleavage cocktail. In general, this cleavage mixture contained 2% deionized water, 2% triisopropylsilane (TIS), 1% 1,2-dithioethane (DTE) and 95% TFA. When methionine or other sulfide containing amino acids were present, thioanisol was included (~1%). When specific electrophilic functionalities were present (for example, potential Michael acceptors) DTE was not included. Finally, peptides containing functional groups that were expected to be labile under aqueous acidic conditions were cleaved in 5% TIS in 95% TFA (for example, internal esters or lactones). Peptides were cleaved at room temperature with gentle agitation (rotating) for 3 hours. An excess of cold diethyl ether was added to the acidic resin/peptide slurry to precipitate the peptide, which was centrifuged, the supernatant discarded and the pellet then washed, resuspended and centrifuged twice more in cold ether. In the case that a peptide did not readily precipitate, for example with small or highly polar peptides, water extraction from the ether layer was performed. The resulting crude peptide precipitate (or aqueous layer) was dried, dissolved in 1:1 acetonitrile:water, passed through a 0.2 µm syringe filter and were generally purified with a 10-90% linear acetonitrile gradient in water containing 0.1% trifluoroacetic acid (TFA) over 30 minutes by reverse-phase high-pressure liquid chromatography (HPLC) using a C18 column (Agilent, Palo Alto, Calif.). Compound identification and purity was assessed using coupled liquid chromatography mass spectrometry (LCMS) (Agilent, Palo Alto, Calif.). For most stapled peptides, the parent ion was not visible and instead the M+2/2 and M+3/3 ions were observed. Purified fractions were pooled and evaporated to dryness by high temperature vacuum (HiVac) at 40 degrees Celsius. The resulting solids or oils were taken up in Millipore purified water (with minimal acetonitrile if needed for solubility), lyophilized to dryness and stored as dry stocks at 4° C. For use in biochemical, cell-based or in vivo assays, peptides were quantified by absorbance at 280 nm when suitable aromatic moieties were present (Tryptophan, indole; Tyrosine, phenol); 307 nm for the Fmoc fluorenyl group; 494 nm when conjugated to fluorescein isothiocyanate, by amino acid analysis (AAA, Dana Farber Chemistry core facility) or by weight when produced in suitable amounts. Following quantification, peptides were dissolved in dimethylsulfoxide (DMSO, generally at 5 or 10 mM) and stored at −20° C.

Example 2

Fluorescence Polarization to Detect Unmodified FIP Peptide Binding to RAB

Figure 3:
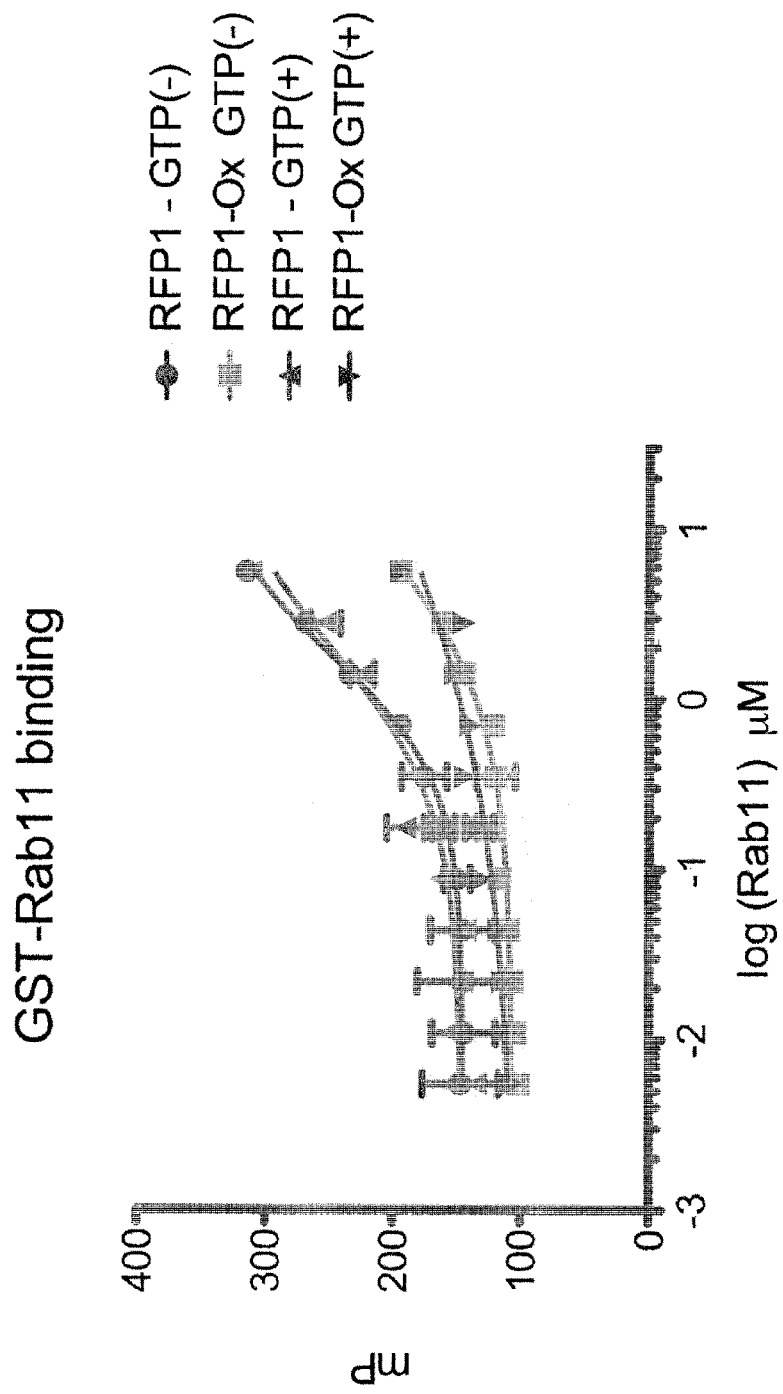
FIG. 3 is a graph demonstrating dose-dependent binding of an FITC-conjugated unmodified FIP3 peptide (FITC-RFP1) to RAB11 in the presence and absence of GTP. The graph also demonstrates dose-dependent binding of a chemical derivative of FITC-RFP1 to RAB11 in the presence and absence of GTP. A critical hydrophobic methionine residue is oxidized in the chemical derivative peptide (FITC-RFP1-Ox).

Fluorescence polarization (FP) was used to measure FIP peptide binding to RAB11 and RAB25 proteins. An unmodified FIP3 peptide conjugated to FITC (FITC-RFP1) showed dose-dependent binding to RAB11 in the presence and absence of GTP. A chemical derivative of FITC-RFP1 containing an oxidized methionine (FITC-RFP1-Ox) (in place of methionine) at a critical hydrophobic interaction site with RAB11 shows decreased binding (FIG. 3). This indicated specificity in the binding measurement, as this subtle change would be expected to perturb binding. Results from this assay indicated that fluorescent polarization should be suitable to measure binding affinities of unmodified and stapled peptides.

RAB11/25 protein binding assays were performed by incubating FITC-FIP or FITC-RFP (stapled FIP derivatives) peptides (15 nM) with three-fold dilutions of recombinantly-expressed, purified RAB11, RAB25 or a various epitope-tagged version of either in protein-binding buffer (25 mM Tris-HCl, pH 8.0, 150 mM NaCl, 1 mM EDTA, 1 mM DTT, 10 mM $MgCl_2$, 10 mM GTP). Dilutions and incubations were made in 384-well, black flat-bottom plates (Corning) to a total volume of 40 µL and equilibrated for 60 minutes. Polarization was measured on a Spectramax-M5 multi-label plate reader with $\lambda_{ex}$=485 nm and $\lambda_{em}$=525 nm. Polarization was calculated according to the standard equation: P=(V−H)/(V+H), where P=polarization, V=vertical emission intensity and H=horizontal emission intensity. $K_d$ values were determined by fitting data to a variable-slope sigmoidal binding curve using Prizm 4 graphing software.

RAB11 and RAB25 proteins were expressed and purified in *Escherichia coli* strain BL21(DE3) pLysS (Stratagene) as epitope-tagged fusion proteins in various vectors (Novagen). RAB25 (residues E7-Q180) was expressed with an N-terminal GST- and hexahistidine tag with internal thrombin and TEV cleavage sites (GST-H$_6$-RAB25) (SEQ ID NO: 86) in a pET41-1 vector (Novagen) or with an N-terminal hexahistidine tag alone with an internal thrombin cleavage site (H$_6$-RAB25) (SEQ ID NO: 86) in a pET28 vector (Novagen). FIP3 protein (residues 649-756) was expressed with an N-terminal GST-tag with an internal TEV cleavage site (GST-FIP3) in a pGEX6p-1 vector (Novagen). RAB11 (residues 1-175) was expressed with an N-terminal GST-tag with an internal thrombin cleavage site in a pGEX5x-1 vector (Novagen). Transformed bacteria was grown at 37° C. until an OD600=0.8 was reached, at which point the culture was induced with 0.5 mM isopropyl β-D-1-thiogalactopyranoside (IPTG). Induced cells were grown at 30° C. for 6 hours, pelleted and lysed in binding buffer (25 mM Tris-HC;, pH 8.0, 150 mM NaCl, 1 mM EDTA, 1 mM DTT, 10 mM MgCl$_2$, 10 mM GTP) supplemented with a complete protease inhibitor tablet (Roche) by sonication on ice. The lysate was centrifuged at 14,000 rpm to clear insoluble matter prior to loading onto Ni-NTA resin (Qiagen) for hexahistdine-tagged constructs or on GST-bind agarose resin (Biorad) for GST-tagged constructs. The protein-bound bead slurry was washed 4× with ~20 mL of buffer and retained protein was eluted with either 250 mM imidazole or 20 mM glutathione in buffer for H$_6$-(SEQ ID NO: 86) or GST-proteins, respectively. The eluent was concentrated using a 30 kD exclusion filter and purified by size-exclusion chromatography on a Superdex-75 Column (Amersham Pharmacia Biotech). Fractions containing purified protein were pooled, concentrated and dialyzed into binding buffer or other similar buffer for specific biochemical assays.

Example 3

Fluorescent Polarization to Detect Stapled FIP Peptide (RFP) Binding to RAB11 or RAB 25; Design #1

Figure 5:
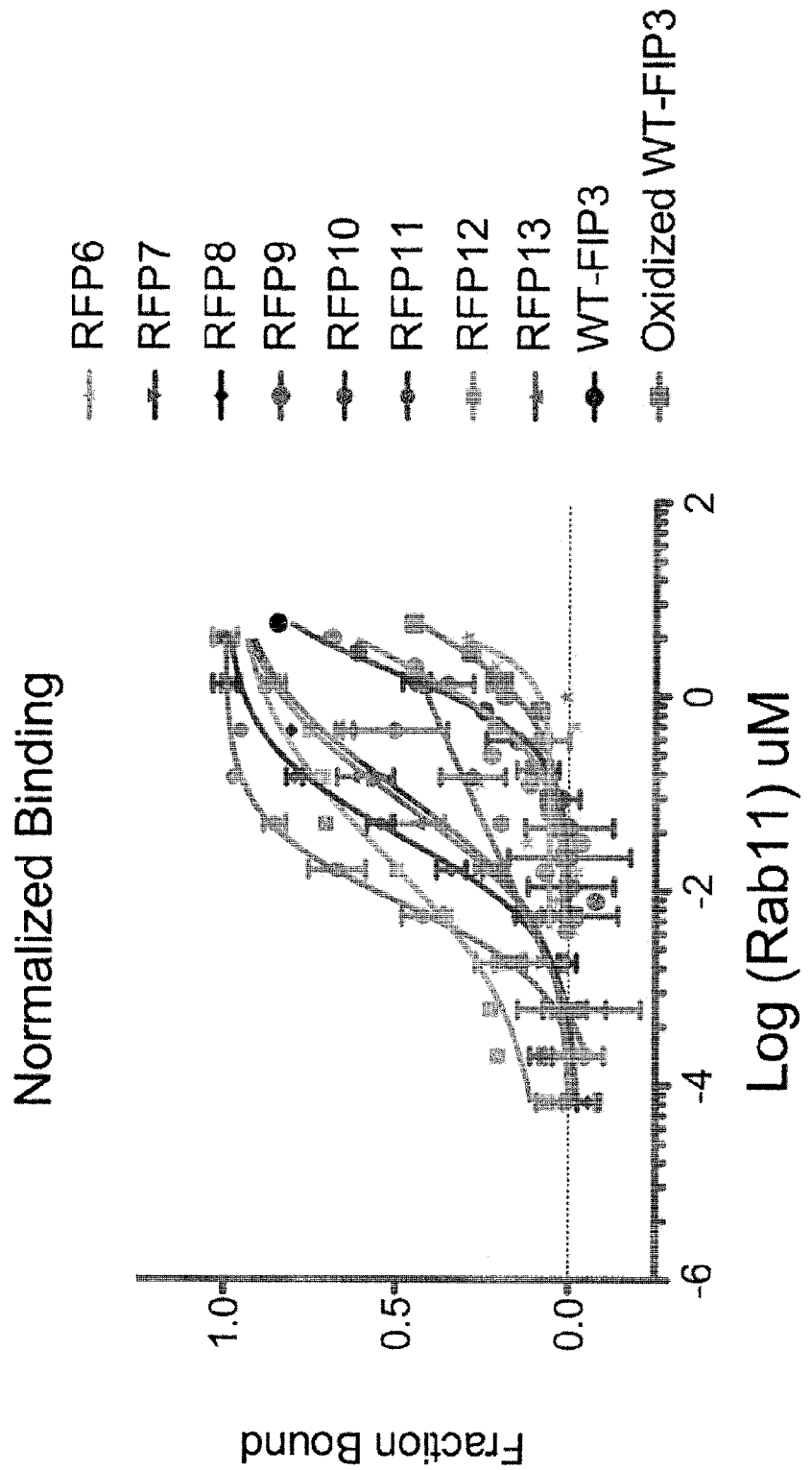
FIG. 5 is a graph demonstrating relative affinities of stapled FIP peptides (RFPs), RFP6-RFP13, wild-type (WT) FIP3, and oxidized WT FIP3 for RAB11.
Figure 6:
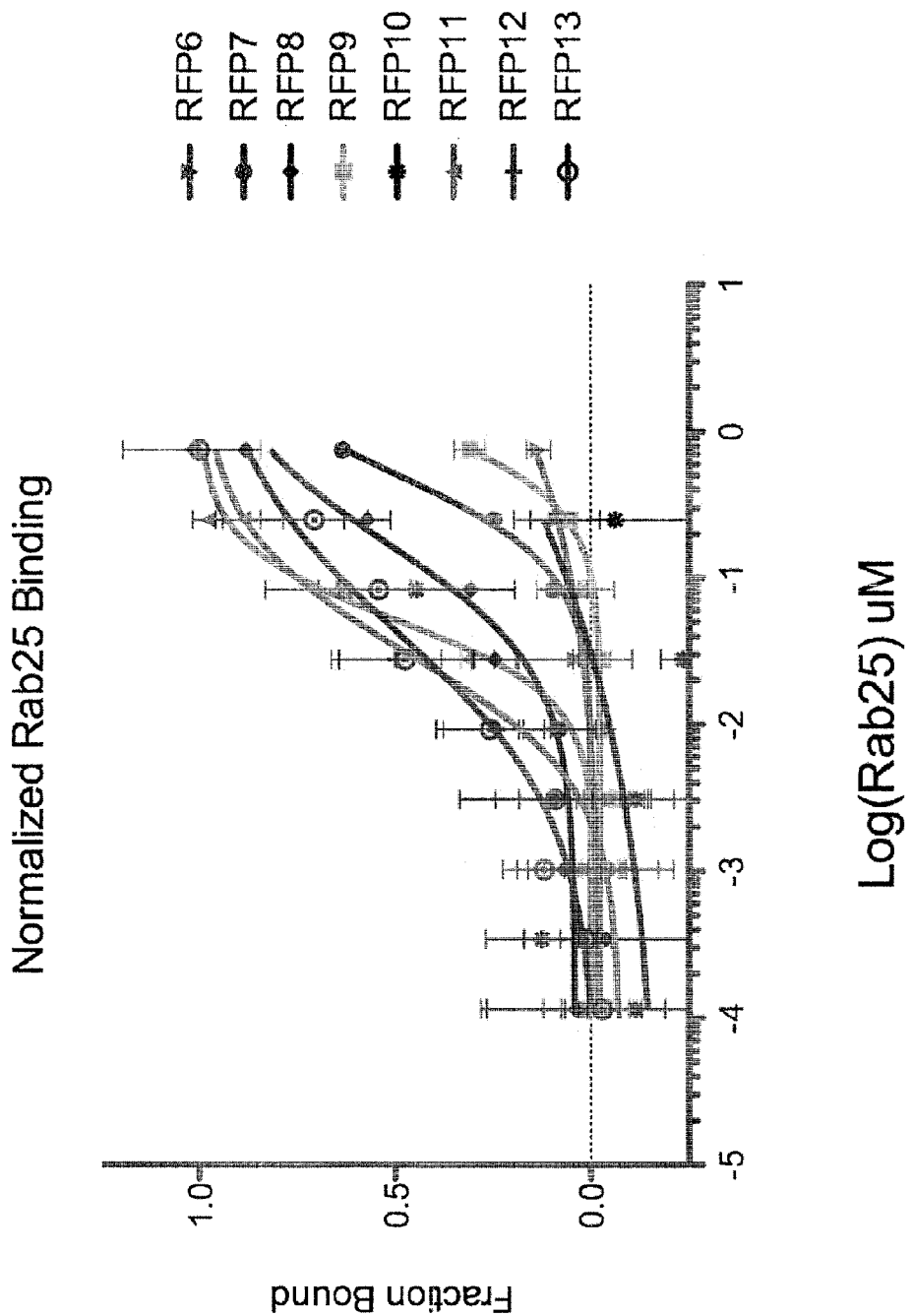
FIG. 6 is a graph demonstrating relative affinities of RFP6-RFP13 for RAB25.
Figure 8:
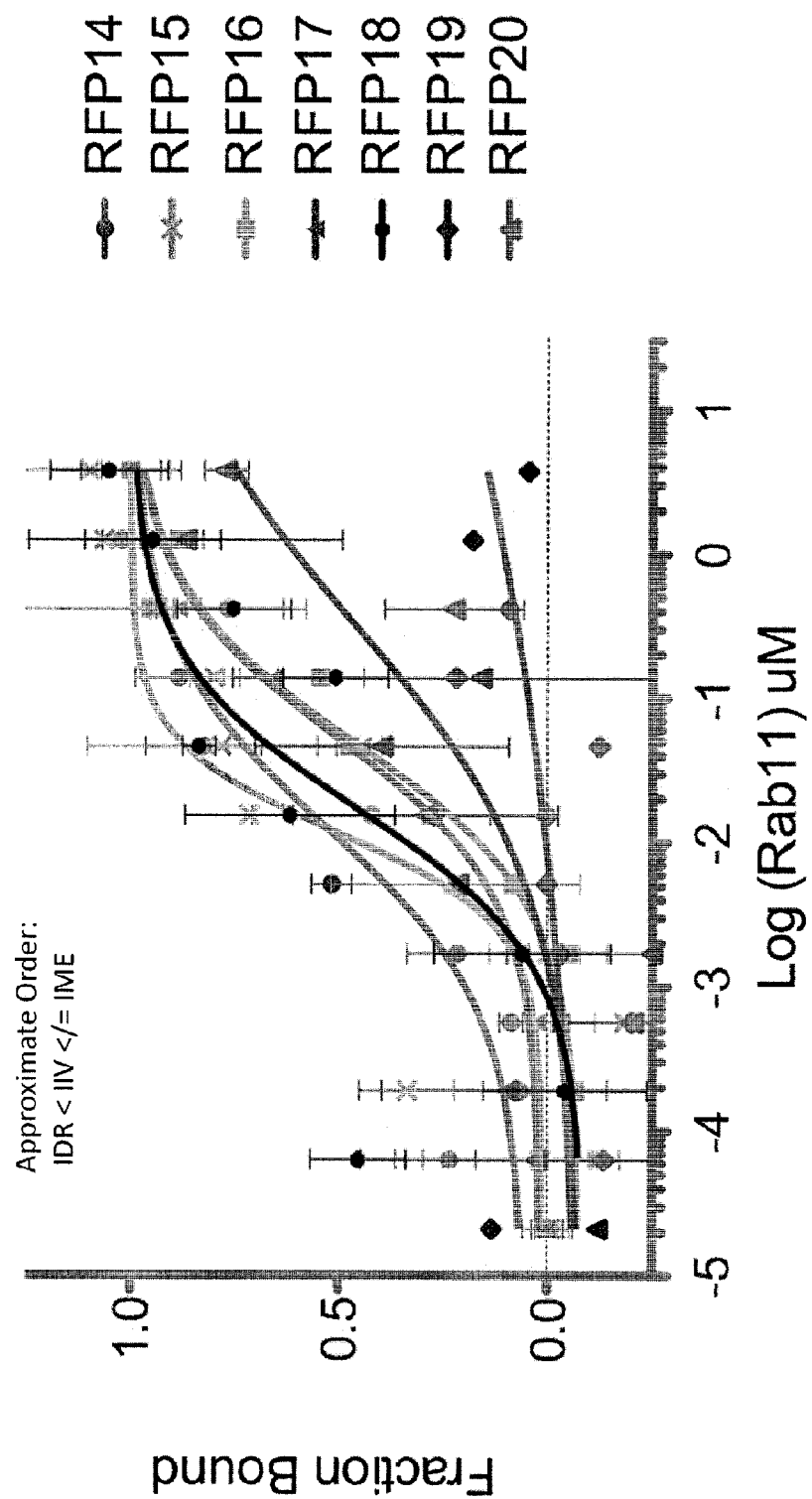
FIG. 8 is a graph demonstrating relative affinities of RFP14-RFP20 for RAB11.

FIG. 4A depicts a FITC-RFP containing an N-terminal beta-alanine spacer, a monoethylene glycol spacer, and a fluorescein isothiocyanate (FITC) cap. A panel of RFPs (RFP6-RFP13) with four staple positions representing class I (FIP1) and class II (FIP3) FIP proteins (FIG. 4B) were synthesized and tested for binding to RAB11 or RAB25. All peptides were purified by high performance liquid chromatography (HPLC) and verified by liquid chromatography-mass spectrometry (LC-MS). Dose-dependent binding was observed for many of these peptides with discrete structure-activity relationships observed for the different staple positions. Affinities ranging from low-nanomolar to micromolar were observed with some peptides showing a 100-fold decrease in $K_d$ compared to its unmodified counterpart. While the relative affinities of the RFPs are the same for RAB11 and RAB25, all of the peptides appear to bind with lower affinity to RAB25 than to RAB11 (FIG. 4B, left panel; FIGS. 4 and 5). This is consistent with unmodified peptides (for example FIP3 and FIP4) showing tighter binding to RAB11 than RAB25 (Example 7, below).

Overall, the IIV, IME, and IDR staple positions showed productive binding for both RAB11 and RAB25; however, the IDR staple position, which blocks the FIP-FIP interface, showed moderately weaker binding. Also, while stapled peptides had a higher affinity for Rab11 than Rab25, it appeared that FIP3-based peptides bound with higher affinity than FIP1-based peptides.

Example 4

Fluorescent Polarization to Detect RFP Binding to RAB11 or RAB25; Design #2

A second set of RFPs were designed based on RFP8, RFP11, and RFP13 and were tested for binding to RAB11 or RAB25 (FIG. 7). We hypothesized that the IIV and IME staple positions should not prevent FIP dimerization; however, the IDR staple position was expected to completely abolish FIP homodimer and heterotetramer formation. The YID staple position from Example 3 appeared to adversely affect RAB binding. In this set of experiments, chemically labile residues (critical Met changed to norleucine isostere) were removed, the negative charge of the peptide was reduced, the overall hydrophobicity was reduced, and critical amino acid contacts (Met to Phe) were potentially optimized. RFP19 and 20 were used as negative control peptides, with a buried aspartic acid swapped with a non-binding arginine alone and in combination with an M-to-A mutation.

The modifications to the RFPs did not appear to have had a significant effect on binding affinity to RAB11 or RAB25. Binding of negative peptide controls, RFP19 and RFP20, suggested that the other RFPs bound RAB11 and RAB25 with specificity. Overall, similar results were observed for both RAB11 and RAB25, although affinities appeared to be higher for RAB11 than for RAB25. This design strategy aimed at improving stability (M-to-NL/F) did not disrupt binding, but did improved chemical stability. Increasing the peptide charge from −2/−1 to +1/+2 empirically improves solubility and retains binding affinity. We expected the modifications described in this Example to improve cellular uptake based on our empirical observations of stapled peptides.

Figure 9:
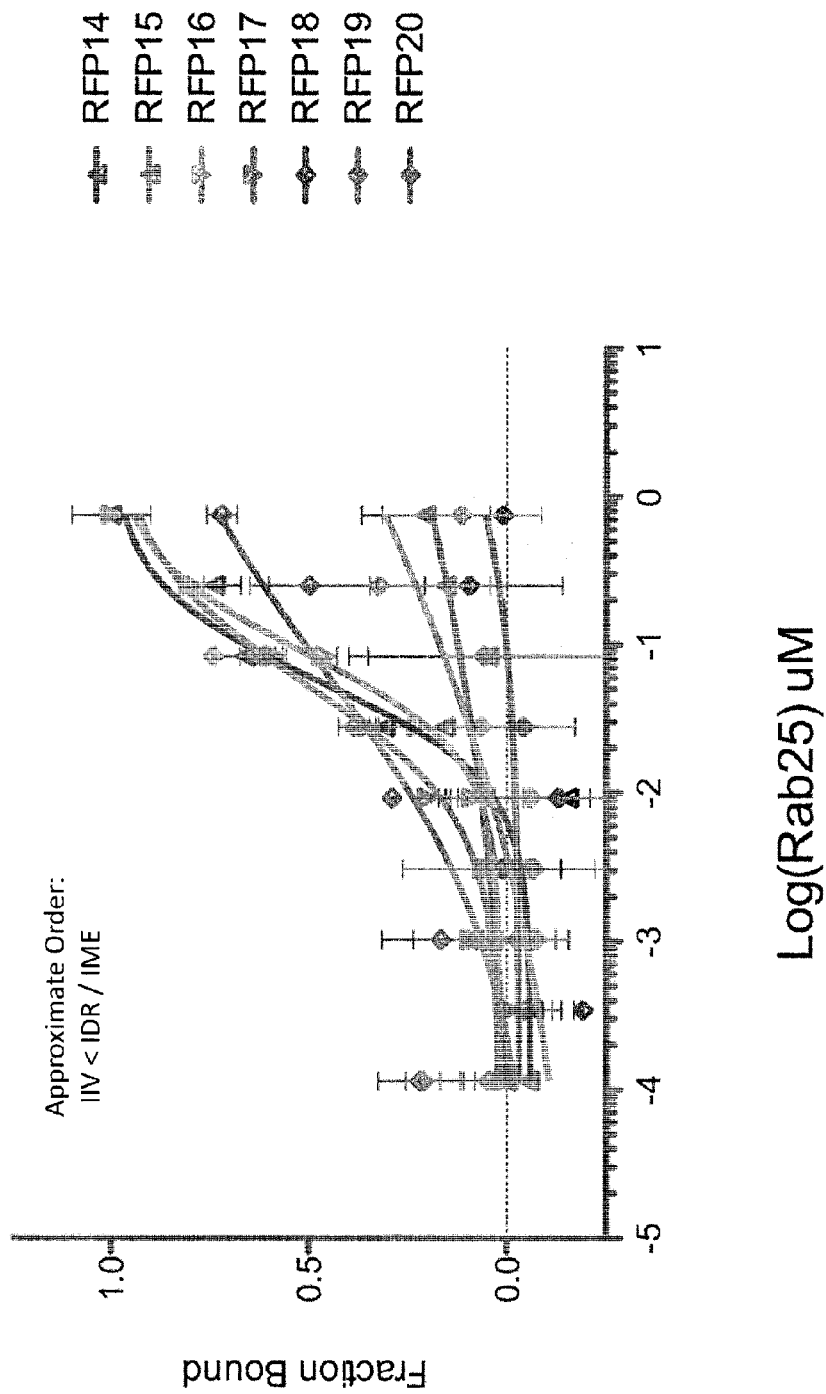
FIG. 9 is a graph demonstrating relative affinities of RFP14-RFP20 for RAB25.
Figure 10:
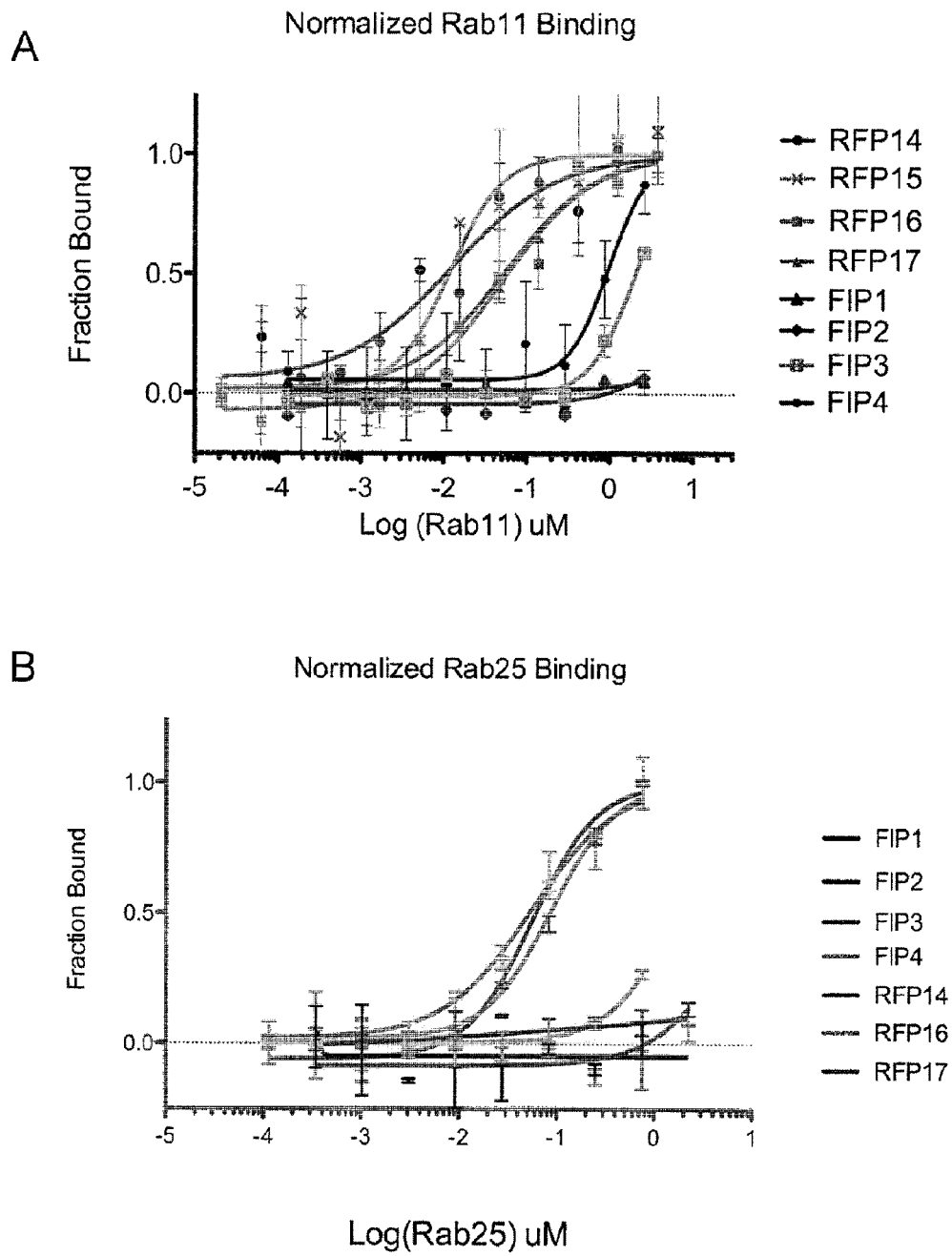
FIG. 10A is a graph demonstrating relative affinities of RFP14-17 and FIP1-4 for RAB11.
FIG. 10B is a graph demonstrating relative affinities of RFP14, RFP16, RFP17, and FIP1-FIP4 for RAB25.

We also found that FIP3/4 have micromolar binding affinities to both Rab11 and Rab25, compared to little or no binding FIP1/2 (FIGS. 9A and 9B). Notable differences between these classes are: (1) F vs. R at position at position 7, (2) E vs. Q/R at position 10, (3) R vs. E at position 29, and (4) P vs. K at position 31.

Collectively, the data from Examples 3 and 4 indicate that the candidate stapled FIP peptides expected to be most effective in serving as a dominant negatives are RFP14, RFP16, and RFP17 of the "IME" and "IDR" staple positions. RFP14 and RFP16 are slightly biased for RAB11 (2-4 fold), and RFP17 has an equivalent affinity for both RAB11 and RAB25. A near 100-fold affinity enhancement over unmodified HP peptides was observed.

Example 5

Circular Dichroism Profiles Indicate Structural Stabilization of RFP α-Helix

Figure 11:
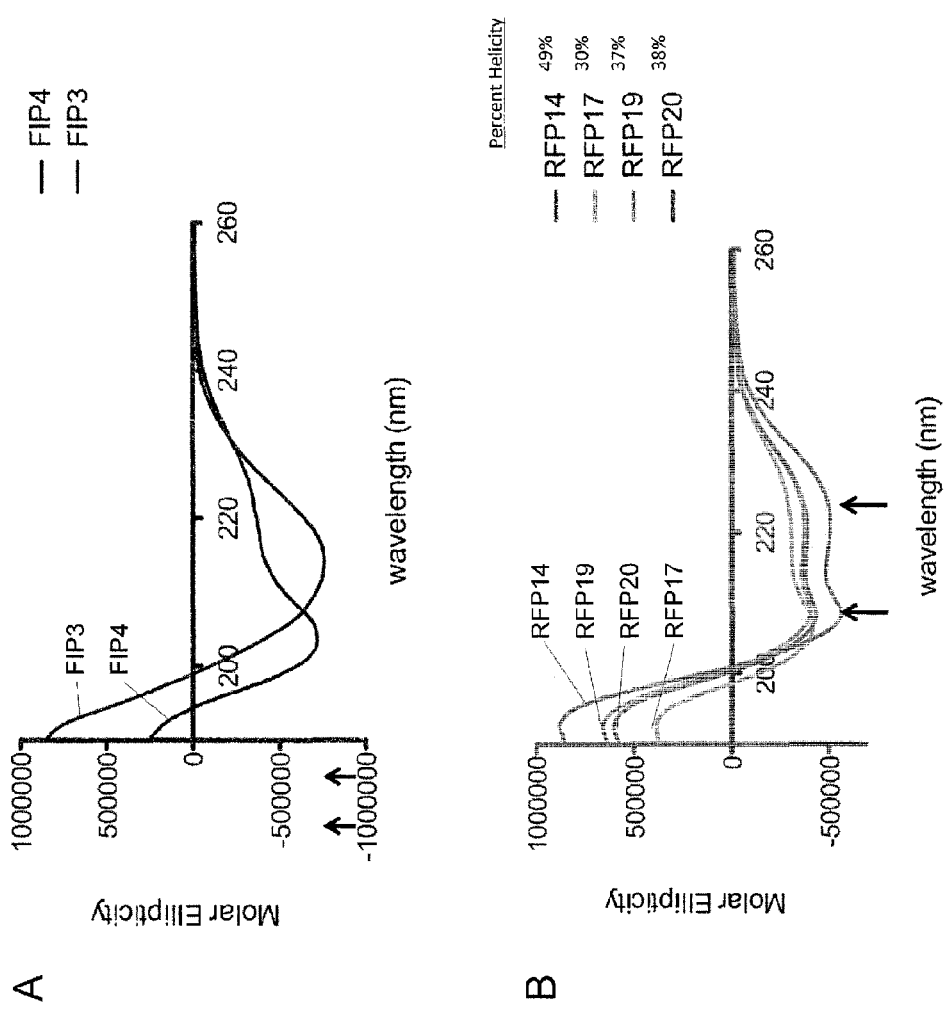
FIG. 11A depicts circular dichroism (CD) spectra for FIP3 and FIP4.
FIG. 11B shows CD spectra for RFP14, RFP17, RFP19, and RFP20.

We next investigated the structural stability of the RFPs by obtaining circular dichroism (CD) spectra for each peptide. All measurements were made at 20° C. in water with peptides at 50 μM. We found that peptide stapling induced increased helical content (stabilized a helical structure) in RFPs compared to wild-type unmodified peptides. The CD curve shapes in FIG. 11A indicate a beta-sheet structure for the FIP3 peptide (minima near 215 nm) and a partially unfolded/helical structure for FIP4 (minima near 200 nm). By comparison, stapled FIP peptides (RFPs) show helical CD spectra indicated by minima at approximately 208 and 222 nm (FIG. 11B). Theoretical percent helicity calculations ranged from 30%-50% for these peptides, with RFP14 having the highest helical content, as calculated by the absorbance at 222 nm. RFP14 also had the highest binding affinity to both RAB11 and RAB25.

A circular dichroism spectrometer (Jasco J-710, Japan) was used to determine the α-helical content of all peptides. Peptides were dissolved in water to a final concentration of 50 μM in a quartz cuvette with a path length of 1 cm. Absorbance values were taken at 1 nm intervals between 190 and 260 nm for buffer alone and for peptide solutions. The background (buffer) spectrum was subtracted from experimental spectra, which were subsequently subjected to baseline-normalization and curve-smoothing within the spectrometer software. Percent-helicity was calculated from the absorbance at 222 nm using helical models as previously reported in Chen Y H et al., *Biochemistry*, 13, 3350-9 (1974).

Example 6

Peptide Thermal Stability

Figure 12:
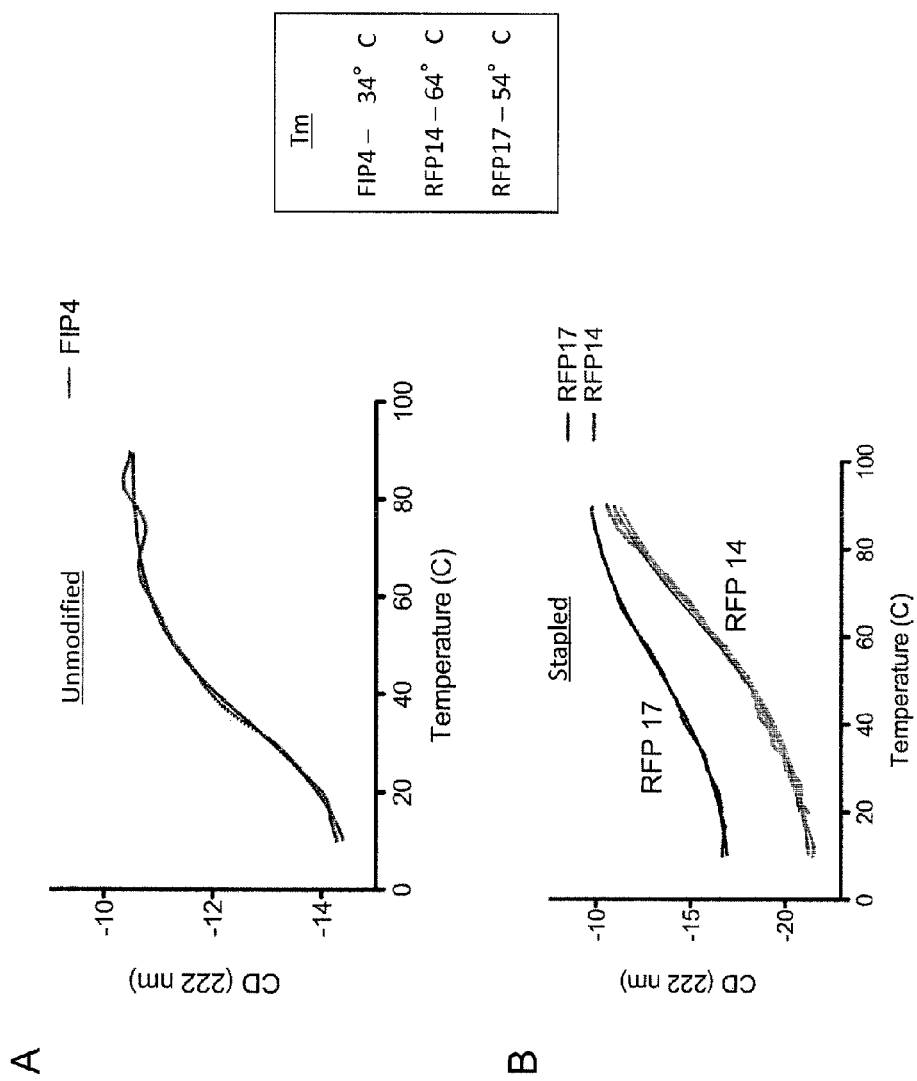
FIG. 12A is a graph of the thermal stability profile of FIP4.
FIG. 12B is a graph of the thermal stability profile of RFP14 and RFP17.

Peptide thermal stability was measured by scanning the peptide CD at 222 nm over a temperature range (10-90° C.). A sigmoidal unfolding curve was apparent for helices of unmodified FIP peptides (FIP4) with a $T_m$ of ~34° C. (FIG. 12A). Peptide stapling significantly stabilized the helical structure and thermal stability of RFPs, increasing the $T_m$ to 54° C. and 64° C. for RFP17 and RFP14, respectively (FIG. 12B).

Peptide thermal stability experiments were performed in a similar manner to circular dichroism experiments in Example 5. Peptide solutions were cooled to 10° C. in a temperature controlled CD-chamber and circular dichroism absorbance at 222 nm was measured at 1 degree intervals while the solution was heated to 90° C. 222 nm CD values were plotted as a function of temperature and fitted to a sigmoidal denaturation curve, with the half-maximal temperature representing the $T_m$.

Example 7

Protein Binding/Competition Assay

A nano-bead based time resolution fluorescence resonance energy transfer (TR-FRET) assay (AL-PHASCREEN®) was used to qualitatively assess protein binding (peptide-RAB or protein-RAB association) and quantitatively assess inhibitor ranking (competition assays). FIG. 13A shows an RFP conjugated to biotin. FIG. 13B schematizes the ALPHASCREEN® (binding) strategy. If an RFP (or FIP protein/peptide) conjugated to biotin (bound to a donor bead, in this case streptavidin) interacts with RAB conjugated to GST (bound to an acceptor bead, in this case, anti-GST), there is a proximity-dependent transfer of chemical energy, resulting in light production.

To determine reasonable protein concentrations for this assay, protein-ligand complexes consisting of biotin and GST alone (control) (FIG. 14A), biotin-FIP2 peptide and GST-RAB11 (FIG. 14B), and biotin-RFP14 and GST-$H_6$-RAB25 (SEQ ID NO: 86) (FIG. 14C) were incubated at various concentrations of biotin-labeled protein.

The biotin-RFP14/GST-$H_6$-RAB25 (SEQ ID NO: 86) experiments use streptavidin donor beads and Ni-NTA acceptor beads. The Ni-NTA acceptor beads have a higher binding capacity so they were used for the RAB25 construct. RAB11 only has the GST eptitope, so streptavidin beads were used. Results demonstrated that binding partner titration (FIP2 or RFP14) exhibited a characteristic "hook effect" with maximum signal at approximately 10 nM of GST-RAB11 and 40 nM biotinylated FIP peptide, which are reasonable concentrations for this assay (FIG. 14B). The signal to noise (S/N) ratio was suitable for screening applications (>30) with optimal concentrations. These results also support the use of wild-type peptides or stapled HP peptides as ligands for complex formation.

For competition assays, complexes consisting of biotin-FIP and GST-RAB proteins or biotin-RFP and GST-RAB peptides with free RFPs, unmodified peptides, and FIP proteins were incubated.

Figure 13:
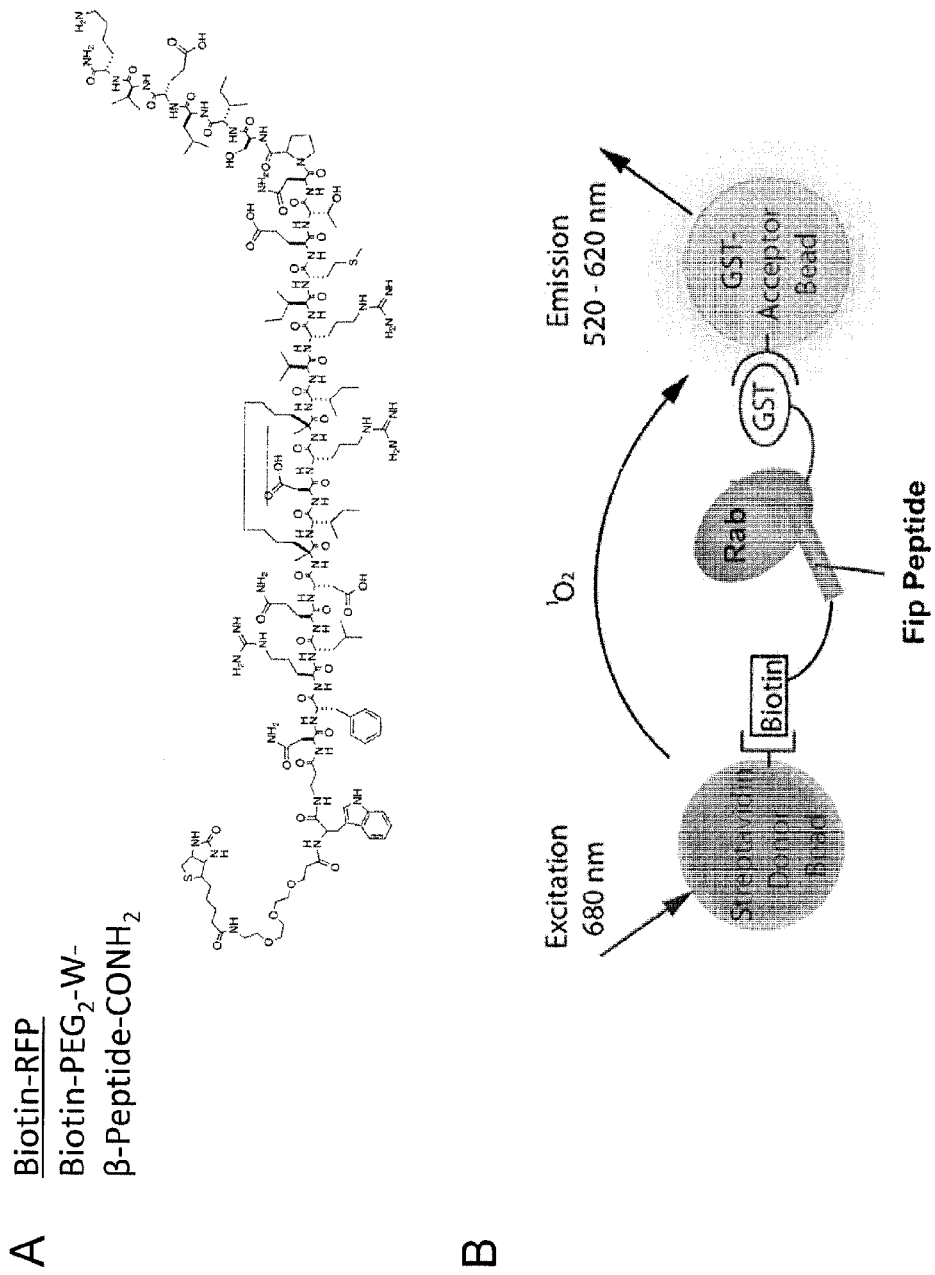
FIG. 13A shows an RFP conjugated to biotin.
FIG. 13B shows an overview of ALPHASCREEN® (Amplified Luminescent Proximity Homogenous Assay), showing FIP conjugated to biotin interacting with RAB conjugated to GST. Streptavadin serves as the donor bead, while anti-GST serves as the acceptor bead.
Figure 14:
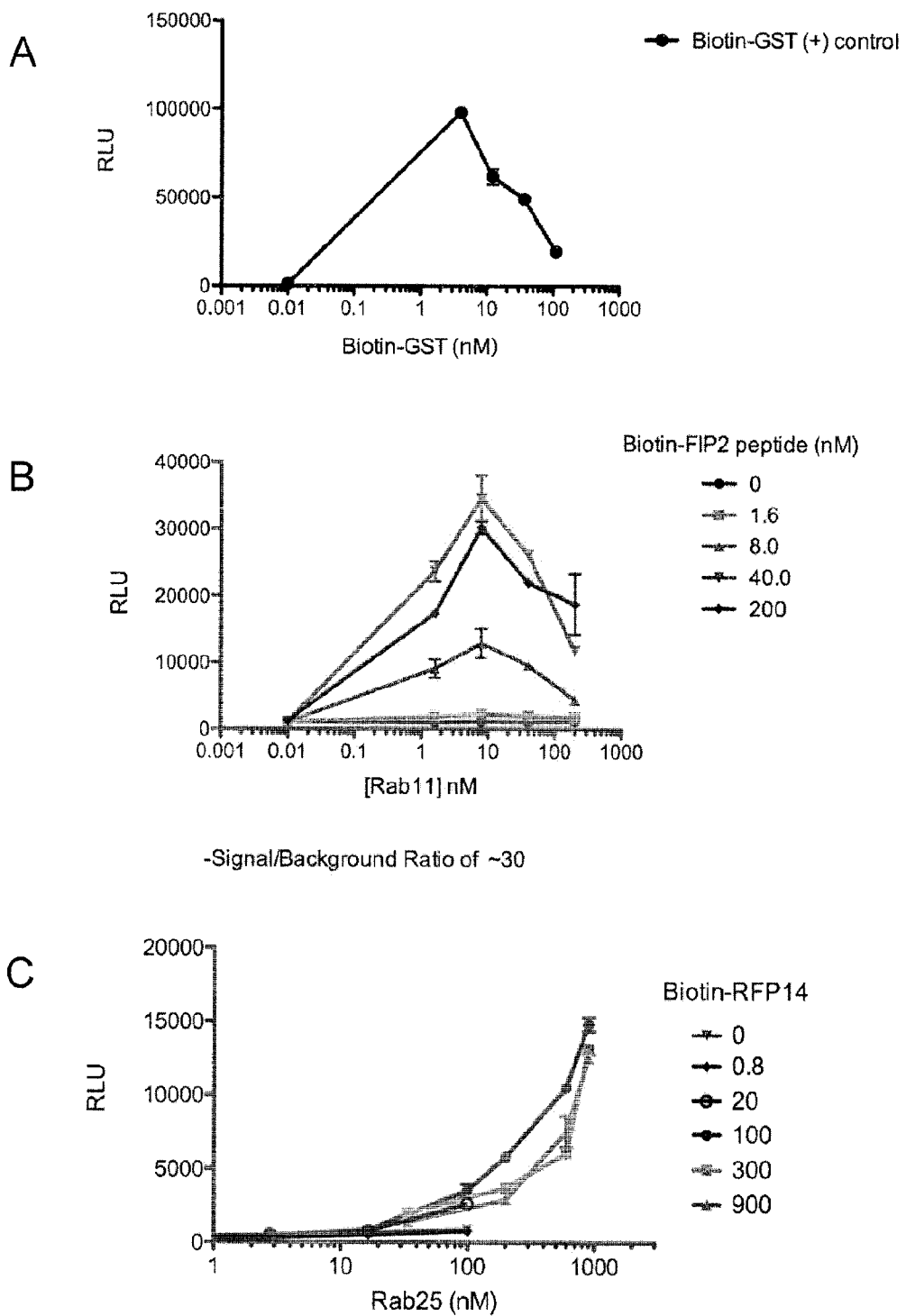
FIGS. 14A-14C are graphs demonstrating the relative light unit (RLU) of protein-ligand complexes obtained by ALPHASCREEN® assays. Protein-ligand complexes consisting of biotin and GST alone (control) (FIG. 14A), biotin-FIP2 and GST-RAB11 (FIG. 14B), and biotin-RFP14 and GST-$H_6$-RAB25 (SEQ ID NO: 86) (FIG. 14C) were incubated, with various concentrations of the biotin-labeled protein.
Figure 15:
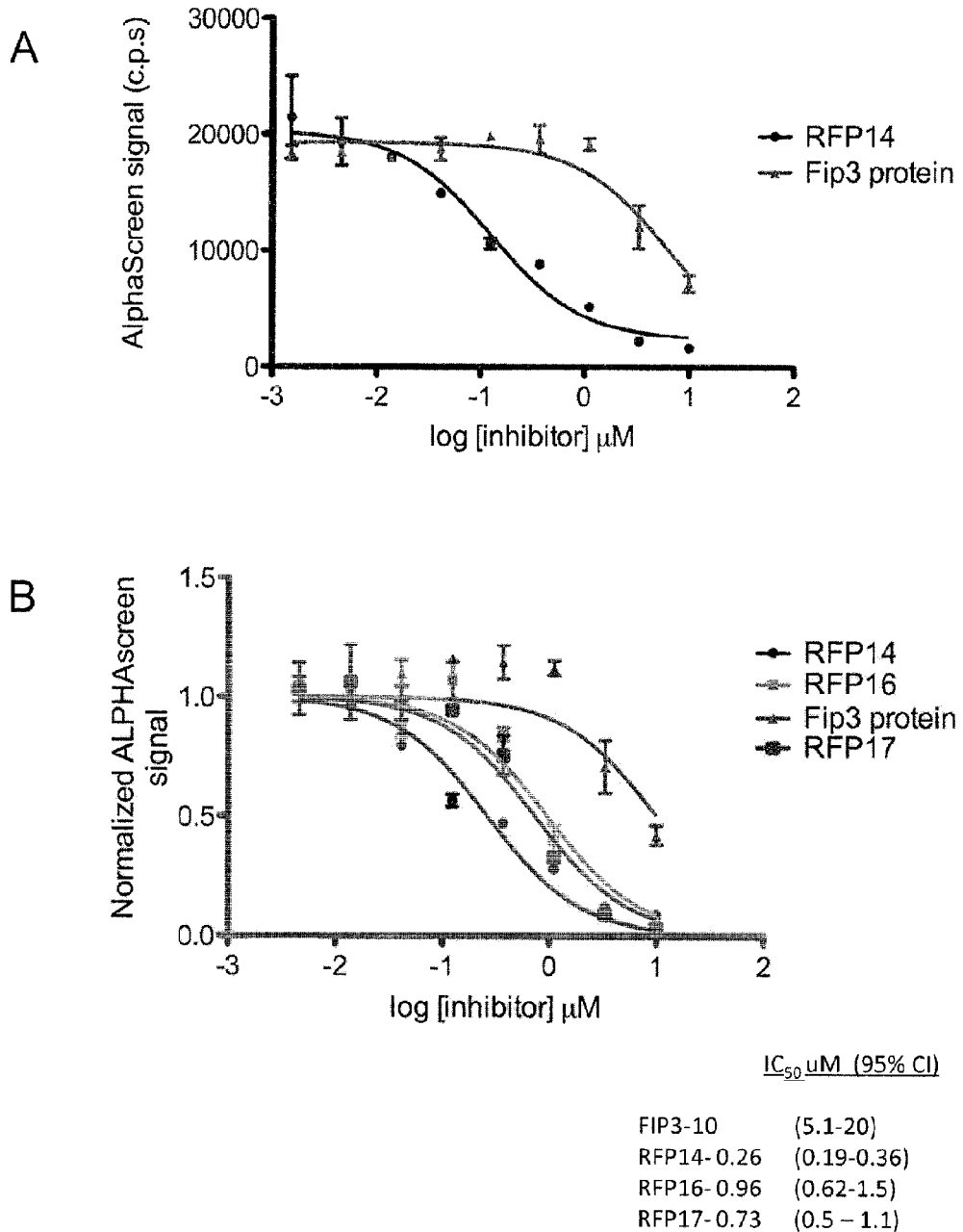
FIGS. 15A-15B are graphs demonstrating protein-ligand binding data obtained by ALPHASCREEN® competition assays: actual raw luminescent data (FIG. 15A); normalized data (FIG. 15B).

In FIGS. 13 and 14, the binding complex is pre-formed with Biotin-RFP14 and GST-$H_6$-RAB25 (SEQ ID NO: 86). Soluble competitors were then added after an incubation time (30 min) across a dose range. These competitors are FIP3 (expressed protein), and Trp-labeled derivatives of RFP14, RFP16 and RFP17. After another incubation of 30 min the streptavidin donor beads and Ni-NTA acceptor beads are added and the luminescent signal is measured approximately 30 min later (total of ~1.5 hr incubation time).

Binding of the competitors to RAB proteins prevented complex formation and luminescent signal. This finding indicated saturable binding to beads and thus specific binding events. Stapled FIP peptides competed with biotin-RFP14 for RAB25 binding (FIGS. 14A and 14B). FIP3 protein (652-756) also competed, although with a significantly higher $IC_{50}$. Relative $IC_{50}$s are similar to the $K_d$s observed for these peptides (or peptides of the corresponding proteins) for binding to RAB25, as measured by fluorescent polarization. Stapled FIP peptides are 10-to 40-fold more active than FIP3 protein. These results indicate that the RFP and FIP3 binding sites overlap, as each competes with the other for RAB25 binding.

Example 8

In Vitro Immunoprecipitation

Figure 16:
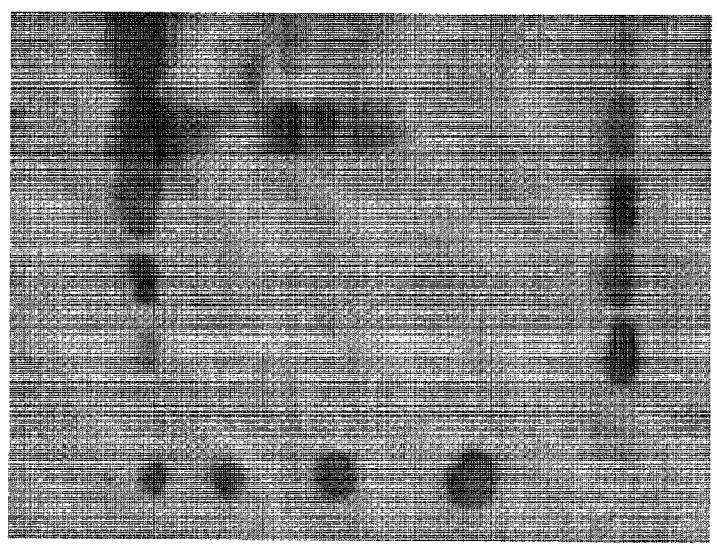
FIG. 16 is a western blot image, staining with an anti-GST antibody recognizing the GST-RAB25 fusion protein, from an immunoprecipitation assay demonstrating stable RFP/RAB complex formation.

Biotin-RFP or biotin-FIP peptides were immobilized on streptavidin-agarose beads and incubated with 150 nM of recombinant GST-$H_6$-RAB25 (SEQ ID NO: 86). After incubation, the beads were washed, and bound proteins were eluted by boiling. The proteins were then separated by electrophoresis on an SDS-PAGE gel, followed by transfer to nitrocellulose for western blot analysis. The resulting blot was stained with an anti-GST monoclonal antibody and visualized with an HRP-conjugated secondary antibody by luminescence. Compared to mock (no peptides), all peptides were found to retain increased GST-RAB25, with the RFPs showing the highest signal (FIG. 16). These results indicated that a stable complex of RFP-RAB11 can be formed and co-precipitated.

Example 9

Quantitative Epifluorescene Microscopy

Figure 17:
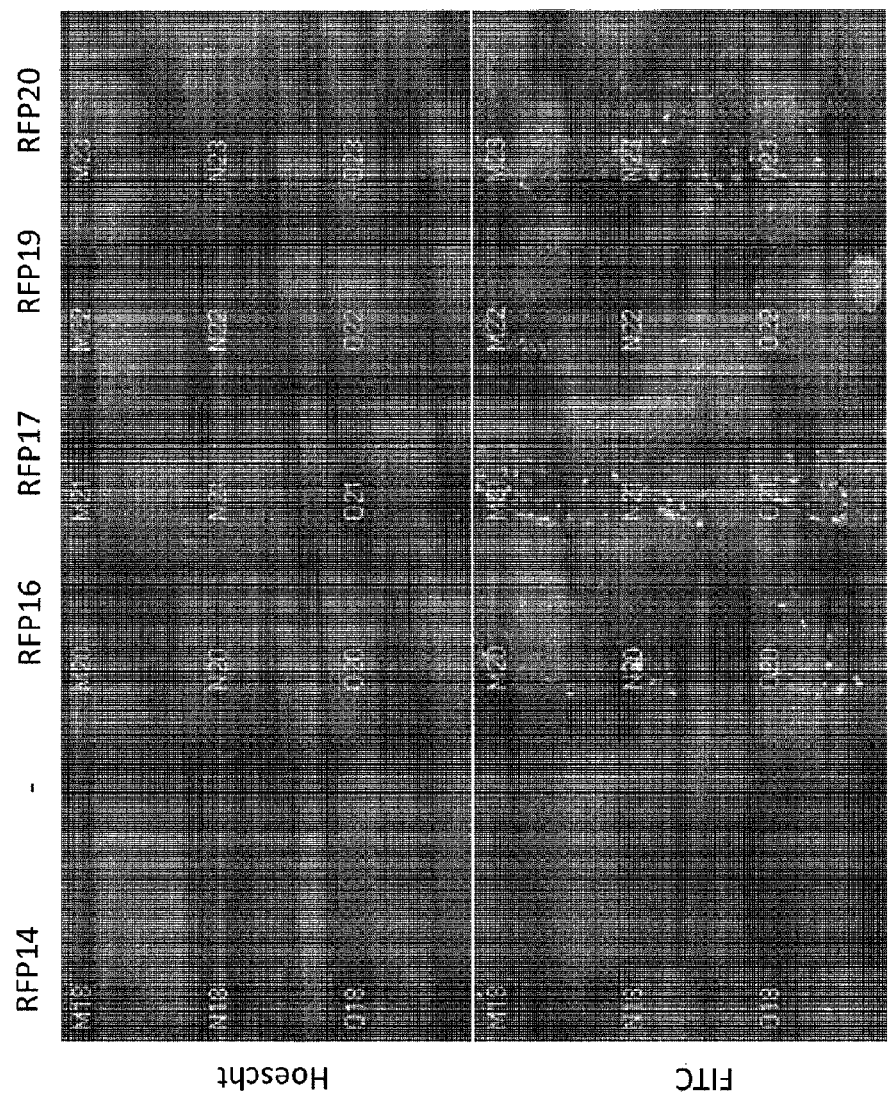
FIG. 17 shows fluorescent microscopy images at 20× magnification of U2OS osteosarcoma cells transfected with FITC-RFPs and stained with Hoescht nuclear dye. Hoescht (top panels); FITC (bottom panels).
Figure 18:
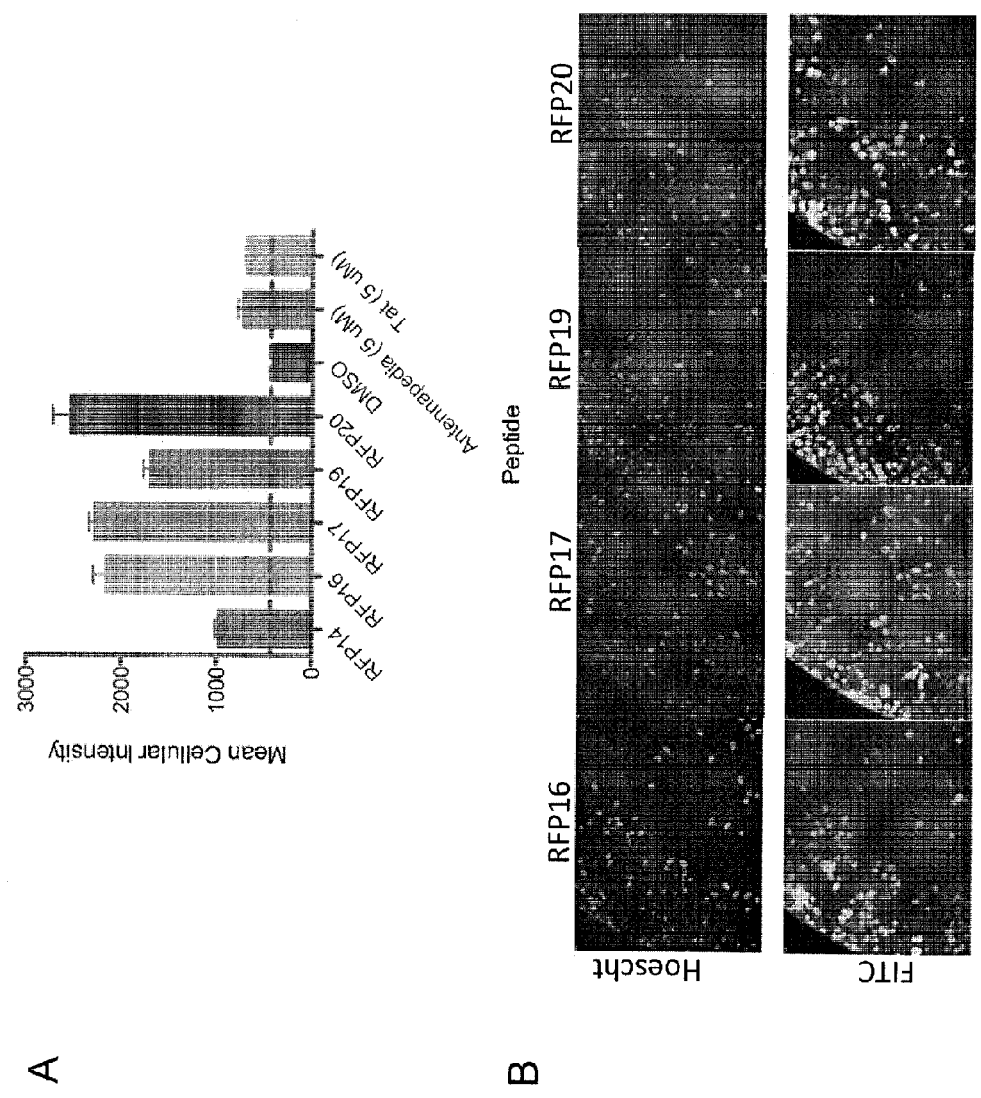
FIG. 18A is a graph quantifying epifluorescence of U2OS osteosarcoma cells transfected with FITC-RFPs, Antennapedia protein, or Tat protein.
FIG. 18B shows fluorescent microscopy images of U2OS osteosarcoma cells transfected with FITC-RFP peptides and stained with Hoescht nuclear dye. Hoescht (top panel); FITC (bottom panel).

U2OS osteosarcoma cells were treated with 5 μM FITC-RFPs for 12 hours in Dulbecco's Modified Eagle Medium (DMEM) (Gibco®) containing 10% fetal bovine serum (FBS). Cells were washed, then stained with Hoescht nuclear dye. Automated fluorescence microscopy was performed at 20× on an IX5000 epifluorescence microscope. Nuclear staining is shown in the top panel and FITC is show in the bottom panel (FIGS. 16 and 17B). Quantification was performed using MetaXpress software (FIG. 18A). RFPs showed higher cell penetration than traditional cell penetrating peptides (CPPs) Antennapedia and Tat under identical conditions (FIG. 18A). RFP14 showed the lowest cell penetration, which is perhaps related to lower net positive charge. These data indicate that these RFP peptides are capable of penetrating cells, which is a necessary, but not inherent, attribute for biologically active stapled peptides.

Example 10

Additional Staple FIP Peptide Designs

Figure 19:
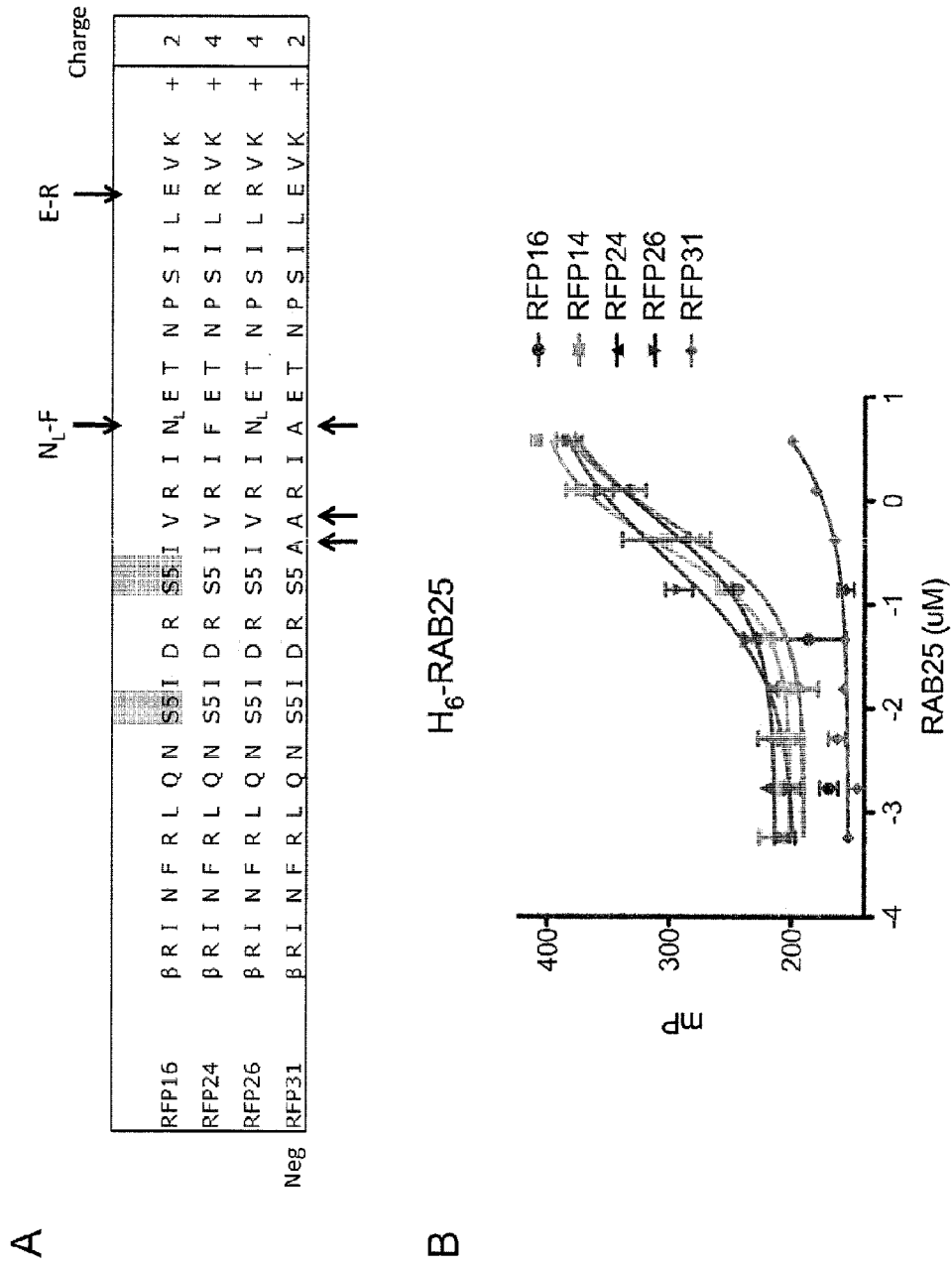
FIG. 19A describes a panel of RFPs containing an E-R mutation to increase overall charge (RFP24 and RFP26) and a triple-alanine mutant negative control (RFP31) (SEQ ID NOs: 77, 82-84 from top to bottom).
FIG. 19B is a graph showing the binding affinities of the RFPs to RAB25. $H_6$ is SEQ ID NO: 86.
Figure 20:
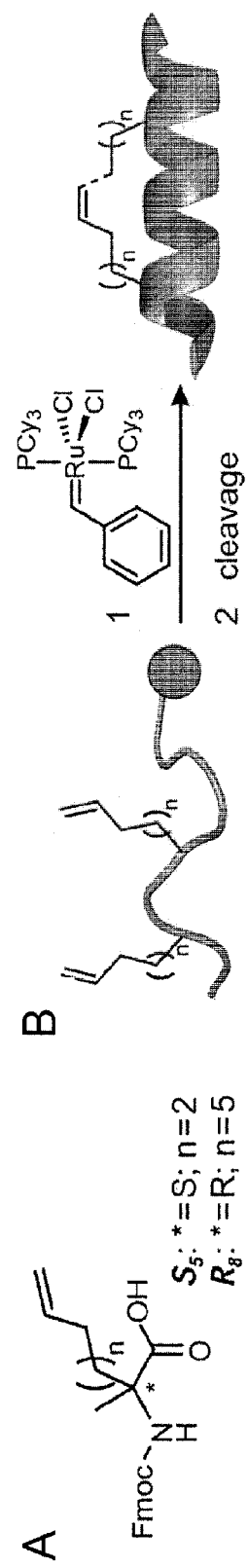
FIG. 20A depicts α,α-disubstituted non-natural amino acids that are used to introduce the olefin function into a peptide sequence.
FIG. 20B depicts Ru-catalyzed metathesis used to form the olefin staple on solid support.

Previous studies have indicated that stapled peptides with a net formal charge of +2 to +4 at physiologic pH show the highest cellular uptake and are thus generally more potent. With this in mind, we sought to design derivatives of RFP14 and RFP16/17 that retained binding affinity but have a higher net positive charge. We also sought to design a corresponding negative control peptide with decreased binding affinity. RFP24 and RFP26 peptides containing an E-R mutation to increase overall charge were designed next (FIG. 19A). Both peptides retained binding affinity. RFP31, a triple-alanine mutant negative control (the I/V/M residues form hydrophobic contacts with RAB25 from structural studies), showed an approximate 100-fold decrease in binding affinity, indicating a specific binding interaction, which is a useful negative control (FIG. 19B).

Figure 21:
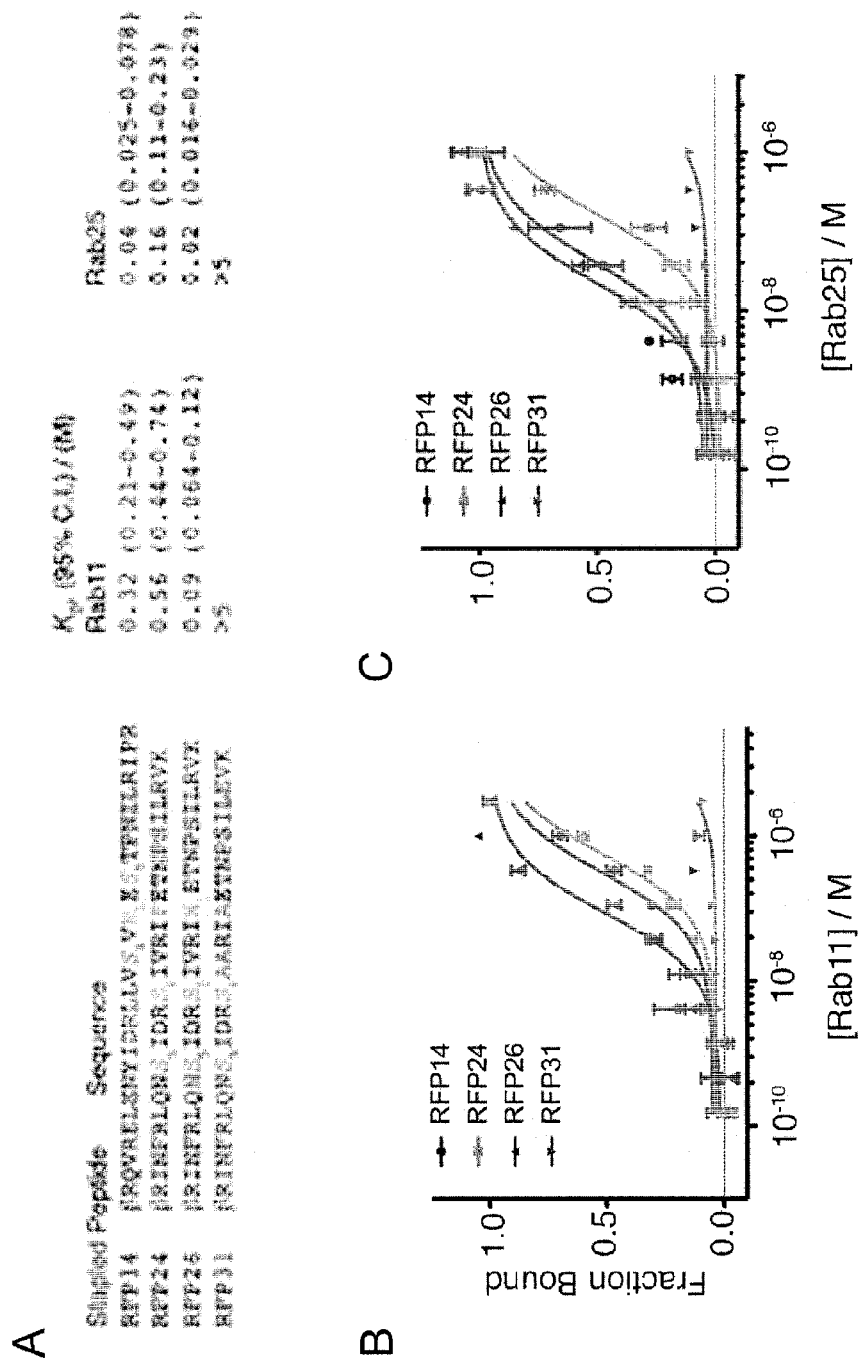
FIG. 21A is a panel of optimized RFPs (RFP14 (SEQ ID NO: 75), RFP24 SEQ ID NO: 82) and RFP26 (SEQ ID NO: 83)) and triple-alanine mutant negative control RFP31 (SEQ ID NO: 84) with staple positions highlighted.
FIG. 21B is a graph demonstrating relative affinities of RFP14, RFP24, RFP26 and RFP31 for RAB11.
FIG. 21C is a graph demonstrating relative affinities of RFP14, RFP24, RFP26 and RFP31 for RAB25.

The optimized RFP compounds were tested for binding to RAB 11 or RAB25 (FIG. 21). RFP26 showed high affinity for both RAB11 (FIG. 21B) and RAB25 (FIG. 21C), with some selectivity for RAB25. The RFP31 negative control showed negligible affinity for RAB11 and negligible affinity for RAB25.

Figure 22:
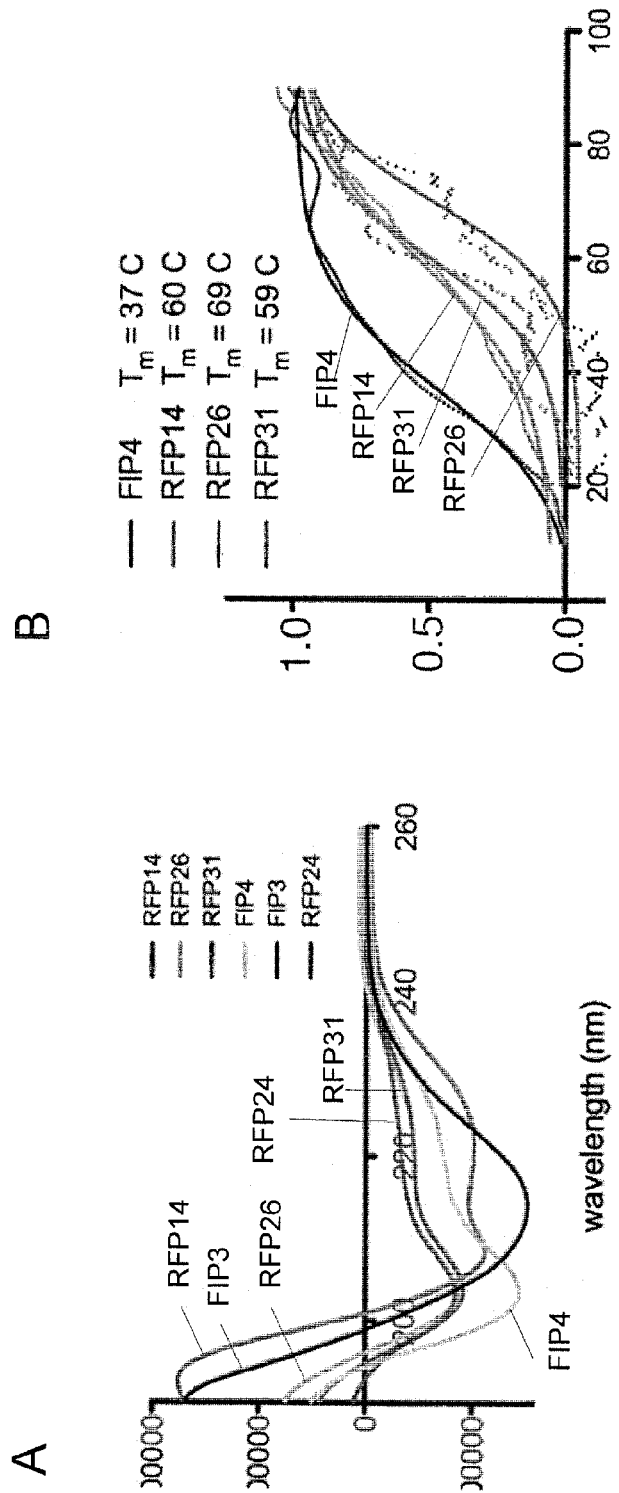
FIG. 22A and FIG. 22B depict circular dichroism (CD). Optimized RFP compounds show significant thermal stability relative to unmodified FIP4 peptide, as measured by thermal unfolding.

The optimized RFP compounds also showed significant thermal stability relative to unmodified FIP4 peptide, as measured by thermal unfolding by circular dichroism (measured at 222 nm) (FIG. 22).

Figure 23:
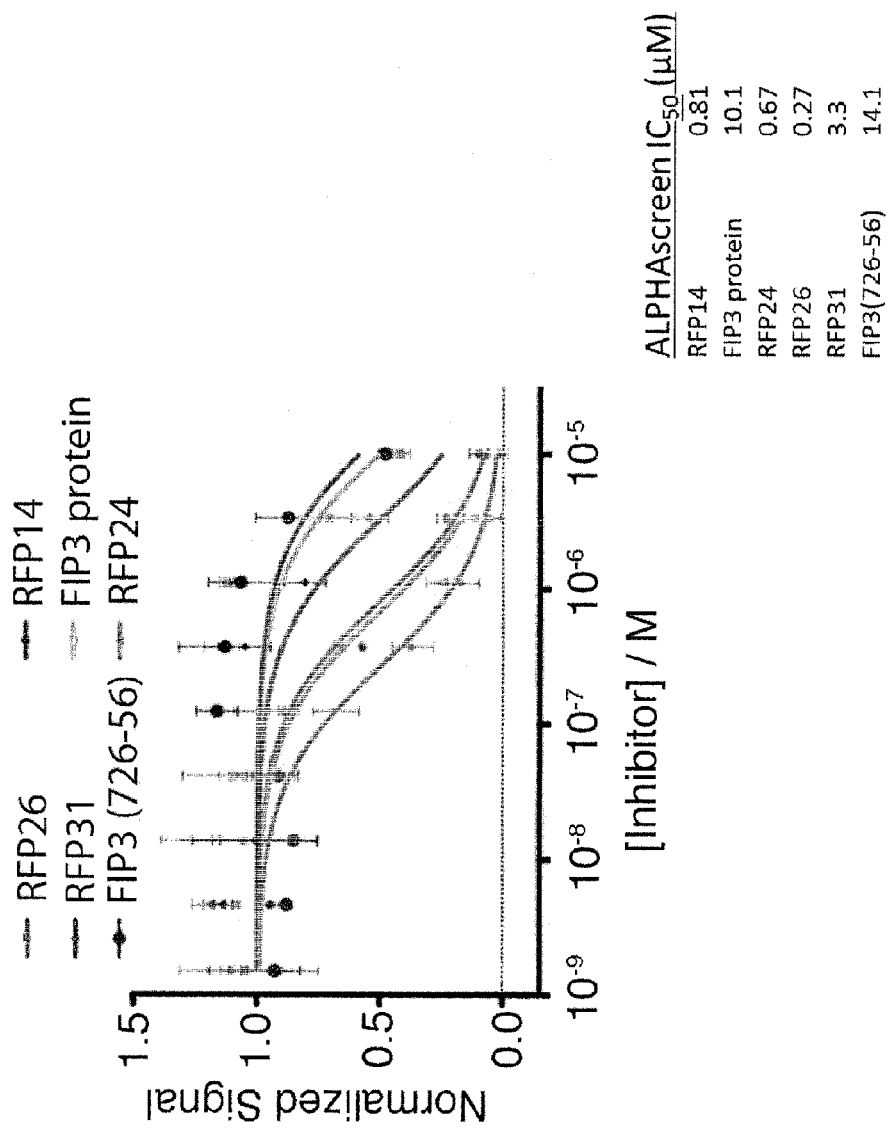
FIG. 23 is a graph demonstrating normalized protein-ligand binding data obtained by ALPHASCREEN® competition assays.

Additional studies showed that the optimized RFP compounds inhibited RAB25-FIP peptide interation in ALPHASCREEN® competition assays (FIG. 23).

Example 11

Human Ovarian Carcinoma Cell (OVCAR3) Binding and Phosphorylation Studies

Figure 24:
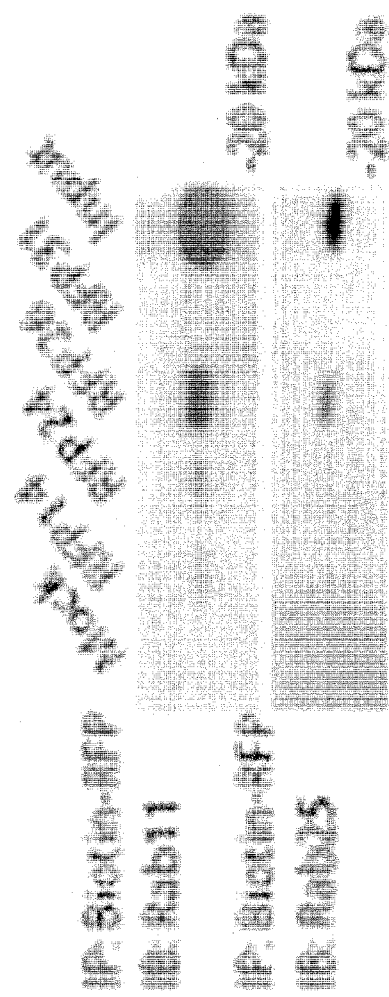
FIG. 24 shows a Western blot image of RAB11 and RAB25 proteins eluted from binding assays with optimized compounds RFP14, RFP24 and RFP26 and triple-alanine mutant negative control RFP31.

Optimized RFP peptides were synthesized with an amino-terminal diethyleneglycol-biotin moiety. The peptides were immobilized on streptavidin-agarose resin/beads and incubated in pre-cleared lysate from OVCAR3 cells, which express RAB11 and RAB25. The beads were washed, and the protein was eluted and used for Western blot analysis to identify retained RAB11 and RAB25 (FIG. 24). RFP26 showed significant binding to and retention of RAB11 and RAB25, relative to mock or negative control RFP31 peptide. The signal is similar to the relative binding affinities and ALPHASCREEN® $IC_{50}$ observed for RFP peptides.

Figure 25:
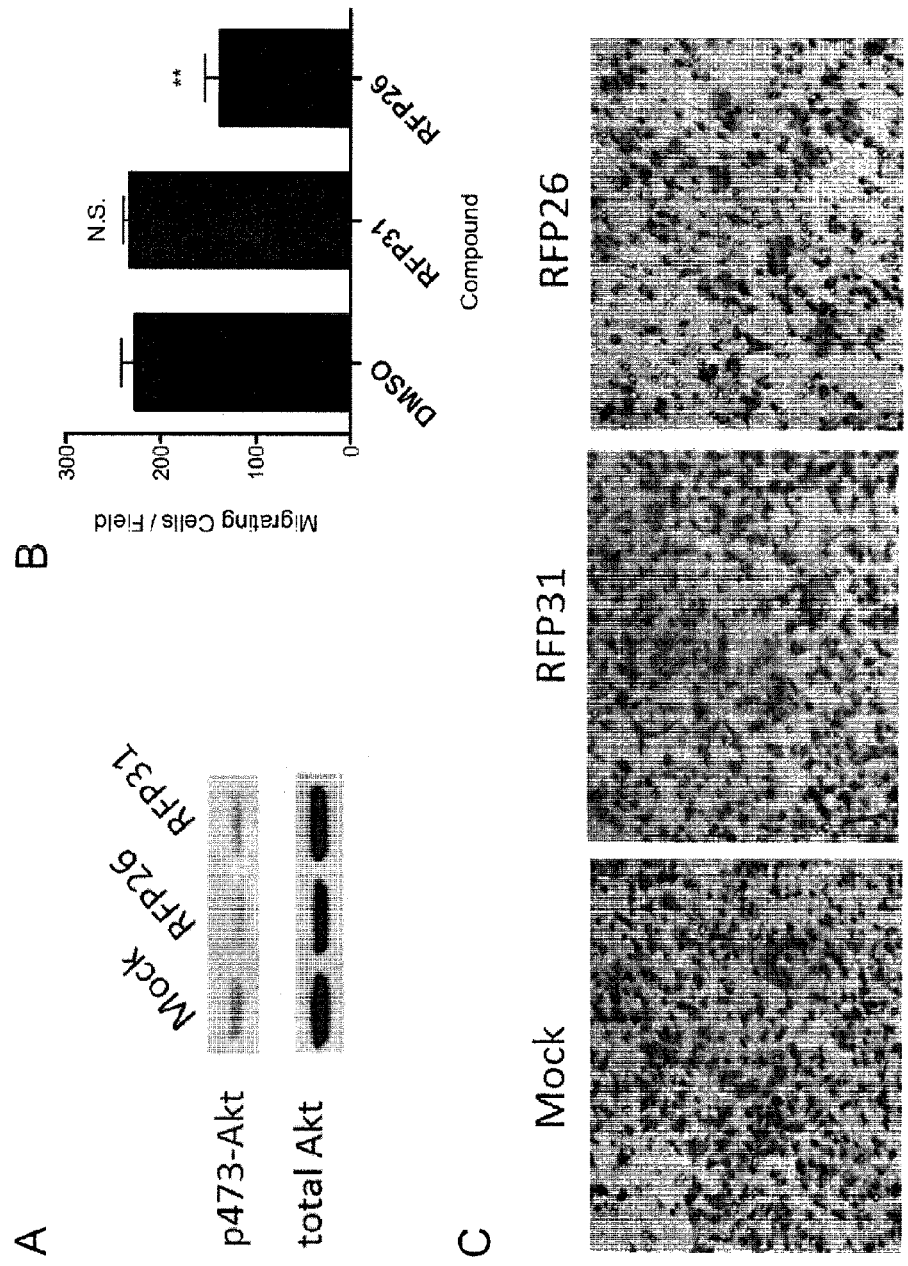
FIG. 25A show a Western blot image of p473-Akt (Akt phosphorylated at S473) and total Akt from OVCAR3 cells (Human Ovarian Carcinoma cell line) treated with RFP26 or RFP31.
FIG. 25B is a graph quantifying migrating RFP-treated OVCR3 cells using a transwell migration assay.
FIG. 25C shows microscopy images of migrating cells fixed and stained.

AKT, also known as Protein Kinase B (PKB), is a serine/threonine-specific protein kinase that is associated with tumor cell survival, proliferation, and invasiveness. The activation of AKT is also one of the most frequent alterations observed in human cancer and tumor cells, thus deregulation of the AKT plays a pivotal role in tumor biology (Stuenaes et al., *Br. J. Pharmacol.* (2010) 160(1): 116-29). Full AKT activation requires phosphorylation by activating kinases on two residues: threonine 308 (T308) and serine 473 (S473). Hyperactivation of AKT is associated with resistance to apoptosis as well as increased cell proliferation and metabolism. Transfecting OVCAR3 cells with siRNA against RAB25 showed reduced AKT phosphorylation at S473 (p473-AKT), consistant with previous studies (Cheng et al., *Nat. Med.* (2004) 11:1251-6). To assess the affect of RFP26 on AKT phosphorylation in OVCAR3 cells, OVCAR3 cells were treated with 1082 M RFP26 for 24 hours. The cells were then lysed, and the lysate was used in a Western blot to detect AKT phosphorylated at S473 (p473-AKT) and total AKT (FIG. 25A). Results showed that RFP26 treatment decreased AKT phosphorylation at S473.

Further anlaysis using a transwell migration assay showed that RFP26 treatment inhibited OVCAR3 cellular migration. OVCAR3 cells were seeded on collagen-coated, 8-micron transwells in DMEM media. Cells were treated with 15 μM RFP26, RFP31 or vehicle for 24 hours during cell migration. The cells in the wells were fixed, and migrating cells were stained and counted (FIGS. 25B and 25C).

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

The invention claimed is:

1. An unstapled polypeptide of Formula (I):

$$R^f\text{-}[X_{AA}]_s\text{-}[X_{1\text{-}26}]\text{-}[X_{AA}]_t\text{-}R^e \quad (I)$$

or a pharmaceutically acceptable salt thereof;

wherein:

each instance of $X_{AA}$ is a natural amino acid or an unnatural amino acid;

s is 0 or an integer between 1 and 100, inclusive;

t is 0 or an interger between 1 and 100, inclusive;

$R^f$ is an N-terminal group selected from the group consisting of hydrogen; optionally substituted aliphatic; optionally substituted heteroaliphatic; optionally substituted aryl; optionally substituted heteroaryl; acyl; a resin; an amino protecting group; and a label optionally joined by a linker, wherein the linker is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; and acylene;

$R^e$ is a C-terminal group selected from the group consisting of hydrogen; optionally substituted aliphatic; optionally substituted heteroaliphatic; optionally substituted aryl; optionally substituted heteroaryl; $-OR^E$, $-N(R^E)_2$, or $-SR^E$, wherein each instance of $R^E$ is, independently, hydrogen; optionally substituted aliphatic; optionally substituted heteroaliphatic; optionally substituted aryl; optionally substituted heteroaryl; acyl; a resin; a protecting group; or two $R^E$ groups taken together form an optionally substituted heterocyclic or optionally substituted heteroaryl ring;

-$[X_{1\text{-}26}]$- is an unstapled amino acid sequence of the formula:

$$\text{-}[X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}$$
$$X_{15}\text{-}X_{16}\text{-}X_{17}\text{-}X_{18}\text{-}X_{19}\text{-}X_{20}\text{-}X_{21}\text{-}X_{22}\text{-}X_{23}\text{-}X_{24}\text{-}X_{25}\text{-}X_{26}]\text{-}$$

wherein:

$X_1$ is an amino acid selected from the group consisting of Q, H, and I;

$X_2$ is an amino acid selected from the group consisting of V, I, and N;

$X_3$ is an amino acid selected from the group consisting of R and F;

$X_4$ is an amino acid selected from the group consisting of E and R;

$X_5$ is amino acid L;

$X_6$ is an amino acid selected from the group consisting of E, Q, and R;
$X_7$ is an amino acid selected from the group consisting of D, Q, and an amino acid of formula (i);
$X_8$ is an amino acid selected from the group consisting of Y and an amino acid of formula (i);
$X_9$ is an amino acid selected from the group consisting of I and M;
$X_{10}$ is amino acid D;
$X_{11}$ is an amino acid selected from the group consisting of N, R, K, and an amino acid of formula (i) or (ii);
$X_{12}$ is an amino acid selected from the group consisting of L, I, and an amino acid of formula (i) or (ii);
$X_{13}$ is an amino acid selected from the group consisting of L and I;
$X_{14}$ is an amino acid selected from the group consisting of V and L;
$X_{15}$ is an amino acid selected from the group consisting of R, A, and an amino acid of formula (i) or (ii);
$X_{16}$ is an amino acid selected from the group consisting of V and I;
$X_{17}$ is an amino acid selected from the group consisting of M and L;
$X_{18}$ is an amino acid selected from the group consisting of E and D;
$X_{19}$ is an amino acid selected from the group consisting of E, T, H and an amino acid of formula (i);
$X_{20}$ is an amino acid selected from the group consisting of T and N;
$X_{21}$ is amino acid P;
$X_{22}$ is an amino acid selected from the group consisting of N and S;
$X_{23}$ is amino acid I;
$X_{24}$ is amino acid L;
$X_{25}$ is an amino acid selected from the group consisting of R and E;
$X_{26}$ is an amino acid selected from the group consisting of I and V;
provided that the amino acid sequence comprises at least two independent occurrences of an amino acid of formula (i) or (ii);
wherein the amino acid of formula (i) is:

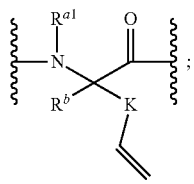

and the amino acid of Formula (ii) is:

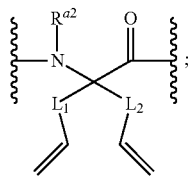

wherein:
each instance of K, $L_1$, and $L_2$, is, independently, optionally substituted alkylene; optionally substituted heteroalkylene; optionally substituted arylene; or optionally substituted heteroarylene;
each instance of $R^{a1}$ and $R^{a2}$ is, independently, hydrogen; optionally substituted aliphatic; optionally substituted heteroaliphatic; optionally substituted aryl; optionally substituted heteroaryl; acyl; or an amino protecting group; and
each instance of $R^b$ is, independently, hydrogen; optionally substituted aliphatic; optionally substituted heteroaliphatic; optionally substituted aryl; or optionally substituted heteroaryl.

2. A stapled polypeptide of the Formula (II):

$$R^f\text{-}[X_{AA}]_s\text{-}[X_{1\text{-}26}]\text{-}[X_{AA}]_t\text{-}R^e \qquad (II)$$

or a pharmaceutically acceptable salt thereof;
wherein:
each instance of $X_{AA}$ is a natural amino acid or unnatural amino acid;
s is 0 or an integer between 1 and 100, inclusive;
t is 0 or an integer between 1 and 100, inclusive;
$R^f$ is an N-terminal group selected from the group consisting of hydrogen; optionally substituted aliphatic; optionally substituted heteroaliphatic; optionally substituted aryl; optionally substituted heteroaryl; acyl; a resin; an amino protecting group; and a label optionally joined by a linker, wherein the linker is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; and acylene;
$R^e$ is a C-terminal group selected from the group consisting of hydrogen; optionally substituted aliphatic; optionally substituted heteroaliphatic; optionally substituted aryl; optionally substituted heteroaryl; —$OR^E$, —$N(R^E)_2$, or —$SR^E$, wherein each instance of $R^E$ is, independently, hydrogen; optionally substituted aliphatic; optionally substituted heteroaliphatic; optionally substituted aryl; optionally substituted heteroaryl; acyl; a resin; a protecting group; or two $R^E$ groups taken together form an optionally substituted heterocyclic or optionally substituted heteroaryl ring; and
-$[X_{1-26}]$- is a stapled amino sequence of the Formula:

$$-[X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}$$
$$X_{15}\text{-}X_{16}\text{-}X_{17}\text{-}X_{18}\text{-}X_{19}\text{-}X_{20}\text{-}X_{21}\text{-}X_{22}\text{-}X_{23}\text{-}X_{24}\text{-}X_{25}\text{-}X_{26}]\text{-}$$

wherein:
$X_1$ is an amino acid selected from the group consisting of Q, H, and I;
$X_2$ is an amino acid selected from the group consisting of V, I, and N;
$X_3$ is an amino acid selected from the group consisting of R and F;
$X_4$ is an amino acid selected from the group consisting of E and R;
$X_5$ is amino acid L;
$X_6$ is an amino acid selected from the group consisting of E, Q and R;
$X_7$ is an amino acid selected from the group consisting of D and Q, or $X_7$ and $X_{11}$ are stapled amino acids of Formula (iii), or $X_7$, $X_{11}$ and $X_{15}$ are stapled amino acids of Formula (iv);

$X_8$ is amino acid Y, or $X_8$ and $X_{12}$ are stapled amino acids of Formula (iii);

$X_9$ is an amino acid selected from the group consisting of I and M;

$X_{10}$ is amino acid D;

$X_{11}$ is an amino acid selected from the group consisting of N, R, and K, or $X_7$ and $X_{11}$ are stapled amino acids of Formula (iii), or $X_7$, $X_{11}$ and $X_{15}$ are stapled amino acids of Formula (iv), or $X_{11}$, $X_{15}$ and $X_{19}$ are stapled amino acids of Formula (iv);

$X_{12}$ is an amino acid selected from the group consisting of L and I, or $X_8$ and $X_{12}$ are stapled amino acids of Formula (iii), or $X_{12}$ and $X_{15}$ are stapled amino acids of Formula (iii);

$X_{13}$ is an amino acid selected from the group consisting of L and I;

$X_{14}$ is an amino acid selected from the group consisting of V and L;

$X_{15}$ is an amino acid selected from the group consisting of R and A, or $X_{12}$ and $X_{15}$ are stapled amino acids of Formula (iii); or $X_{15}$ and $X_{19}$ are stapled amino acids of Formula (iii), or $X_7$, $X_{11}$, and $X_{15}$ are stapled amino acids of Formula (iv), or $X_{11}$, $X_{15}$, and $X_{19}$ are stapled amino acids of Formula (iv);

$X_{16}$ is an amino acid selected from the group consisting of V and I;

$X_{17}$ is an amino acid selected from the group consisting of M and L;

$X_{18}$ is an amino acid selected from the group consisting of E and D;

$X_{19}$ is E, T, or H, or $X_{15}$ and $X_{19}$ are stapled amino acids of Formula (iii), or $X_{11}$, $X_{15}$, and $X_{19}$ are stapled amino acids of Formula (iv);

$X_{20}$ is an amino acid selected from the group consisting of T and N;

$X_{21}$ is amino acid P;

$X_{22}$ is an amino acid selected from the group consisting of N and S;

$X_{23}$ is amino acid I;

$X_{24}$ is amino acid L;

$X_{25}$ is an amino acid selected from the group consisting of R and E;

$X_{26}$ is an amino acid selected from the group consisting of I and V;

provided that the amino acid sequence comprises at least one occurrence of stapled amino acids of Formula (iii) or (iv); wherein the stapled amino acids of Formula (iii) is:

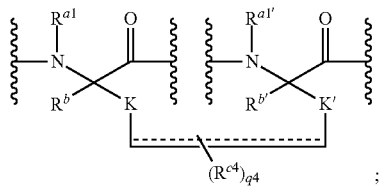

and wherein the stapled amino acids of Formula (iv) is:

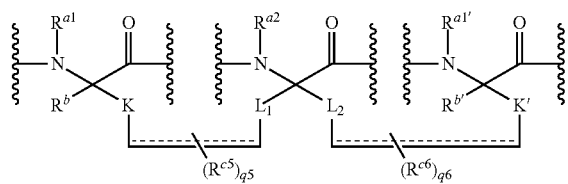

wherein:

each instance of K, K', $L_1$, and $L_2$, is, independently, optionally substituted alkylene; optionally substituted heteroalkylene; optionally substituted arylene; or optionally substituted heteroarylene;

each instance of $R^{a1}$, $R^{a1'}$, and $R^{a2}$ is, independently, hydrogen; optionally substituted aliphatic; optionally substituted heteroaliphatic; optionally substituted aryl; optionally substituted heteroaryl; acyl; or an amino protecting group;

each instance of $R^b$ and $R^{b'}$ is, independently, hydrogen; optionally substituted aliphatic; optionally substituted heteroaliphatic; optionally substituted aryl; optionally substituted heteroaryl;

each instance of ==== independently represents a single or double bond;

each instance of $R^{c4}$, $R^{c5}$, and $R^{c6}$ is independently hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro; and each instance of $q^{c4}$, $q^{c5}$, and $q^{c6}$ is independently 0, an integer between 1 and 2 when ==== represents a double bond, or an integer between 1 and 4, inclusive, when ==== represents a single bond.

3. The polypeptide of claim 2, wherein the amino acid sequence is alpha helical.

4. The polypeptide of claim 2, wherein the amino acid sequence comprises a Rab binding domain (RabBD).

5. The polypeptide of claim 2, wherein the amino acid sequence is a modified amino acid sequence corresponding to residues 1247-1272 of Fip1:

(SEQ ID NO: 9)
-Q-V-R-E-L-E-$X_7$-$X_8$-I-D-$X_{11}$-$X_{12}$-L-V-$X_{15}$-V-M-E-$X_{19}$-

T-P-N-I-L-R-I-.

6. The polypeptide of claim 2, wherein the amino acid sequence is a modified amino acid sequence corresponding to residues 473-498 of Fip2:

(SEQ ID NO: 10)
-H-I-R-E-L-E-$X_7$-$X_8$-I-D-$X_{11}$-$X_{12}$-L-V-$X_{15}$-V-M-E-$X_{19}$-

T-P-S-I-L-R-V-.

7. The polypeptide of claim 2, wherein the amino acid sequence is a modified amino acid sequence corresponding to residues 730-757 of Fip3:

(SEQ ID NO: 11)
-I-N-F-R-L-Q-$X_7$-$X_8$-I-D-$X_{11}$-$X_{12}$-I-V-$X_{15}$-I-M-E-$X_{19}$-

N-P-S-I-L-E-V-.

8. The polypeptide of claim 2, wherein the amino acid sequence is a modified amino acid sequence corresponding to residues 610-635 of Fip4:

(SEQ ID NO: 12)
-I-N-F-R-L-R-X$_7$-X$_8$-M-D-X$_{11}$-X$_{12}$-I-L-X$_{15}$-I-L-D-X$_{19}$-

N-P-S-I-L-E-I-.

9. The polypeptide of claim 2, wherein the amino acid sequence is selected from the group consisting of:

(SEQ ID NO: 13; Fip 1 X$_7$-X$_{11}$; "YID")
-Q-V-R-E-L-E-*-Y-I-D-*-L-L-V-R-V-M-E-E-T-P-N-I-L-

R-I-;

(SEQ ID NO: 14; Fip 1 X$_8$-X$_{12}$; "IDN")
-Q-V-R-E-L-E-D-*-I-D-N-*-L-V-R-V-M-E-E-T-P-N-I-L-

R-I-;

(SEQ ID NO: 15; Fip 1 X$_{11}$-X$_{15}$; "LLV")
-Q-V-R-E-L-E-D-Y-I-D-*-L-L-V-*-V-M-E-E-T-P-N-I-L-

R-I-;

(SEQ ID NO: 16; Fip 1 X$_{15}$-X$_{19}$ "VME")
-Q-V-R-E-L-E-D-Y-I-D-N-L-L-V-*-V-M-E-*-T-P-N-I-L-

R-I-;

(SEQ ID NO: 17; Fip 1 X$_7$-X$_{11}$-X$_{15}$)
-Q-V-R-E-L-E-*-Y-I-D-^-L-L-V-*-V-M-E-E-T-P-N-I-L-

R-I-;

(SEQ ID NO: 18; Fip 1 X$_{11}$-X$_{15}$-X$_{19}$)
-Q-V-R-E-L-E-D-Y-I-D-*-L-L-V-^-V-M-E-*-T-P-N-I-L-

R-I-;

(SEQ ID NO: 19; Fip 2 X$_7$-X$_{11}$ "YID")
-H-I-R-E-L-E-*-Y-I-D-*-L-L-V-R-V-M-E-E-T-P-S-I-L-

R-V-;

(SEQ ID NO: 20; Fip 2 X$_8$-X$_{12}$ "IDN")
-H-I-R-E-L-E-D-*-I-D-N-*-L-V-R-V-M-E-E-T-P-S-I-L-

R-V-;

(SEQ ID NO: 21; Fip 2 X$_{11}$-X$_{15}$ "LLV")
-H-I-R-E-L-E-D-Y-I-D-*-L-L-V-*-V-M-E-R-T-P-S-I-L-

R-V-;

(SEQ ID NO: 22; Fip 2 X$_{15}$-X$_{19}$ "VME")
-H-I-R-E-L-E-D-Y-I-D-N-L-L-V-*-V-M-E-*-T-P-S-I-L-

R-V-;

(SEQ ID NO: 23; Fip 2 X$_7$-X$_{11}$-X$_{15}$)
-H-I-R-E-L-E-*-Y-I-D-^-L-L-V-*-V-M-E-E-T-P-S-I-L-

R-V-;

(SEQ ID NO: 24; Fip 2 X$_{11}$-X$_{15}$-X$_{19}$)
-H-I-R-E-L-E-D-Y-I-D-*-L-L-V-^-V-M-E-*-T-P-S-I-L-

R-V-;

(SEQ ID NO: 25; Fip 3 X$_7$-X$_{11}$ "YID")
-I-N-F-R-L-Q-*-Y-I-D-*-I-I-V-A-I-M-E-T-N-P-S-I-L-

E-V-;

(SEQ ID NO: 26; Fip 3 X$_8$-X$_{12}$ "IDR")
-I-N-F-R-L-Q-D-*-I-D-R-*-I-V-A-I-M-E-T-N-P-S-I-L-

E-V-;

(SEQ ID NO: 27; Fip 3 X$_{11}$-X$_{15}$ "IIV")
-I-N-F-R-L-Q-D-Y-I-D-*-I-I-V-*-I-M-E-T-N-P-S-I-L-

E-V-;

(SEQ ID NO: 28; Fip 3 X$_{15}$-X$_{19}$ "IME")
-I-N-F-R-L-Q-D-Y-I-D-R-I-I-V-*-I-M-E-*-N-P-S-I-L-

E-V-;

(SEQ ID NO: 29; Fip 3 X$_7$-X$_{11}$-X$_{15}$)
-I-N-F-R-L-Q-*-Y-I-D-^-I-I-V-*-I-M-E-T-N-P-S-I-L-

E-V-;

(SEQ ID NO: 30; Fip 3 X$_{11}$-X$_{15}$-X$_{19}$)
-I-N-F-R-L-Q-D-Y-I-D-*-I-I-V-^-I-M-E-*-N-P-S-I-L-

E-V-;

(SEQ ID NO: 31; Fip 4 X$_7$-X$_{11}$ "YMD")
-I-N-F-R-L-R-*-Y-M-D-*-I-I-L-A-I-L-D-H-N-P-S-I-L-

E-I-;

(SEQ ID NO: 32; Fip 4 X$_8$-X$_{12}$ "MDK")
-I-N-F-R-L-R-Q-*-M-D-K-*-I-L-A-I-L-D-H-N-P-S-I-L-

E-I-;

(SEQ ID NO: 33; Fip 4 X$_{11}$-X$_{15}$ "IIL")
-I-N-F-R-L-R-Q-Y-M-D-*-I-I-L-*-I-L-D-H-N-P-S-I-L-

E-I-;

(SEQ ID NO: 34; Fip 4 X$_{15}$-X$_{19}$ "ILD")
-I-N-F-R-L-R-Q-Y-M-D-K-I-I-L-*-I-L-D-*-N-P-S-I-L-

E-I-;

(SEQ ID NO: 35; Fip 4 X$_7$-X$_{11}$-X$_{15}$)
-I-N-F-R-L-R-*-Y-M-D-^-I-I-L-*-I-L-D-H-N-P-S-I-L-

E-I-;
and (SEQ ID NO: 36; Fip 4 X$_{11}$-X$_{15}$-X$_{19}$)
-I-N-F-R-L-R-Q-Y-M-D-*-I-I-L-^-I-L-D-*-N-P-S-I-L-

E-I-;

wherein the amino acid sequence corresponds to an unstapled amino acid sequence if:

(1) the amino acid sequence comprises two amino acids symbolized by an asterix (*), and each instance of the symbol (*) independently corresponds to an amino acid of the Formula (i); or (2) the amino acid sequence comprises an amino acid symbolized by a carrot (^) and two amino acids symbolized by the asterix (*), and each instance of the symbol (^) corresponds to an amino acid of Formula (ii) and each instance of the symbol (*) independently corresponds to the amino acid of (i);

and wherein the amino acid sequence corresponds to a stapled amino acid sequence if:

(1) the amino acid sequence comprises two amino acids symbolized by an asterix (*), and each instance of the symbol (*) independently corresponds to two stapled amino acids of the Formula (iii); or (2) the amino acid sequence comprises an amino acid symbolized by a carrot (^) and two amino acids symbolized by the asterix (*), and the symbols (*)-(^)-(*) correspond to three stapled amino acids of the Formula (iv).

10. The polypeptide of claim 2, wherein the amino acid sequence is selected from the group consisting of:

(SEQ ID NO: 37)
-Q-V-R-E-L-E-A$_5$-Y-I-D-A$_5$-L-L-V-R-V-M-E-E-T-P-N-I-L-R-I-;

(SEQ ID NO: 38)
-Q-V-R-E-L-E-D-A$_5$-I-D-N-A$_5$-L-V-R-V-M-E-E-T-P-N-I-L-R-I-;

(SEQ ID NO: 39)
-Q-V-R-E-L-E-D-Y-I-D-A$_5$-L-L-V-A$_5$-V-M-E-E-T-P-N-I-L-R-I-;

(SEQ ID NO: 40)
-Q-V-R-E-L-E-D-Y-I-D-N-L-L-V-A$_5$-V-M-E-A$_5$-T-P-N-I-L-R-I-;

(SEQ ID NO: 41)
-H-I-R-E-L-E-A$_5$-Y-I-D-A$_5$-L-L-V-R-V-M-E-E-T-P-S-I-L-R-V-;

(SEQ ID NO: 42)
-H-I-R-E-L-E-D-A$_5$-I-D-N-A$_5$-L-V-R-V-M-E-E-T-P-S-I-L-R-V-;

(SEQ ID NO: 43)
-H-I-R-E-L-E-D-Y-I-D-A$_5$-L-L-V-A$_5$-V-M-E-R-T-P-S-I-L-R-V-;

(SEQ ID NO: 44)
-H-I-R-E-L-E-D-Y-I-D-N-L-L-V-A$_5$-V-M-E-A$_5$-T-P-S-I-L-R-V-;

(SEQ ID NO: 45)
-I-N-F-R-L-Q-A$_5$-Y-I-D-A$_5$-I-I-V-A-I-M-E-T-N-P-S-I-L-E-V-;

(SEQ ID NO: 46)
-I-N-F-R-L-Q-D-A$_5$-I-D-R-A$_5$-I-V-A-I-M-E-T-N-P-S-I-L-E-V-;

(SEQ ID NO: 47)
-I-N-F-R-L-Q-D-Y-I-D-A$_5$-I-I-V-A$_5$-I-M-E-T-N-P-S-I-L-E-V-;

(SEQ ID NO: 48)
-I-N-F-R-L-Q-D-Y-I-D-R-I-I-V-A$_5$-I-M-E-A$_5$-N-P-S-I-L-E-V-;

(SEQ ID NO: 49)
-I-N-F-R-L-R-A$_5$-Y-M-D-A$_5$-I-I-L-A-I-L-D-H-N-P-S-I-L-E-I-;

(SEQ ID NO: 50)
-I-N-F-R-L-R-Q-A$_5$-M-D-K-A$_5$-I-L-A-I-L-D-H-N-P-S-I-L-E-I-;

(SEQ ID NO: 51)
-I-N-F-R-L-R-Q-Y-M-D-A$_5$-I-I-L-A$_5$-I-L-D-H-N-P-S-I-L-E-I-;

(SEQ ID NO: 52)
-I-N-F-R-L-R-Q-Y-M-D-K-I-I-L-A$_5$-I-L-D-A$_5$-N-P-S-I-L-E-I;

(SEQ ID NO: 53)
-Q-V-R-E-L-E-A$_5$-Y-I-D-B$_5$-L-L-V-A$_5$-V-M-E-E-T-P-N-I-L-R-I;

(SEQ ID NO: 54)
-Q-V-R-E-L-E-D-Y-I-D-A$_5$-L-L-V-B$_5$-V-M-E-A$_5$-T-P-N-I-L-R-I-;

(SEQ ID NO: 55)
-H-I-R-E-L-E-A$_5$-Y-I-D-B$_5$-L-L-V-A$_5$-V-M-E-E-T-P-S-I-L-R-V-;

(SEQ ID NO: 56)
-H-I-R-E-L-E-D-Y-I-D-A$_5$-L-L-V-B$_5$-V-M-E-A$_5$-T-P-S-I-L-R-V-;

(SEQ ID NO: 57)
-I-N-F-R-L-Q-A$_5$-Y-I-D-B$_5$-I-I-V-A$_5$-I-M-E-T-N-P-S-I-L-E-V-;

(SEQ ID NO: 58)
-I-N-F-R-L-Q-D-Y-I-D-A$_5$-I-I-V-B$_5$-I-M-E-A$_5$-N-P-S-I-L-E-V-;

(SEQ ID NO: 59)
-I-N-F-R-L-R-A$_5$-Y-M-D-B$_5$-I-I-L-A$_5$-I-L-D-H-N-P-S-I-L-E-I;
and (SEQ ID NO: 60)
-I-N-F-R-L-R-Q-Y-M-D-A$_5$-I-I-L-B$_5$-I-L-D-A$_5$-N-P-S-I-L-E-I;

wherein A$_5$ is the amino acid:

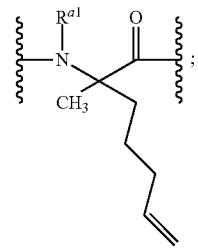

or two A$_5$ amino acids are joined to form an A$_5$-A$_5$ staple; and wherein B$_5$ is the amino acid:

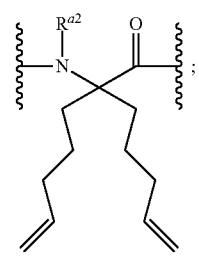

or two $A_5$ amino acids and one $B_5$ amino acid are joined to form an $A_5$-$B_5$-$A_5$ staple.

11. A composition comprising a polypeptide of claim 2, or a pharmaceutically acceptable salt thereof, and optionally a pharmaceutically acceptable excipient.

12. A method of modulating RAB function comprising contacting a polypeptide of claim 2, or a pharmaceutically acceptable salt thereof, and a RAB protein, wherein the polypeptide or salt thereof, binds to the RAB protein.

13. The method of claim 12, wherein the polypeptide is a RAB family interacting protein (FIP) polypeptide.

14. The method of claim 12, wherein the polypeptide substantially inhibits RAB function.

15. The method of claim 12, wherein the polypeptide is derived from FIP1, FIP2, FIP3, or FIP4 protein.

16. The method of claim 12, wherein the polypeptide is selected from the group consisting of:

(SEQ ID NO: 37)
-Q-V-R-E-L-E-$A_5$-Y-I-D-$A_5$-L-L-V-R-V-M-E-E-T-P-N-I-L-R-I-;

(SEQ ID NO: 38)
-Q-V-R-E-L-E-D-$A_5$-I-D-N-$A_5$-L-V-R-V-M-E-E-T-P-N-I-L-R-I-;

(SEQ ID NO: 39)
-Q-V-R-E-L-E-D-Y-I-D-$A_5$-L-L-V-$A_5$-V-M-E-E-T-P-N-I-L-R-I-;

(SEQ ID NO: 40)
-Q-V-R-E-L-E-D-Y-I-D-N-L-L-V-$A_5$-V-M-E-$A_5$-T-P-N-I-L-R-I-;

(SEQ ID NO: 41)
-H-I-R-E-L-E-$A_5$-Y-I-D-$A_5$-L-L-V-R-V-M-E-E-T-P-S-I-L-R-V-;

(SEQ ID NO: 42)
-H-I-R-E-L-E-D-$A_5$-I-D-N-$A_5$-L-V-R-V-M-E-E-T-P-S-I-L-R-V-;

(SEQ ID NO: 43)
-H-I-R-E-L-E-D-Y-I-D-$A_5$-L-L-V-$A_5$-V-M-E-R-T-P-S-I-L-R-V-;

(SEQ ID NO: 44)
-H-I-R-E-L-E-D-Y-I-D-N-L-L-V-$A_5$-V-M-E-$A_5$-T-P-S-I-L-R-V-;

(SEQ ID NO: 45)
-I-N-F-R-L-Q-$A_5$-Y-I-D-$A_5$-I-I-V-A-I-M-E-T-N-P-S-I-L-E-V-;

(SEQ ID NO: 46)
-I-N-F-R-L-Q-D-$A_5$-I-D-R-$A_5$-I-V-A-I-M-E-T-N-P-S-I-L-E-V-;

(SEQ ID NO: 47)
-I-N-F-R-L-Q-D-Y-I-D-$A_5$-I-I-V $A_5$-I-M-E-T-N-P-S-I-L-E-V-;

(SEQ ID NO: 48)
-I-N-F-R-L-Q-D-Y-I-D-R-I-I-V-$A_5$-I-M-E-$A_5$-N-P-S-I-L-E-V-;

(SEQ ID NO: 49)
-I-N-F-R-L-R-$A_5$-Y-M-D-$A_5$-I-I-L-A-I-L-D-H-N-P-S-I-L-E-I-;

(SEQ ID NO: 50)
-I-N-F-R-L-R-Q-$A_5$-M-D-K-$A_5$-I-L-A-I-L-D-H-N-P-S-I-L-E-I-;

(SEQ ID NO: 51)
-I-N-F-R-L-R-Q-Y-M-D-$A_5$-I-I-L-$A_5$-I-L-D-H-N-P-S-I-L-E-I-;

(SEQ ID NO: 52)
-Q-V-R-E-L-E-$A_5$-Y-I-D-$B_5$-L-L-V-$A_5$-V-M-E-E-T-P-N-I-L-R-I-;

(SEQ ID NO: 53)
-Q-V-R-E-L-E-D-Y-I-D-$A_5$-L-L-V-$B_5$-V-M-E-$A_5$-T-P-N-I-L-R-I-;

(SEQ ID NO: 54)
-H-I-R-E-L-E-$A_5$-Y-I-D-$B_5$-L-L-V-$A_5$-V-M-E-E-T-P-S-I-L-R-V-;

(SEQ ID NO: 55)
-H-I-R-E-L-E-D-Y-I-D-$A_5$-L-L-V-$B_5$-V-M-E-$A_5$-T-P-S-I-L-R-V-;

(SEQ ID NO: 56)
-I-N-F-R-L-Q-$A_5$-Y-I-D-$B_5$-I-I-V-$A_5$-I-M-E-T-N-P-S-I-L-E-V-;

(SEQ ID NO: 57)
-I-N-F-R-L-Q-D-Y-I-D-$A_5$-I-I-V-$B_5$-I-M-E-$A_5$-N-P-S-I-L-E-V-;

(SEQ ID NO: 58)
-I-N-F-R-L-R-$A_5$-Y-M-D-$B_5$-I-I-L-$A_5$-I-L-D-H-N-P-S-I-L-E-I-;

(SEQ ID NO: 59)
-I-N-F-R-L-R-Q-Y-M-D-$A_5$-I-I-L-$B_5$-I-L-D-$A_5$-N-P-S-I-L-E-I-;
and (SEQ ID NO: 60)
-I-N-F-R-L-R-Q-Y-M-D-K-I-I-L-$A_5$-I-L-D-$A_5$-N-P-S-I-L-E-I-;

wherein two $A_5$ amino acids are joined to form an $A_5$-$A_5$ staple, or two $A_5$ amino acids and one $B_5$ amino acid are joined to form an $A_5$-$B_5$-$A_5$ staple.

17. The method of claim 12, wherein the RAB protein is RAB11 or RAB25.

18. A method of treating a condition associated with aberrant RAB protein levels or activity comprising administering an effective amount of a polypeptide of claim 2 or a pharmaceutically acceptable salt thereof to a subject in need thereof.

19. The method of claim 18, wherein the condition associated with aberrant RAB protein levels or activity is cancer.

20. The method of claim 19, wherein the cancer is breast or ovarian cancer.

21. The method of claim 18, wherein the condition associated with aberrant RAB protein levels or activity is Griscelli syndrome, Charcot-Marie-Tooth, tuberous sclerosis, or choroideremia.

22. The method of claim 19, wherein the cancer associated with aberrant RAB protein levels or activity is squamous cell carcinomas, neuroendocrine tumors, lung cancer, hepatoma, Medullary thyroid cancer, pancreatic carcinoma, hepatocellular carcinoma, gastric cancer, prostate cancer, liver cancer, ovarian cancer, or breast cancer.

23. The method of claim 18, wherein the condition associated with aberrant RAB protein levels or activity is a proliferative, a neurological, an immunological, an endocrinologic, a cardiovascular, a hematologic, or an inflammatory condition associated with aberrant RAB protein levels or activity.

24. A method of inhibiting a RAB protein from binding to a RAB Family Interacting Protein (FIP), the method comprising administering an effective amount of a polypeptide of claim 2 or a pharmaceutically acceptable salt thereof to a subject in need thereof.

25. The polypeptide of claim 1, wherein the amino acid sequence comprises at least two independent occurrences of an amino acid of Formula (i) or (ii) separated by two or three amino acids.

26. The polypeptide of claim 1, wherein the alpha carbon of the amino acid of Formula (i) is in the (S) configuration.

27. The polypeptide of claim 1, wherein the alpha carbon of the amino acid of Formula (i) is in the (R) configuration.

28. The polypeptide of claim 1, wherein K is unsubstituted $C_{1-6}$alkylene.

29. The polypeptide of claim 1, wherein the amino acid of Formula (i) is selected from the group consisting of:

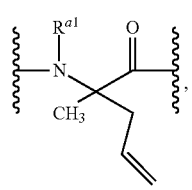 , 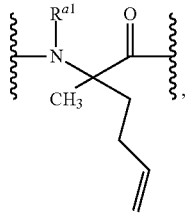 ,

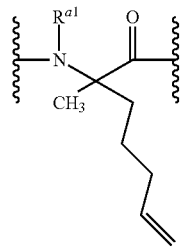 ,

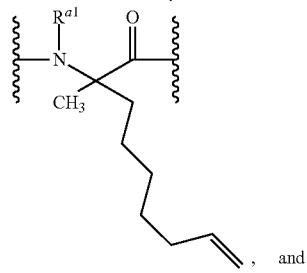 , and

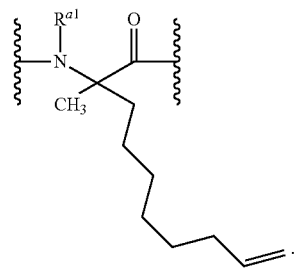 .

30. The polypeptide of claim 29, wherein the amino acid of Formula (i) is:

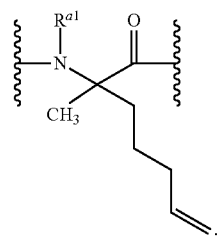 .

31. The polypeptide of claim 1, wherein each instance of $L_1$ and $L_2$ is independently unsubstituted $C_{1-6}$alkylene.

32. The polypeptide of claim 1, wherein the amino acid of Formula (ii) is selected from the group consisting of:

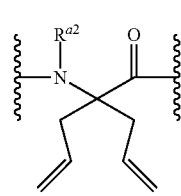 , 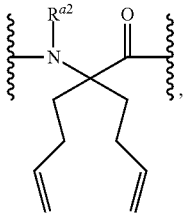 ,

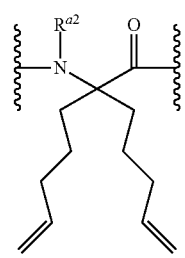 , 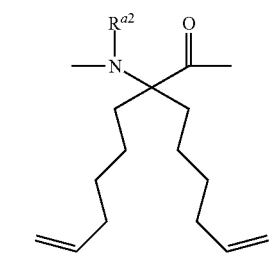 ,

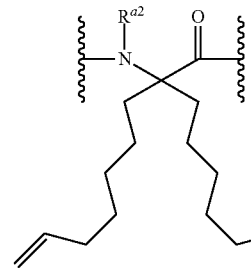 , and

-continued

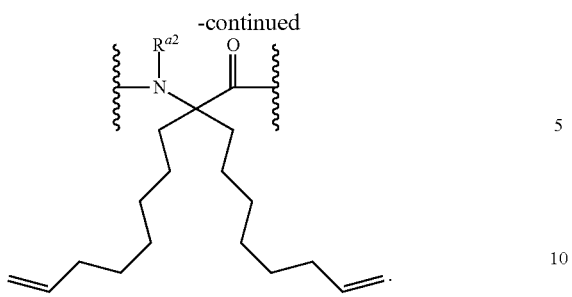

33. The method of claim 12, wherein the polypeptide is positively charged.

34. The method of claim 12, wherein the polypeptide has a hydrocarbon staple corresponding to a) amino acid positions 1253 and 1257, 1254 and 1258, 1258 and 1261, or 1261 and 1265 of the FIP1 protein;
b) amino acid positions 479 and 483, 480 and 484, 484 and 487, or 487 and 491 of the FIP2 protein;
c) amino acid positions 736 and 740, 737 and 741, 741 and 744, or 744 and 748 of the FIP3 protein; or
d) amino acid positions 616 and 620, 617 and 621, 621 and 624, 624 and 628 of the FIP4 protein.

* * * * *